(12) United States Patent
Palermo et al.

(10) Patent No.: US 7,905,900 B2
(45) Date of Patent: *Mar. 15, 2011

(54) CLIP APPLIER AND METHODS OF USE

(75) Inventors: Thomas J. Palermo, San Jose, CA (US); William M. Belef, San Jose, CA (US); Michael T. Carley, San Jose, CA (US); Richard S. Ginn, San Jose, CA (US); Ronald J. Jabba, Redwood City, CA (US); Anthony J. Pantages, San Jose, CA (US); Francisco Javier Sagastegui, Castro Valley, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 515 days.

This patent is subject to a terminal disclaimer.

(21) Appl. No.: 10/356,214

(22) Filed: Jan. 30, 2003

(65) Prior Publication Data
US 2004/0153122 A1    Aug. 5, 2004

(51) Int. Cl.
*A61B 17/08* (2006.01)
(52) U.S. Cl. ...................................................... 606/213
(58) Field of Classification Search .................. 606/213, 606/139–158, 215, 216, 220, 221
See application file for complete search history.

(56) References Cited

U.S. PATENT DOCUMENTS

| 287,046 A | 10/1883 | Norton |
|---|---|---|
| 438,400 A | 10/1890 | Brennen |
| 1,088,393 A | 2/1914 | Backus |
| 1,331,401 A | 2/1920 | Summers |
| 1,426,111 A | 8/1922 | Sacker |
| 1,516,990 A | 11/1924 | Silverman |
| 1,596,004 A | 8/1926 | De Bengoa |
| 1,647,958 A | 11/1927 | Ciarlante |

(Continued)

FOREIGN PATENT DOCUMENTS

CA    2 339 060    2/2000

(Continued)

OTHER PUBLICATIONS

PCT Publication No. WO 00/07640, "Vascular Suction Cannula, Dialator and Surgical Stapler", Feb. 17, 2000.

(Continued)

*Primary Examiner* — Anhtuan T Nguyen
*Assistant Examiner* — Tuan V Nguyen
(74) *Attorney, Agent, or Firm* — Workman Nydegger

(57) ABSTRACT

An apparatus for delivering a closure element into an opening formed in a blood vessel or other body lumen and methods for manufacturing and using same. The apparatus is configured to retain the closure element such that the closure element is disposed substantially within the apparatus. The apparatus also can engage, and position the closure element substantially adjacent to, the blood vessel wall adjacent to the opening. During deployment of the closure element, the apparatus expands the closure element beyond a natural cross-section of the closure element such that the closure element, when deployed, is configured to engage a significant amount of the blood vessel wall and/or tissue. Engaging the blood vessel wall and/or tissue, the closure element is further configured to return to the natural cross-section, thereby drawing the engaged blood vessel wall and/or tissue substantially closed and/or sealed, such that hemostasis within the opening is enhanced.

11 Claims, 24 Drawing Sheets

U.S. PATENT DOCUMENTS

| | | |
|---|---|---|
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,513,848 A | 5/1970 | Winston et al. |
| 3,523,351 A | 8/1970 | Filia |
| 3,525,340 A | 8/1970 | Gilbert |
| 3,604,425 A | 9/1971 | LeRoy |
| 3,618,447 A | 11/1971 | Goins |
| 3,664,345 A | 5/1972 | Dabbs et al. |
| 3,677,243 A | 7/1972 | Nerz |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,976,079 A | 8/1976 | Samuels et al. |
| 3,985,138 A | 10/1976 | Jarvik |
| 4,014,492 A | 3/1977 | Rothfuss |
| 4,018,228 A | 4/1977 | Goosen |
| 3,586,002 A | 6/1977 | Wood |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,480,356 A | 11/1984 | Martin |
| 4,485,816 A | 12/1984 | Krumme |
| RE31,855 E | 3/1985 | Osborn |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,147,381 A | 9/1992 | Heimerl et al. |
| 5,156,609 A | 10/1992 | Nakao et al. |
| 5,158,566 A | 10/1992 | Pianetti |
| 5,160,339 A | 11/1992 | Chen et al. |
| 5,167,634 A | 12/1992 | Corrigan, Jr. et al. |
| 5,167,643 A | 12/1992 | Lynn |

| | | |
|---|---|---|
| 5,171,249 A | 12/1992 | Stefanchik et al. |
| 5,171,250 A | 12/1992 | Yoon |
| 5,171,251 A | 12/1992 | Bregen et al. |
| 5,176,648 A | 1/1993 | Holmes et al. |
| 5,176,682 A | 1/1993 | Chow |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,203,787 A | 4/1993 | Noblitt et al. |
| 5,209,756 A | 5/1993 | Seedhom et al. |
| 5,217,024 A | 6/1993 | Dorsey et al. |
| 5,219,359 A | 6/1993 | McQuilkin et al. |
| 5,222,974 A | 6/1993 | Kensey et al. |
| 5,226,908 A | 7/1993 | Yoon |
| 5,234,449 A | 8/1993 | Bruker et al. |
| 5,236,435 A | 8/1993 | Sewell, Jr. |
| 5,236,445 A | 8/1993 | Hayhurst et al. |
| 5,242,457 A | 9/1993 | Akopov et al. |
| 5,242,459 A | 9/1993 | Buelna |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,258,015 A | 11/1993 | Li et al. |
| 5,269,792 A | 12/1993 | Kovac et al. |
| 5,275,616 A | 1/1994 | Fowler |
| 5,282,808 A | 2/1994 | Kovac et al. |
| 5,282,827 A | 2/1994 | Kensey et al. |
| 5,282,832 A | 2/1994 | Toso et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,184 A | 4/1994 | Hathaway et al. |
| 5,304,204 A | 4/1994 | Bregen |
| 5,306,254 A | 4/1994 | Nash et al. |
| 5,306,280 A | 4/1994 | Bregen et al. |
| 5,318,542 A | 6/1994 | Hirsch et al. |
| 5,320,639 A | 6/1994 | Rudnick |
| 5,330,442 A | 7/1994 | Green et al. |
| 5,330,445 A | 7/1994 | Haaga |
| 5,334,216 A | 8/1994 | Vidal et al. |
| 5,334,217 A | 8/1994 | Das |
| 5,340,360 A | 8/1994 | Stefanchik |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,376,101 A | 12/1994 | Green et al. |
| 5,383,896 A | 1/1995 | Gershony et al. |
| 5,383,905 A | 1/1995 | Golds et al. |
| RE34,866 E | 2/1995 | Kensey et al. |
| 5,391,173 A | 2/1995 | Wilk |
| 5,392,978 A | 2/1995 | Velez |
| 5,395,030 A | 3/1995 | Kuramoto et al. |
| 5,409,499 A | 4/1995 | Yi |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,777 A | 5/1995 | Hofling |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,449,359 A | 9/1995 | Groiso |
| 5,456,400 A | 10/1995 | Shichman et al. |
| 5,462,558 A | 10/1995 | Kolesa et al. |
| 5,462,561 A | 10/1995 | Voda |
| 5,466,241 A | 11/1995 | Leroy et al. |
| 5,470,010 A | 11/1995 | Rothfuss et al. |
| 5,474,557 A | 12/1995 | Mai |
| 5,474,572 A | 12/1995 | Hayhurst |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,501,698 A | 3/1996 | Roth et al. |
| 5,507,744 A | 4/1996 | Tay et al. |
| 5,507,755 A | 4/1996 | Gresl et al. |
| 5,514,159 A | 5/1996 | Matula et al. |
| 5,521,184 A | 5/1996 | Zimmermann |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,543,520 A | 8/1996 | Zimmermann |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,575,771 A | 11/1996 | Walinsky |
| 5,584,879 A | 12/1996 | Reimold et al. |
| 5,591,205 A | 1/1997 | Fowler |
| 5,593,412 A | 1/1997 | Martinez et al. |
| 5,593,422 A | 1/1997 | Muijs Van de Moer et al. |
| 5,593,425 A | 1/1997 | Bonutti et al. |
| 5,601,602 A | 2/1997 | Fowler |
| 5,609,597 A | 3/1997 | Lehrer |
| 5,611,986 A | 3/1997 | Datta et al. |
| 5,613,974 A | 3/1997 | Andreas et al. |
| 5,618,291 A | 4/1997 | Thompson et al. |
| 5,618,306 A | 4/1997 | Roth et al. |
| 5,620,452 A | 4/1997 | Yoon |
| 5,620,461 A | 4/1997 | Muijs et al. |
| 5,630,824 A | 5/1997 | Hart |
| 5,643,318 A | 7/1997 | Tsukernik et al. |
| 5,645,553 A | 7/1997 | Kolesa et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,917 A | 9/1997 | Sauer et al. |
| 5,674,231 A | 10/1997 | Green et al. |
| 5,676,689 A | 10/1997 | Kensey et al. |
| 5,676,974 A | 10/1997 | Valdes et al. |
| 5,681,334 A | 10/1997 | Evans et al. |
| 5,681,351 A | 10/1997 | Jamiolkowski et al. |
| 5,683,405 A | 11/1997 | Yacoubian et al. |
| 5,690,674 A | 11/1997 | Diaz |
| 5,695,505 A | 12/1997 | Yoon |
| 5,695,524 A | 12/1997 | Kelley et al. |
| 5,700,273 A | 12/1997 | Buelna et al. |
| 5,709,708 A | 1/1998 | Thal |
| 5,716,375 A | 2/1998 | Fowler |
| 5,720,755 A | 2/1998 | Dakov |
| 5,720,765 A | 2/1998 | Thal |
| 5,725,498 A | 3/1998 | Janzen et al. |
| 5,725,552 A | 3/1998 | Kotula et al. |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,732,872 A | 3/1998 | Bolduc et al. |
| 5,735,873 A | 4/1998 | MacLean |
| 5,735,875 A | 4/1998 | Bonutti et al. |
| 5,735,877 A | 4/1998 | Pagedas |
| 5,749,898 A | 5/1998 | Schulze et al. |
| 5,752,966 A | 5/1998 | Chang |
| 5,755,726 A | 5/1998 | Pratt et al. |

| | | | | | |
|---|---|---|---|---|---|
| 5,755,778 A | 5/1998 | Kleshinski | 6,036,720 A | 3/2000 | Abrams et al. |
| 5,766,217 A | 6/1998 | Christy | 6,045,570 A | 4/2000 | Epstein et al. |
| 5,766,246 A | 6/1998 | Mulhauser et al. | 6,048,358 A | 4/2000 | Barak |
| 5,769,862 A | 6/1998 | Kammerer et al. | 6,056,768 A | 5/2000 | Cates et al. |
| 5,769,870 A | 6/1998 | Salahieh et al. | 6,056,769 A | 5/2000 | Epstein et al. |
| 5,776,150 A | 7/1998 | Nolan et al. | 6,056,770 A | 5/2000 | Epstein et al. |
| 5,779,707 A | 7/1998 | Bertholet et al. | 6,059,800 A | 5/2000 | Hart et al. |
| 5,782,844 A | 7/1998 | Yoon et al. | 6,063,085 A | 5/2000 | Tay et al. |
| 5,782,860 A | 7/1998 | Epstein et al. | 6,063,114 A | 5/2000 | Nash et al. |
| 5,782,861 A | 7/1998 | Cragg et al. | 6,066,160 A | 5/2000 | Colvin et al. |
| 5,782,864 A | 7/1998 | Lizardi | 6,071,300 A | 6/2000 | Brenneman et al. |
| 5,795,958 A | 8/1998 | Rao et al. | 6,074,409 A | 6/2000 | Goldfarb |
| 5,797,928 A | 8/1998 | Kogasaka | 6,077,281 A | 6/2000 | Das |
| 5,797,931 A | 8/1998 | Bito et al. | 6,077,291 A | 6/2000 | Das |
| 5,797,933 A | 8/1998 | Snow et al. | 6,080,182 A | 6/2000 | Shaw |
| 5,797,958 A | 8/1998 | Yoon | 6,080,183 A | 6/2000 | Tsugita et al. |
| 5,810,776 A | 9/1998 | Bacich et al. | 6,086,608 A | 7/2000 | Ek et al. |
| 5,810,846 A | 9/1998 | Virnich et al. | 6,090,130 A | 7/2000 | Nash et al. |
| 5,810,851 A | 9/1998 | Yoon | 6,092,561 A | 7/2000 | Schmid |
| 5,810,877 A | 9/1998 | Roth et al. | 6,099,553 A | 8/2000 | Hart et al. |
| 5,814,069 A | 9/1998 | Schulze et al. | 6,102,271 A | 8/2000 | Longo et al. |
| 5,817,113 A | 10/1998 | Gifford | 6,106,545 A | 8/2000 | Egan |
| 5,820,631 A | 10/1998 | Nobles | 6,110,184 A | 8/2000 | Weadock |
| 5,827,298 A | 10/1998 | Hart et al. | 6,113,612 A | 9/2000 | Swanson et al. |
| 5,830,125 A | 11/1998 | Scribner et al. | 6,117,125 A | 9/2000 | Rothbarth et al. |
| 5,833,698 A | 11/1998 | Hinchliffe et al. | 6,117,148 A | 9/2000 | Ravo |
| 5,843,167 A | 12/1998 | Dwyer et al. | 6,120,524 A | 9/2000 | Taheri |
| 5,846,254 A | 12/1998 | Schulze et al. | 6,126,675 A | 10/2000 | Schervinsky et al. |
| 5,853,421 A | 12/1998 | Leschinsky et al. | 6,126,677 A | 10/2000 | Ganaja et al. |
| 5,853,422 A | 12/1998 | Huebsch et al. | 6,136,010 A | 10/2000 | Modesitt et al. |
| 5,855,312 A | 1/1999 | Toledano | 6,143,017 A | 11/2000 | Thal |
| 5,858,082 A | 1/1999 | Cruz et al. | 6,149,660 A | 11/2000 | Laufer et al. |
| 5,860,991 A | 1/1999 | Klein et al. | 6,149,667 A | 11/2000 | Hovland et al. |
| 5,861,005 A | 1/1999 | Kontos | 6,152,144 A | 11/2000 | Lesh et al. |
| 5,868,755 A | 2/1999 | Kanner et al. | 6,152,934 A | 11/2000 | Harper et al. |
| 5,868,763 A | 2/1999 | Spence et al. | 6,152,936 A | 11/2000 | Christy et al. |
| 5,871,474 A | 2/1999 | Hermann et al. | 6,152,937 A | 11/2000 | Peterson et al. |
| 5,871,490 A | 2/1999 | Schulze et al. | 6,159,234 A | 12/2000 | Bonutti et al. |
| 5,871,501 A | 2/1999 | Leschinsky et al. | 6,165,204 A | 12/2000 | Levinson et al. |
| 5,871,525 A | 2/1999 | Edwards et al. | 6,174,324 B1 | 1/2001 | Egan et al. |
| 5,873,876 A | 2/1999 | Christy | 6,193,734 B1 | 2/2001 | Bolduc et al. |
| 5,879,366 A | 3/1999 | Shaw et al. | 6,197,042 B1 | 3/2001 | Ginn et al. ................ 606/213 |
| 5,893,592 A | 4/1999 | Schulze et al. | 6,200,329 B1 | 3/2001 | Fung et al. |
| 5,897,487 A | 4/1999 | Ouchi | 6,203,565 B1 | 3/2001 | Bonutti et al. |
| 5,902,310 A | 5/1999 | Foerster et al. | 6,206,913 B1 | 3/2001 | Yencho et al. |
| 5,904,697 A | 5/1999 | Gifford, III et al. | 6,220,248 B1 | 4/2001 | Voegele et al. |
| 5,906,631 A | 5/1999 | Imran | 6,221,102 B1 | 4/2001 | Baker et al. |
| 5,907,893 A | 6/1999 | Zadno-Azizi et al. | 6,231,592 B1 | 5/2001 | Bonutti et al. |
| 5,910,155 A | 6/1999 | Ratcliff et al. | 6,248,124 B1 | 6/2001 | Pedros et al. |
| 5,919,207 A | 7/1999 | Taheri | 6,254,615 B1 | 7/2001 | Bolduc et al. |
| 5,919,208 A | 7/1999 | Valenti | 6,254,617 B1 | 7/2001 | Spence et al. |
| 5,922,009 A | 7/1999 | Epstein et al. | 6,254,642 B1 | 7/2001 | Taylor |
| 5,935,147 A | 8/1999 | Kensey et al. | 6,277,140 B2 | 8/2001 | Ginn et al. |
| 5,938,667 A | 8/1999 | Peyser et al. | 6,280,460 B1 | 8/2001 | Bolduc et al. |
| 5,941,890 A | 8/1999 | Voegele et al. | 6,287,322 B1 | 9/2001 | Zhu et al. |
| 5,947,999 A | 9/1999 | Groiso | 6,296,657 B1 | 10/2001 | Brucker |
| 5,951,518 A | 9/1999 | Licata et al. | 6,305,891 B1 | 10/2001 | Burlingame |
| 5,951,576 A | 9/1999 | Wakabayashi | 6,319,258 B1 | 11/2001 | McAllen, III et al. |
| 5,951,589 A | 9/1999 | Epstein et al. | 6,322,580 B1 | 11/2001 | Kanner |
| 5,957,936 A | 9/1999 | Yoon et al. | 6,334,865 B1 | 1/2002 | Redmond et al. |
| 5,957,938 A | 9/1999 | Zhu et al. | 6,348,064 B1 * | 2/2002 | Kanner ................ 606/219 |
| 5,964,782 A | 10/1999 | LaFontaine et al. | 6,358,258 B1 | 3/2002 | Arcia et al. |
| 5,976,159 A | 11/1999 | Bolduc et al. | D457,958 S | 5/2002 | Dycus |
| 5,976,161 A | 11/1999 | Kirsch et al. | 6,383,208 B1 | 5/2002 | Sancoff et al. |
| 5,984,934 A | 11/1999 | Ashby et al. | 6,391,048 B1 | 5/2002 | Ginn et al. ................ 606/213 |
| 5,984,949 A | 11/1999 | Levin | 6,395,015 B1 | 5/2002 | Borst et al. |
| 5,993,468 A | 11/1999 | Rygaard | 6,398,752 B1 | 6/2002 | Sweezer et al. |
| 5,993,476 A | 11/1999 | Groiso | 6,402,765 B1 | 6/2002 | Monassevitch et al. ....... 606/151 |
| 6,001,110 A | 12/1999 | Adams | 6,409,739 B1 | 6/2002 | Nobles et al. |
| 6,004,341 A | 12/1999 | Zhu et al. | 6,419,669 B1 | 7/2002 | Frazier et al. |
| 6,007,563 A | 12/1999 | Nash et al. | 6,423,054 B1 | 7/2002 | Ouchi |
| 6,013,084 A | 1/2000 | Ken et al. | 6,428,472 B1 | 8/2002 | Haas |
| 6,022,372 A | 2/2000 | Kontos | 6,428,548 B1 | 8/2002 | Durgin et al. |
| 6,024,750 A | 2/2000 | Mastri | 6,443,158 B1 | 9/2002 | Lafontaine et al. |
| 6,024,758 A | 2/2000 | Thal | 6,443,963 B1 | 9/2002 | Baldwin et al. |
| 6,030,364 A * | 2/2000 | Durgin et al. ........... 604/164.1 | 6,447,540 B1 | 9/2002 | Fontaine et al. |
| 6,030,413 A | 2/2000 | Lazarus | 6,450,391 B1 | 9/2002 | Kayan et al. |
| 6,033,427 A | 3/2000 | Lee | 6,458,130 B1 | 10/2002 | Frazier et al. |
| 6,036,703 A | 3/2000 | Evans et al. | 6,461,364 B1 | 10/2002 | Ginn et al. ................ 606/142 |

| | | | | | | |
|---|---|---|---|---|---|---|
| 6,482,224 B1 | 11/2002 | Michler et al. | | 7,326,230 B2 | 2/2008 | Ravikumar |
| 6,488,692 B1 | 12/2002 | Spence et al. | | 7,331,979 B2 | 2/2008 | Khosravi et al. |
| 6,500,115 B2 | 12/2002 | Krattiger et al. | | 7,335,220 B2 | 2/2008 | Khosravi et al. |
| 6,506,210 B1 | 1/2003 | Kanner ............ 606/213 | | D566,272 S | 4/2008 | Walberg et al. |
| 6,517,569 B2 | 2/2003 | Mikus et al. | | 7,361,183 B2 | 4/2008 | Ginn |
| 6,533,762 B2 | 3/2003 | Kanner et al. | | 7,361,185 B2 | 4/2008 | O'Malley et al. |
| 6,533,812 B2 | 3/2003 | Swanson et al. | | 7,393,363 B2 | 7/2008 | Ginn |
| 6,537,288 B2 | 3/2003 | Vargas et al. | | 7,396,359 B1 | 7/2008 | Derowe et al. |
| 6,547,806 B1 | 4/2003 | Ding | | 7,533,790 B1 | 5/2009 | Knodel et al. |
| 6,569,173 B1 | 5/2003 | Blatter et al. | | 7,597,706 B2 | 10/2009 | Kanner et al. |
| 6,569,185 B2 | 5/2003 | Ungs | | D611,144 S | 3/2010 | Reynolds |
| 6,572,629 B2 | 6/2003 | Kalloo et al. | | 2001/0007077 A1 | 7/2001 | Ginn et al. |
| 6,582,452 B2 | 6/2003 | Coleman et al. | | 2001/0031972 A1 | 10/2001 | Robertson et al. |
| 6,582,482 B2 | 6/2003 | Coleman et al. ............ 606/213 | | 2001/0046518 A1 | 11/2001 | Sawhney |
| 6,599,303 B1 | 7/2003 | Peterson et al. | | 2001/0047180 A1 | 11/2001 | Grudem et al. ............ 606/153 |
| 6,602,263 B1 | 8/2003 | Swanson et al. | | 2002/0026208 A1* | 2/2002 | Roe et al. .............. 606/190 |
| 6,610,072 B1 | 8/2003 | Christy et al. | | 2002/0026215 A1 | 2/2002 | Redmond et al. |
| 6,613,059 B2 | 9/2003 | Schaller et al. | | 2002/0038127 A1 | 3/2002 | Blatter et al. |
| 6,616,686 B2 | 9/2003 | Coleman et al. | | 2002/0042622 A1 | 4/2002 | Vargas et al. |
| 6,623,509 B2 | 9/2003 | Ginn | | 2002/0049427 A1 | 4/2002 | Wiener et al. |
| 6,623,510 B2* | 9/2003 | Carley et al. ............ 606/213 | | 2002/0049472 A1 | 4/2002 | Coleman et al. |
| 6,626,918 B1 | 9/2003 | Ginn et al. | | 2002/0058960 A1 | 5/2002 | Hudson et al. |
| 6,632,238 B2 | 10/2003 | Ginn et al. | | 2002/0072768 A1* | 6/2002 | Ginn ........................ 606/213 |
| 6,634,537 B2 | 10/2003 | Chen | | 2002/0077657 A1 | 6/2002 | Ginn et al. |
| 6,645,205 B2 | 11/2003 | Ginn | | 2002/0082641 A1 | 6/2002 | Ginn et al. .............. 606/213 |
| 6,652,538 B2 | 11/2003 | Kayan et al. | | 2002/0099389 A1 | 7/2002 | Michler et al. |
| 6,652,556 B1 | 11/2003 | VanTassel et al. | | 2002/0106409 A1 | 8/2002 | Sawhney et al. |
| 6,663,655 B2 | 12/2003 | Ginn et al. | | 2002/0107542 A1 | 8/2002 | Kanner et al. |
| 6,665,906 B2 | 12/2003 | Li | | 2002/0133193 A1 | 9/2002 | Ginn et al. |
| 6,669,714 B2 | 12/2003 | Coleman et al. | | 2002/0151921 A1 | 10/2002 | Kanner et al. |
| 6,676,671 B2 | 1/2004 | Robertson et al. | | 2002/0188318 A1 | 12/2002 | Carleyt et al. ............ 606/213 |
| 6,676,685 B2 | 1/2004 | Pedros et al. | | 2002/0193808 A1* | 12/2002 | Belef et al. ............... 606/139 |
| 6,679,904 B2 | 1/2004 | Gleeson et al. | | 2003/0004543 A1 | 1/2003 | Gleeson et al. |
| 6,689,147 B1 | 2/2004 | Koster, Jr. | | 2003/0009180 A1 | 1/2003 | Hinchliffe et al. |
| 6,695,867 B2* | 2/2004 | Ginn et al. ............... 606/213 | | 2003/0009196 A1 | 1/2003 | Peterson |
| 6,699,256 B1 | 3/2004 | Logan et al. | | 2003/0032981 A1 | 2/2003 | Kanner et al. |
| 6,702,826 B2 | 3/2004 | Liddicoat et al. | | 2003/0065358 A1 | 4/2003 | Frecker et al. |
| 6,712,836 B1 | 3/2004 | Berg et al. | | 2003/0078598 A1 | 4/2003 | Ginn et al. |
| 6,719,777 B2 | 4/2004 | Ginn et al. ............... 606/213 | | 2003/0083679 A1 | 5/2003 | Grudem et al. |
| 6,726,704 B1 | 4/2004 | Loshakove et al. .......... 606/213 | | 2003/0093096 A1 | 5/2003 | McGuckin et al. |
| 6,743,195 B2 | 6/2004 | Zucker | | 2003/0097140 A1 | 5/2003 | Kanner |
| 6,743,243 B1 | 6/2004 | Roy et al. | | 2003/0109890 A1 | 6/2003 | Kanner et al. |
| 6,743,259 B2 | 6/2004 | Ginn | | 2003/0125766 A1 | 7/2003 | Ding |
| 6,749,621 B2* | 6/2004 | Pantages et al. ............ 606/213 | | 2003/0158577 A1 | 8/2003 | Pantages et al. |
| 6,749,622 B2 | 6/2004 | McGuckin et al. | | 2003/0158578 A1 | 8/2003 | Pantages et al. |
| 6,755,842 B2 | 6/2004 | Kanner et al. | | 2003/0195504 A1 | 10/2003 | Tallarida et al. |
| 6,767,356 B2 | 7/2004 | Kanner et al. | | 2003/0195561 A1* | 10/2003 | Carley et al. ............ 606/213 |
| 6,780,197 B2* | 8/2004 | Roe et al. .............. 606/213 | | 2004/0009205 A1 | 1/2004 | Sawhney |
| 6,837,906 B2 | 1/2005 | Ginn | | 2004/0009289 A1* | 1/2004 | Carley et al. ............ 427/2.1 |
| 6,846,319 B2 | 1/2005 | Ginn et al. | | 2004/0010285 A1* | 1/2004 | Carley et al. ............ 606/213 |
| 6,890,343 B2 | 5/2005 | Ginn et al. | | 2004/0039414 A1* | 2/2004 | Carley et al. ............ 606/213 |
| 6,896,687 B2 | 5/2005 | Dakov | | 2004/0073236 A1* | 4/2004 | Carley et al. ............ 606/151 |
| 6,896,692 B2 | 5/2005 | Ginn et al. | | 2004/0073255 A1 | 4/2004 | Ginn et al. |
| 6,926,723 B1 | 8/2005 | Mulhauser et al. | | 2004/0082906 A1 | 4/2004 | Tallarida et al. |
| 6,926,731 B2 | 8/2005 | Coleman et al. | | 2004/0087985 A1 | 5/2004 | Loshakove et al. |
| 6,942,674 B2 | 9/2005 | Belef et al. | | 2004/0092964 A1 | 5/2004 | Modesitt et al. |
| 6,942,691 B1 | 9/2005 | Chuter | | 2004/0092968 A1 | 5/2004 | Caro et al. |
| 6,964,668 B2 | 11/2005 | Modesitt et al. | | 2004/0093027 A1 | 5/2004 | Fabisiak et al. |
| 6,969,397 B2 | 11/2005 | Ginn | | 2004/0097978 A1 | 5/2004 | Modesitt et al. |
| 6,989,003 B2* | 1/2006 | Wing et al. ............... 604/161 | | 2004/0127940 A1 | 7/2004 | Ginn et al. |
| 6,989,016 B2 | 1/2006 | Tallarida et al. | | 2004/0143290 A1 | 7/2004 | Brightbill |
| 7,001,398 B2 | 2/2006 | Carley et al. | | 2004/0153122 A1* | 8/2004 | Palermo .................... 606/213 |
| 7,001,400 B1 | 2/2006 | Modesitt et al. | | 2004/0153123 A1* | 8/2004 | Palermo et al. ............ 606/213 |
| 7,008,435 B2 | 3/2006 | Cummins | | 2004/0158127 A1 | 8/2004 | Okada |
| 7,008,439 B1 | 3/2006 | Janzen et al. | | 2004/0158287 A1 | 8/2004 | Cragg et al. |
| 7,033,379 B2 | 4/2006 | Peterson | | 2004/0167511 A1 | 8/2004 | Buehlmann et al. |
| 7,060,084 B1 | 6/2006 | Loshakove et al. | | 2004/0167570 A1* | 8/2004 | Pantages et al. ............ 606/213 |
| 7,063,711 B1 | 6/2006 | Loshakove et al. | | 2004/0191277 A1 | 9/2004 | Sawhney et al. |
| 7,083,635 B2 | 8/2006 | Ginn | | 2004/0215232 A1 | 10/2004 | Belhe et al. |
| 7,108,709 B2 | 9/2006 | Cummins | | 2004/0254591 A1 | 12/2004 | Kanner et al. |
| 7,108,710 B2 | 9/2006 | Anderson | | 2004/0267193 A1 | 12/2004 | Bagaoisan et al. |
| 7,111,768 B2 | 9/2006 | Cummins et al. | | 2004/0267308 A1 | 12/2004 | Bagaoisan et al. |
| 7,112,225 B2 | 9/2006 | Ginn | | 2004/0267312 A1 | 12/2004 | Kanner et al. |
| 7,144,411 B2 | 12/2006 | Ginn et al. | | 2005/0059982 A1 | 3/2005 | Zung et al. |
| 7,163,551 B2 | 1/2007 | Anthony et al. | | 2005/0075665 A1 | 4/2005 | Brenzel et al. |
| 7,169,158 B2 | 1/2007 | Sniffin et al. | | 2005/0085851 A1 | 4/2005 | Fiehler et al. |
| 7,169,164 B2 | 1/2007 | Borillo et al. | | 2005/0085854 A1 | 4/2005 | Ginn |
| 7,211,101 B2 | 5/2007 | Carley et al. | | 2005/0085855 A1 | 4/2005 | Forsberg |
| 7,316,704 B2 | 1/2008 | Bagaoisan et al. | | 2005/0090859 A1 | 4/2005 | Ravikumar |

| Publication | Date | Inventor | | Country | Number | Date |
|---|---|---|---|---|---|---|
| 2005/0119695 A1* | 6/2005 | Carley et al. | 606/213 | IE | S 2002/0664 | 2/2003 |
| 2005/0121042 A1 | 6/2005 | Belhe et al. | | IE | S 2002/0665 | 2/2003 |
| 2005/0149117 A1 | 7/2005 | Khosravi et al. | | IE | S 2002/0451 | 7/2003 |
| 2005/0165357 A1* | 7/2005 | McGuckin et al. | 604/171 | IE | S 2002/0552 | 7/2003 |
| 2005/0177189 A1 | 8/2005 | Ginn et al. | | IE | S 2003/0424 | 12/2003 |
| 2005/0216057 A1 | 9/2005 | Coleman et al. | | IE | S 2003/0490 | 1/2004 |
| 2005/0222614 A1 | 10/2005 | Ginn et al. | | IE | S 2004/0368 | 11/2005 |
| 2005/0234508 A1 | 10/2005 | Cummins et al. | | IE | S 2005/0342 | 11/2005 |
| 2005/0245876 A1 | 11/2005 | Khosravi et al. | | JP | 58-181006 | 12/1983 |
| 2005/0267528 A1 | 12/2005 | Ginn et al. | | JP | 12 74750 | 11/1989 |
| 2005/0267530 A1 | 12/2005 | Cummins et al. | | JP | 11500642 | 8/1997 |
| 2005/0273136 A1 | 12/2005 | Belef et al. | | JP | 2000102546 | 4/2000 |
| 2005/0273137 A1 | 12/2005 | Ginn | | NL | 9302140 | 7/1995 |
| 2005/0274768 A1 | 12/2005 | Cummins et al. | | PL | 171425 | 4/1997 |
| 2005/0283188 A1 | 12/2005 | Loshakove et al. | | RU | 2086192 | 8/1997 |
| 2006/0020270 A1 | 1/2006 | Jabba et al. | | SU | 197801 | 6/1967 |
| 2006/0034930 A1 | 2/2006 | Khosravi et al. | | SU | 495067 | 12/1975 |
| 2006/0047313 A1 | 3/2006 | Khanna et al. | | SU | 912155 | 3/1982 |
| 2006/0100664 A1 | 5/2006 | Pai et al. | | SU | 1243708 | 7/1986 |
| 2006/0135989 A1 | 6/2006 | Carley et al. | | SU | 1324650 | 7/1987 |
| 2006/0144479 A1 | 7/2006 | Carley et al. | | SU | 1405828 | 6/1988 |
| 2006/0167484 A1 | 7/2006 | Carley et al. | | SU | 1456109 | 2/1989 |
| 2006/0190014 A1 | 8/2006 | Ginn et al. | | SU | 1560133 | 4/1990 |
| 2006/0190037 A1 | 8/2006 | Carley et al. | | WO | WO 95/21573 | 8/1995 |
| 2006/0190038 A1 | 8/2006 | Carley et al. | | WO | WO 96/24291 | 8/1996 |
| 2006/0195123 A1 | 8/2006 | Ginn et al. | | WO | WO 97/07741 | 3/1997 |
| 2006/0195124 A1 | 8/2006 | Ginn et al. | | WO | WO 97/27897 | 8/1997 |
| 2006/0253037 A1 | 11/2006 | Ginn et al. | | WO | WO 97/28745 | 8/1997 |
| 2006/0253072 A1 | 11/2006 | Pai et al. | | WO | WO 98/06346 | 2/1998 |
| 2006/0265012 A1 | 11/2006 | Anderson | | WO | WO 98/06448 | 2/1998 |
| 2006/0287674 A1 | 12/2006 | Ginn et al. | | WO | WO 98/16161 | 4/1998 |
| 2007/0010853 A1 | 1/2007 | Ginn et al. | | WO | WO 98/17179 | 4/1998 |
| 2007/0010854 A1 | 1/2007 | Cummins et al. | | WO | WO 98/18389 | 5/1998 |
| 2007/0021778 A1 | 1/2007 | Carly | | WO | WO 98/25508 | 6/1998 |
| 2007/0049967 A1 | 3/2007 | Sibbitt, Jr. et al. | | WO | WO 98/58591 | 12/1998 |
| 2007/0049968 A1 | 3/2007 | Sibbitt, Jr. et al. | | WO | WO 99/21491 | 5/1999 |
| 2007/0060895 A1 | 3/2007 | Sibbitt, Jr. et al. | | WO | WO 99/60941 | 12/1999 |
| 2007/0060950 A1 | 3/2007 | Khosravi et al. | | WO | WO 99/62415 | 12/1999 |
| 2007/0123817 A1 | 5/2007 | Khosravi et al. | | WO | WO 00/06029 | 2/2000 |
| 2007/0203506 A1 | 8/2007 | Sibbitt, Jr. et al. | | WO | WO 00/07505 | 2/2000 |
| 2007/0250080 A1 | 10/2007 | Jones et al. | | WO | WO 00/27311 | 5/2000 |
| 2008/0004636 A1 | 1/2008 | Walberg | | WO | WO 00/27313 | 5/2000 |
| 2008/0009794 A1 | 1/2008 | Bagaoisan et al. | | WO | WO 00/56228 | 9/2000 |
| 2008/0065151 A1 | 3/2008 | Ginn | | WO | WO 00/71032 | 11/2000 |
| 2008/0065152 A1 | 3/2008 | Carley | | WO | WO 01/21058 | 3/2001 |
| 2008/0086075 A1 | 4/2008 | Isik et al. | | WO | WO 01/35832 | 5/2001 |
| 2008/0221616 A1 | 9/2008 | Ginn et al. | | WO | WO 01/47594 | 7/2001 |
| 2008/0312686 A1 | 12/2008 | Ellingwood | | WO | WO 01/49186 | 7/2001 |
| 2008/0319475 A1 | 12/2008 | Clark | | WO | WO 01/91628 | 12/2001 |
| 2009/0157101 A1 | 6/2009 | Reyes et al. | | WO | WO 02/19915 | 3/2002 |
| 2009/0157102 A1 | 6/2009 | Reynolds et al. | | WO | WO 02/19920 | 3/2002 |
| 2009/0157103 A1 | 6/2009 | Walberg et al. | | WO | WO 02/19922 | 3/2002 |
| 2009/0254119 A1 | 10/2009 | Sibbitt, Jr. et al. | | WO | WO 02/19924 | 3/2002 |
| 2010/0130965 A1 | 5/2010 | Sibbitt, Jr. | | WO | WO 02/28286 | 4/2002 |
| 2010/0168790 A1 | 7/2010 | Clark | | WO | WO 02/38055 | 5/2002 |
| | | | | WO | WO 02/45593 | 6/2002 |
| FOREIGN PATENT DOCUMENTS | | | | WO | WO 02/45594 | 6/2002 |
| DE | 197 11 288 | 1/1998 | | WO | WO 02/062234 | 8/2002 |
| DE | 297 23 736 U 1 | 4/1999 | | WO | WO 02/098302 | 12/2002 |
| DE | 19859952 | 2/2000 | | WO | WO 03/013363 | 2/2003 |
| EP | 0 386 361 | 9/1990 | | WO | WO 03/013364 | 2/2003 |
| EP | 0 534 696 | 3/1993 | | WO | WO 03/047434 | 6/2003 |
| EP | 0 756 851 | 2/1997 | | WO | WO 03/071955 | 9/2003 |
| EP | 0 774 237 | 5/1997 | | WO | WO 03/071956 | 9/2003 |
| EP | 0 858 776 | 8/1998 | | WO | WO 03/071957 | 9/2003 |
| EP | 0 941 697 | 9/1999 | | WO | WO 03/094748 | 11/2003 |
| FR | 2 443 238 | 7/1980 | | WO | WO 03/101310 | 12/2003 |
| FR | 2 715 290 | 7/1995 | | WO | WO 2004/004578 | 1/2004 |
| FR | 2 722 975 | 2/1996 | | WO | WO 2004/060169 | 7/2004 |
| FR | 2 768 324 | 3/1999 | | WO | WO 2004/069054 | 8/2004 |
| GB | 1 358 466 | 7/1974 | | WO | WO 2005/000126 | 1/2005 |
| GB | 2 075 144 | 11/1981 | | WO | WO 2005/041782 | 5/2005 |
| IE | S 2000/0722 | 10/2001 | | WO | WO 2005/063129 | 7/2005 |
| IE | S 2000/0724 | 10/2001 | | WO | WO 2005/082256 | 9/2005 |
| IE | S 2001/0547 | 7/2002 | | WO | WO 2005/092204 | 10/2005 |
| IE | S 2001/0815 | 7/2002 | | WO | WO 2005/112782 | 12/2005 |
| IE | S 2001/0748 | 8/2002 | | WO | WO 2005/115251 | 12/2005 |
| IE | S 2001/0749 | 8/2002 | | WO | WO 2005/115521 | 12/2005 |
| IE | S 2002/0452 | 12/2002 | | WO | WO 2006/000514 | 1/2006 |

| | | |
|---|---|---|
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2008/031102 | 3/2008 |
| WO | WO 2009/079091 | 6/2009 |
| WO | WO 2010/031050 | 3/2010 |
| ZA | 20010527 | 1/2001 |
| ZA | 200100528 | 1/2001 |

OTHER PUBLICATIONS

"Hand tool for forming telephone connections—comprises pliers with reciprocably driven ram crimping clip around conductors against anvil", Derwent-ACC-No. 1978-B8090A.
U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
Database WPI; Section PQ, Week 200120; Derwent Publications Ltd., London GB; AN 2001-203165; XP002199926 & ZA 200 100 528 A (Anthony T), Feb. 28, 2001 abstract.
Stretch Comb by Scunci, retrieved via internet at www.scunci.com/productdetail by examiner on Oct. 9, 2007, publication date unavailable.
2002/0072768, Office Action, Aug. 27, 2004.
2002/0072768, Office Action, Feb. 23, 2005.
2002/0072768, Office Action, Apr. 11, 2005.
2002/0072768, Office Action, Jul. 27, 2005.
2002/0072768, Office Action, Mar. 6, 2006.
2002/0072768, Office Action, May 24, 2006.
2002/0072768, Office Action, Oct. 26, 2006.
2002/0072768, Office Action, Apr. 19, 2007.
2002/0133193, Office Action, Nov. 4, 2004.
2002/0133193, Office Action, May 4, 2005.
2002/0133193, Office Action, Oct. 18, 2005.
2002/0133193, Notice of Allowance, Apr. 18, 2007.
2002/0133193, Notice of Allowance, Sep. 27, 2007.
2003/0078598, Office Action, Feb. 9, 2005.
2003/0078598, Office Action, May 26, 2005.
2003/0078598, Office Action, Oct. 4, 2005.
2003/0078598, Notice of Allowance, May 10, 2006.
2003/0078598, Notice of Allowance, Jul. 2, 2007.
2003/0195561, Office Action, Jun. 10, 2004.
2003/0195561, Notice of Allowance, Sep. 21, 2004.
2003/0195561, Office Action, Jan. 3, 2006.
2003/0195561, Issue Notification, Feb. 15, 2006.
2003/0195561, Office Action, May 16, 2006.
2003/0195561, Notice of Allowance, Dec. 28, 2006.
2003/0195561, Notice of Allowance, Jul. 10, 2007.
2003/0195561, Notice of Allowance, Aug. 2, 2007.
2004/0153123, Office Action Sep. 22, 2006.
2004/0153123, Office Action, Jan. 31, 2007.
2003/0153123, Office Action, Sep. 18, 2007.
2004/0073255, Office Action, Sep. 15, 2006.
2004/0073255, Office Action, Apr. 18, 2007.
2004/0073236, Office Action, Sep. 19, 2006.
2004/0073236, Office Action, May 2, 2007.
2004/0009289, Office Action, Jun. 30, 2006.
2004/0009289, Office Action, Oct. 20, 2006.
2004/0009289, Office Action, May 29, 2007.
2004/0167570, Office Action, Oct. 30, 2006.
2004/0167570, Office Action, Apr. 17, 2007.
2004/0167570, Office Action, Aug. 31, 2007.
2005/0274768, Office Action, Oct. 19, 2006.
2005/0274768, Office Action, Aug. 10, 2007.
2005/0216057, Office Action, Feb. 6, 2007.
2005/0216057, Office Action, May 30, 2007.
2005/0234508, Office Action, Aug. 13, 2007.
2006/0135989, Office Action, Nov. 30, 2006.
2006/0135989, Office Action, Sep. 5, 2007.
2006/0195124, Office Action, Jun. 6, 2007.
2006/0195123, Office Action, May 14, 2007.
6,197,042, Notice of Allowance, Nov. 6, 2000.
6,197,042, Issue Notification, Feb. 15, 2001.
6,277,140, Office Action, Mar. 26, 2001.
6,277,140, Notice of Allowance, Jun. 4, 2001.
6,277,140, Issue Notification, Aug. 6, 2001.
6,391,048, Notice of Allowance, Mar. 26, 2001.
6,391,048, Office Action, Sep. 5, 2001.
6,391,048, Notice of Allowance, Feb. 11, 2002.
6,391,048, Issue Notification, May 3, 2002.
6,461,364, Notice of Allowance, May 6, 2002.
6,461,364, Issue Notification, Sep. 19, 2002.
6,582,452, Notice of Allowance, Jan. 31, 2003.
6,582,452, Issue Notification, Jun. 5, 2003.
6,616,686, Office Action, Dec. 17, 2002.
6,616,686, Notice of Allowance, Apr. 21, 2003.
6,616,686, Issue Notification, Aug. 21, 2003.
6,623,510, Notice of Allowance, Apr. 11, 2003.
6,623,510, Office Action, Jun. 9, 2003.
6,623,510, Issue Notification, Sep. 4, 2003.
6,623,238, Office Action, Feb. 26, 2003.
6,632,238, Notice of Allowance, Jun. 16, 2003.
6,632,238, Issue Notification, Sep. 25, 2003.
6,669,714, Office Action, Mar. 4, 2003.
6,669,714, Notice of Allowance, Jul. 28, 2003.
6,669,714, Issue Notification, Dec. 11, 2003.
6,695,867, Notice of Allowance, Sep. 29, 2003.
6,695,867, Issue Notification, Feb. 5, 2004.
6,719,777, Office Action, Feb. 20, 1987.
6,719,777, Notice of Allowance, Jul. 24, 1987.
6,719,777, Issue Notification, Mar. 25, 2004.
6,749,621, Notice of Allowance, Feb. 9, 2004.
6,749,621, Office Action, Apr. 13, 2004.
6,749,621, Issue Notification, May 27, 2004.
6,780,197, Office Action, Sep. 11, 2003.
6,780,197, Office Action, Feb. 9, 2004.
6,780,197, Notice of Allowance, Mar. 17, 2004.
6,780,197, Issue of Notification, Aug. 5, 2004.
6,926,731, Office Action, Nov. 16, 2004.
6,926,731, Notice of Allowance, Apr. 6, 2005.
6,926,731, Issue Notification, Jul. 20, 2005.
6,942,674, Office Action, Sep. 29, 2004.
6,942,674, Notice of Allowance, May 13, 2005.
6,942,674, Issue Notification, Aug. 24, 2005.
7,001,398, Office Action, Mar. 22, 2005.
7,001,398, Notice of Allowance, Jul. 6, 2005.
7,001,398, Notice of Allowance, Oct. 5, 2005.
7,001,398, Issue Notification, Feb. 21, 2006.
7,008,435, Office Action, Apr. 20, 2005.
7,008,435, Office Action, Aug. 10, 2005.
7,008,435, Notice of Allowance, Oct. 18, 2005.
7,008,435, Issue Notification, Feb. 15, 2006.
7,108,709, Office Action, Jul. 27, 2004.
7,108,709, Office Action, Dec. 17, 2004.
7,108,709, Notice of Allowance, Mar. 9, 2005.
7,108,709, Office Action, Aug. 11, 2006.
7,108,709, Issue Notification, Aug. 30, 2006.
7,111,768, Office Action, Feb. 23, 2006.
7,111,768, Notice of Allowance, May 31, 2006.
7,111,768, Issue Notification, Sep. 6, 2006.
7,163,551, Office Action, Jan. 10, 2006.
7,163,551, Notice of Allowance, Sep. 20, 2006.
7,163,551, Issue Notification, Dec. 27, 2006.
7,211,101, Office Action, Aug. 10, 2005.
7,211,101, Office Action, Dec. 19, 2005.
7,211,101, Office Action, Apr. 21, 2006.

7,211,101, Notice of Allowance, Dec. 27, 2006.
7,211,101, Issue Notification, Apr. 11, 2007.
U.S. Appl. No. 10/541,083, Office Action, Oct. 16, 2007.
Deepak Mital et al, Renal Transplantation Without Sutures Using The Vascular Clipping System For Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chicage, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chicago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
MD Gonze et al, Complications associated with percutaneous closure devices, Conference: Annual Meeting of the Society for Clinical Vascular Surgery, The American journal or surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrecht University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive. org, Jun. 1998, Original Publisher: http://prostar.com, may also be found at http://web.archive.org/web/19980630040429/www. perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25—No. 2, Supplement 1.
Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 10/435,104, mailed Sep. 26, 2008, Notice of Allowance.
U.S. Appl. No. 10/542,083, mailed Sep. 19, 2008, Notice of Allowance.
U.S. Appl. No. 10/616,832, mailed Sep. 17, 2008, Office Action.
U.S. Appl. No. 11/198,811, mailed Aug. 26, 2008, Office Action.
U.S. Appl. No. 11/406,203, mailed Sep. 22, 2008, Notice of Allowance.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 12/106,928, filed Apr. 21, 2008, Ginn et al.
U.S. Appl. No. 12/106,937, filed Apr. 21, 2008, Ginn et al.
U.S. Appl. No. 12/113,092, filed Apr. 30, 2008, Ginn et al.
U.S. Appl. No. 12/113,851, filed May 1, 2008, Coleman et al.
U.S. Appl. No. 12/114,031, filed May 2, 2008, Coleman et al.
U.S. Appl. No. 12/114,091, filed May 2, 2008, Coleman et al.
U.S. Appl. No. 12/143,020, filed Jun. 20, 2008, Ellingwood et al.
U.S. Appl. No. 10/006,400, mailed Apr. 2, 2008, Office Action.
U.S. Appl. No. 10/147,774, mailed Feb. 4, 2008, Notice of Allowance.
U.S. Appl. No. 10/147,774, mailed Jun. 30, 2008, Office Action.
U.S. Appl. No. 10/264,306, mailed May 26, 2005, Office Action.

U.S. Appl. No. 10/264,306, mailed Feb. 4, 2008, Notice of Allowance.
U.S. Appl. No. 10/264,306, mailed Jun. 27, 2008, Office Action.
U.S. Appl. No. 10/435,104, mailed Apr. 4, 2008, Notice of Allowance.
U.S. Appl. No. 10/517,004, mailed Jan. 30, 2008, Office Action.
U.S. Appl. No. 10/541,083, mailed May 5, 2008, Office Action.
U.S. Appl. No. 10/638,115, mailed Feb. 7, 2008, Office Action.
U.S. Appl. No. 10/667,144, mailed May 12, 2008, Office Action.
U.S. Appl. No. 10/682,459, mailed Apr. 2, 2008, Office Action.
U.S. Appl. No. 10/786,444, mailed Apr. 24, 2008, Office Action.
U.S. Appl. No. 10/787,073, mailed Feb. 22, 2008, Office Action.
U.S. Appl. No. 11/113,549, mailed Apr. 16, 2008, Office Action.
U.S. Appl. No. 11/152,562, mailed May 13, 2008, Office Action.
U.S. Appl. No. 11/344,891, mailed Apr. 29, 2008, Office Action.
U.S. Appl. No. 11/406,203, mailed May 23, 2008, Notice of Allowance.
U.S. Appl. No. 11/411,925, mailed Feb. 5, 2008, Office Action.
U.S. Appl. No. 60/696,069, filed Jul. 1, 2005, Pantages et al.
U.S. Appl. No. 60/946,026, filed Jun. 25, 2007, Ellingwood.
McCarthy, et al., "Tension (Stay) Suture Bridge", J. of International College of Surgeons, 34(5), pp. 613-614 (Nov. 1960). cited by other.
U.S. Appl. No. 10/006,400, mailed Jan. 2, 2009, Office Action.
U.S. Appl. No. 10/264,306, mailed Feb. 26, 2009, Office Action.
U.S. Appl. No. 10/305,923, mailed Nov. 1, 2004, Office Action.
U.S. Appl. No. 10/305,923, mailed Mar. 3, 2005, Notice of Allowance.
U.S. Appl. No. 10/435,104, mailed Nov. 14, 2007, Supplemental Notice of Allowability.
U.S. Appl. No. 10/435,104, mailed Dec. 22, 2008, Supplemental Notice of Allowability.
U.S. Appl. No. 10/517,004, mailed Aug. 13, 2008, Notice of Allowance.
U.S. Appl. No. 10/517,004, mailed Feb. 10, 2009, Notice of Allowance.
U.S. Appl. No. 10/541,083, mailed Oct. 31, 2007, Office Action.
U.S. Appl. No. 10/541,083, mailed Dec. 29, 2008, Notice of Allowance.
U.S. Appl. No. 10/638,115, mailed Oct. 29, 2008, Office Action.
U.S. Appl. No. 10/682,459, mailed Dec. 4, 2008, Office Action.
U.S. Appl. No. 10/786,444, mailed Oct. 17, 2008, Office Action.
U.S. Appl. No. 10/787,073, mailed Nov. 12, 2008, Office Action.
U.S. Appl. No. 10/908,721, mailed Nov. 25, 2008, Office Action.
U.S. Appl. No. 11/152,562, mailed Feb. 13, 2009, Office Action.
U.S. Appl. No. 11/344,793, mailed Jan. 22, 2009, Office Action.
U.S. Appl. No. 11/344,891, mailed Dec. 8, 2008, Office Action.
U.S. Appl. No. 11/344,891, mailed Feb. 26, 2009, Office Action.
U.S. Appl. No. 11/396,731, mailed Feb. 13, 2009, Office Action.
U.S. Appl. No. 11/411,925, mailed Jan. 12, 2009, Office Action.
U.S. Appl. No. 11/427,297, mailed Jan. 30, 2009, Office Action.
U.S. Appl. No. 11/461,323, mailed May 2, 2007, Office Action.
U.S. Appl. No. 11/461,323, mailed Oct. 29, 2007, Office Action.
U.S. Appl. No. 11/461,323, mailed Apr. 25, 2008, Office Action.
U.S. Appl. No. 11/461,323, mailed Nov. 6, 2008, Office Action.
U.S. Appl. No. 11/744,089, mailed Nov. 26, 2008, Office Action.
U.S. Appl. No. 12/106,928, mailed Jan. 23, 2009, Office Action.
U.S. Appl. No. 29/296,370, mailed Aug. 18, 2008, Office Action.
U.S. Appl. No. 29/296,370, mailed Dec. 2, 2008, Notice of Allowance.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
McCarthy, et al., "Tension (Stay) Suture Bridge", J. of Interntional College of Surgeons, 34(5), pp. 613-614 (Nov. 1960). cited by other.
U.S. Appl. No. 09/680,837, mailed Jul. 9, 2002, Office Action.
U.S. Appl. No. 09/680,837, mailed Nov. 6, 2002, Office Action.
U.S. Appl. No. 09/680,837, mailed Mar. 25, 2003, Office Action.
U.S. Appl. No. 09/680,837, mailed Jun. 16, 2003, Notice Of Allowance.
U.S. Appl. No. 09/680,837, mailed Sep. 11, 2003, Issue Notification.
U.S. Appl. No. 10/147,774, mailed Mar. 18, 2009, Office Action.

U.S. Appl. No. 10/541,083, mailed Apr. 16, 2009, Notice Of Allowance.
U.S. Appl. No. 10/638,115, mailed May 7, 2009, Notice Of Allowance.
U.S. Appl. No. 10/667,144, mailed Mar. 24, 2009, Office Action.
U.S. Appl. No. 10/669,313, mailed Oct. 31, 2005, Office Action.
U.S. Appl. No. 10/669,313, mailed Jan. 11, 2006, Notice Of Allowance.
U.S. Appl. No. 10/669,313, mailed Jun. 28, 2006, Notice Of Allowance.
U.S. Appl. No. 10/669,313, mailed Nov. 15, 2006, Issue Notification.
U.S. Appl. No. 10/682,459, mailed Jun. 10, 2009, Office Action.
U.S. Appl. No. 11/048,503, mailed Mar. 13, 2009, Office Action.
U.S. Appl. No. 11/344,868, mailed Mar. 25, 2009, Office Action.
U.S. Appl. No. 11/396,141, mailed May 22, 2009, Office Action.
U.S. Appl. No. 11/396,731, mailed May 22, 2009, Office Action.
U.S. Appl. No. 11/406,203, mailed Mar. 3, 2009, Office Action.
U.S. Appl. No. 11/532,325, mailed Feb. 23, 2009, Office Action.
U.S. Appl. No. 11/532,325, mailed Jun. 17, 2009, Office Action.
U.S. Appl. No. 12/106,937, mailed Mar. 30, 2009, Office Action.
U.S. Appl. No. 29/296,370, mailed Apr. 1, 2009, Notice Of Allowance.
U.S. Appl. No. 10/006,400, mailed Jul. 9, 2009, Notice of Allowance.
U.S. Appl. No. 10/264,306, mailed Aug. 13, 2009, Office Action.
U.S. Appl. No. 10/517,004, mailed Jun. 26, 2009, Notice of Allowance.
U.S. Appl. No. 10/616,832, mailed Jul. 21, 2009, Office Action.
U.S. Appl. No. 10/786,444, mailed Jun. 18, 2009, Office Action.
U.S. Appl. No. 10/787,073, mailed Aug. 13, 2009, Office Action.
U.S. Appl. No. 10/908,721, mailed Jun. 23, 2009, Office Action.
U.S. Appl. No. 11/048,503, mailed Jun. 26, 2009, Office Action.
U.S. Appl. No. 11/113,549, mailed Jul. 21, 2009, Office Action.
U.S. Appl. No. 11/152,562, mailed Jul. 6, 2009, Office Action.
U.S. Appl. No. 11/198,811, mailed Sep. 22, 2009, Office Action.
U.S. Appl. No. 11/396,141, mailed Aug. 26, 2009, Office Action.
U.S. Appl. No. 11/406,203, mailed Sep. 16, 2009, Office Action.
U.S. Appl. No. 11/411,925, mailed Sep. 10, 2009, Office Action.
U.S. Appl. No. 11/427,297, mailed Sep. 15, 2009, Office Action.
U.S. Appl. No. 11/461,323, mailed Jul. 27, 2009, Office Action.
U.S. Appl. No. 11/744,089, mailed Aug. 14, 2009, Office Action.
U.S. Appl. No. 11/958295, mailed Aug. 27, 2009, Office Action.
U.S. Appl. No. 60/693,531, filed Jun. 24, 2005, Carly.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, mailed Jan. 13, 2010, Notice of Allowance.
U.S. Appl. No. 10/147,774, mailed Oct. 26, 2009, Office Action.
U.S. Appl. No. 10/264,306, mailed Jan. 27, 2010, Office Action.
U.S. Appl. No. 10/435,104, mailed Jan. 20, 2010, Notice of Allowance.
U.S. Appl. No. 10/517,004, mailed Jan. 11, 2010, Notice of Allowance.
U.S. Appl. No. 10/541,083, mailed Feb. 5, 2010, Notice of Allowance.
U.S. Appl. No. 10/616,832, mailed Jan. 11, 2010, Notice of Allowance.
U.S. Appl. No. 10/541,083, mailed Sep. 30, 2009, Notice of Allowance.
U.S. Appl. No. 10/638,115, mailed Dec. 1, 2009, Notice of Allowance.
U.S. Appl. No. 10/638,115, mailed Apr. 2, 2010, Notice of Allowance.
U.S. Appl. No. 10/667,144, mailed Nov. 23, 2009, Office Action.
U.S. Appl. No. 10/682,459, mailed Dec. 23, 2009, Office Action.
U.S. Appl. No. 10/786,444, mailed Jan. 14, 2010, Office Action.
U.S. Appl. No. 10/787,073, mailed Feb. 17, 2010, Notice of Allowance.
U.S. Appl. No. 10/908,721, mailed Feb. 2, 2010, Office Action.
U.S. Appl. No. 11/048,503, mailed Jan. 11, 2010, Notice of Allowance.

U.S. Appl. No. 11/344,891, mailed Oct. 7, 2009, Office Action.
U.S. Appl. No. 11/455,993, mailed Feb. 17, 2009, Office Action.
U.S. Appl. No. 11/455,993, mailed Dec. 16, 2009, Office Action.
U.S. Appl. No. 11/461,323, mailed Apr. 5, 2010, Notice of Allowance.
U.S. Appl. No. 11/532,325, mailed Jan. 5, 2010, Office Action.
U.S. Appl. No. 11/532,576, mailed Mar. 1, 2010, Restriction Requirement.
U.S. Appl. No. 11/675,462, mailed Dec. 10, 2009, Office Action.
U.S. Appl. No. 11/767,818, mailed Dec. 24, 2009, Restriction Requirement.
U.S. Appl. No. 11/767,818, mailed Mar. 22, 2010, Office Action.
U.S. Appl. No. 11/959,334, mailed Aug. 19, 2009, Office Action.
U.S. Appl. No. 11/959,334, mailed Jan. 12, 2010, Notice of Allowance.
U.S. Appl. No. 12/106,937, mailed Nov. 18, 2009, Office Action.
U.S. Appl. No. 12/106,928, mailed Oct. 5, 2009, Office Action.
U.S. Appl. No. 12/402,398, mailed Mar. 9, 2010, Restriction Requirement.
U.S. Appl. No. 12/403,256, mailed Dec. 16, 2009, Restriction Requirement.
U.S. Appl. No. 29/296,370, mailed Feb. 10, 2010, Issue Notification.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 61/097,072, filed Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 10/006,400, mailed Apr. 27, 2010, Notice of Allowance.
U.S. Appl. No. 10/006,400, mailed Aug. 2, 2010, Notice of Allowance.
U.S. Appl. No. 10/147,774, mailed Jun. 8, 2010, Office Action.
U.S. Appl. No. 10/264,306, mailed Jun. 15, 2010, Office Action.
U.S. Appl. No. 10/435,104, mailed Jul. 23, 2009, Notice of Allowance.
U.S. Appl. No. 10/435,104, mailed Jun. 2, 2010, Office Action.
U.S. Appl. No. 10/517,004, mailed Apr. 23, 2010, Notice of Allowance.
U.S. Appl. No. 10/517,004, mailed Aug. 3, 2010, Notice of Allowance.
U.S. Appl. No. 10/541,083, mailed May 10, 2010, Notice of Allowance.
U.S. Appl. No. 10/616,832, mailed May 12, 2010, Notice of Allowance.
U.S. Appl. No. 10/667,144, mailed Jun. 22, 2010, Office Action.
U.S. Appl. No. 10/669,313, mailed Oct. 31, 2005, Office Action.
U.S. Appl. No. 10/682,459, mailed Apr. 28, 2010, Office Action.
U.S. Appl. No. 11/048,503, mailed Apr. 26, 2010, Notice of Allowance.
U.S. Appl. No. 11/048,503, mailed Jul. 30, 2010, Notice of Allowance.
U.S. Appl. No. 11/113,549, mailed Jul. 6, 2010, Office Action.
U.S. Appl. No. 11/152,562, mailed Mar. 31, 2010, Office Action.
U.S. Appl. No. 11/198,811, mailed Jun. 29, 2010, Notice of Allowance.
U.S. Appl. No. 11/316,775, mailed Apr. 16, 2008, Office Action.
U.S. Appl. No. 11/316,775, mailed Aug. 6, 2008, Office Action.
U.S. Appl. No. 11/344,891, mailed May 7, 2010, Office Action.
U.S. Appl. No. 11/390,586, mailed Jun. 24, 2009, Office Action.
U.S. Appl. No. 11/390,586, mailed Jul. 6, 2010, Office Action.
U.S. Appl. No. 11/396,141, mailed May 4, 2010, Office Action.
U.S. Appl. No. 11/396,731, mailed Jun. 29, 2010, Office Action.
U.S. Appl. No. 11/406,203, mailed Jun. 18, 2010, Notice of Allowance.
U.S. Appl. No. 11/508,656, mailed Dec. 9, 2009, Office Action.
U.S. Appl. No. 11/508,656, mailed Mar. 25, 2010, Office Action.
U.S. Appl. No. 11/508,662, mailed Dec. 28, 2009, Office Action.
U.S. Appl. No. 11/508,662, mailed Apr. 14, 2010, Office Action.
U.S. Appl. No. 11/508,715, mailed Jan. 6, 2010, Office Action.
U.S. Appl. No. 11/508,715, mailed Apr. 26, 2010, Office Action.
U.S. Appl. No. 11/532,576, mailed Apr. 23, 2010, Office Action.
U.S. Appl. No. 11/674,930, mailed Jan. 8, 2009, Office Action.
U.S. Appl. No. 11/674,930, mailed Jun. 4, 2009, Office Action.
U.S. Appl. No. 11/674,930, mailed Jan. 8, 2010, Office Action.
U.S. Appl. No. 11/852,190, mailed Jun. 24, 2010, Office Action.
U.S. Appl. No. 11/958,295, mailed May 25, 2010, Office Action.
U.S. Appl. No. 11/959,334, mailed Apr. 14, 2010, Notice of Allowance.
U.S. Appl. No. 11/959,334, mailed Jul. 23, 2010, Notice of Allowance.
U.S. Appl. No. 12/106,928, mailed May 10, 2010, Office Action.
U.S. Appl. No. 12/113,851, mailed Apr. 27, 2010, Office Action.
U.S. Appl. No. 12/113,851, mailed Jun. 24, 2010, Office Action.
U.S. Appl. No. 12/402,398, mailed May 20, 2010, Office Action.
U.S. Appl. No. 12/403,256, mailed Mar. 30, 2010, Office Action.
U.S. Appl. No. 12/403,277, mailed Jul. 8, 2010, Office Action.
U.S. Appl. No. 10/638,115, mailed Aug. 13, 2010, Notice of Allowance.
U.S. Appl. No. 10/541,083, mailed Aug. 17, 2010, Notice of Allowance.
U.S. Appl. No. 10/787,073, mailed Aug. 25, 2010, Notice of Allowance.
U.S. Appl. No. 12/403,256, mailed Aug. 19, 2010, Notice of Allowance.
U.S. Appl. No. 10/264,306, mailed Oct. 29, 2010, Notice of Allowance.
U.S. Appl. No. 10/435,104, mailed Oct. 5, 2010, Notice of Allowance.
U.S. Appl. No. 10/616,832, mailed Sep. 20, 2010, Notice of Allowance.
U.S. Appl. No. 10/682,459, mailed Oct. 12, 2010, Office Action.
U.S. Appl. No. 10/787,073, mailed Sep. 15, 2010, Issue Notification.
U.S. Appl. No. 11/152,562, mailed Sep. 16, 2010, Notice of Allowance.
U.S. Appl. No. 11/198,811, mailed Oct. 20, 2010, Issue Notification.
U.S. Appl. No. 11/406,203, mailed Oct. 6, 2010, Issue Notification.
U.S. Appl. No. 11/427,297, mailed Sep. 15, 2010, Office Action.
U.S. Appl. No. 11/427,309, mailed Nov. 15, 2010, Office Action.
U.S. Appl. No. 11/532,576, mailed Oct. 13, 2010, Notice of Allowance.
U.S. Appl. No. 11/675,462, mailed Aug. 31, 2010, Office Action.
U.S. Appl. No. 11/767,818, mailed Sep. 30, 2010, Office Action.
U.S. Appl. No. 11/852,190, mailed Nov. 1, 2010, Office Action.
U.S. Appl. No. 11/958,281, mailed Sep. 2, 2010, Office Action.
U.S. Appl. No. 11/958,281, mailed Oct. 8, 2010, Office Action.
U.S. Appl. No. 12/106,928, mailed Oct. 25, 2010, Office Action.
U.S. Appl. No. 12/114,031, mailed Oct. 5, 2010, Office Action.
U.S. Appl. No. 12/403,277, mailed Oct. 12, 2010, Office Action.
U.S. Appl. No. 12/114,091, mailed Oct. 27, 2010, Office Action.
U.S. Appl. No. 10/517,004, mailed Nov. 23, 2010, Issue Notification.
U.S. Appl. No. 12/114,031, mailed Nov. 22, 2010, Office Action.
U.S. Appl. No. 12/403,256, mailed Nov. 23, 2010, Issue Notification.

* cited by examiner

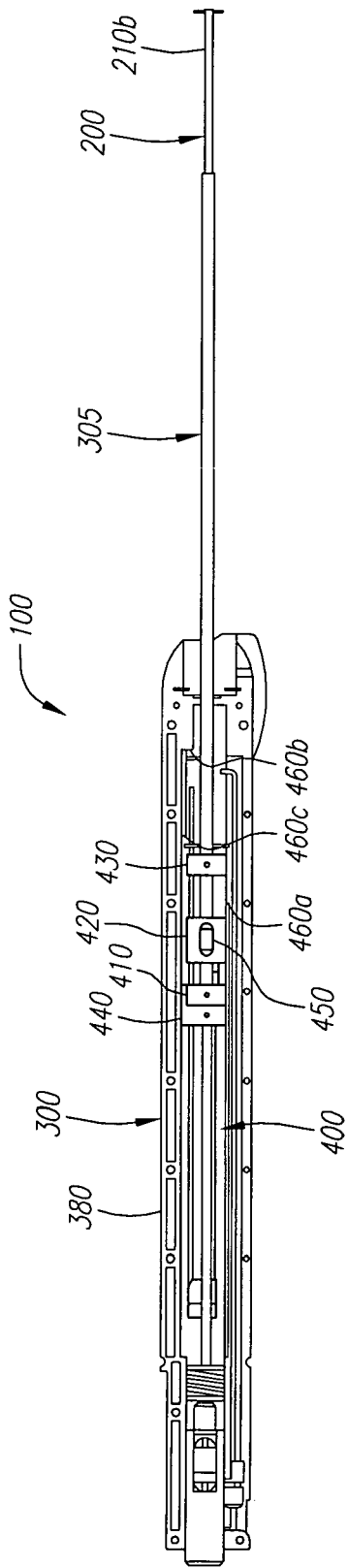
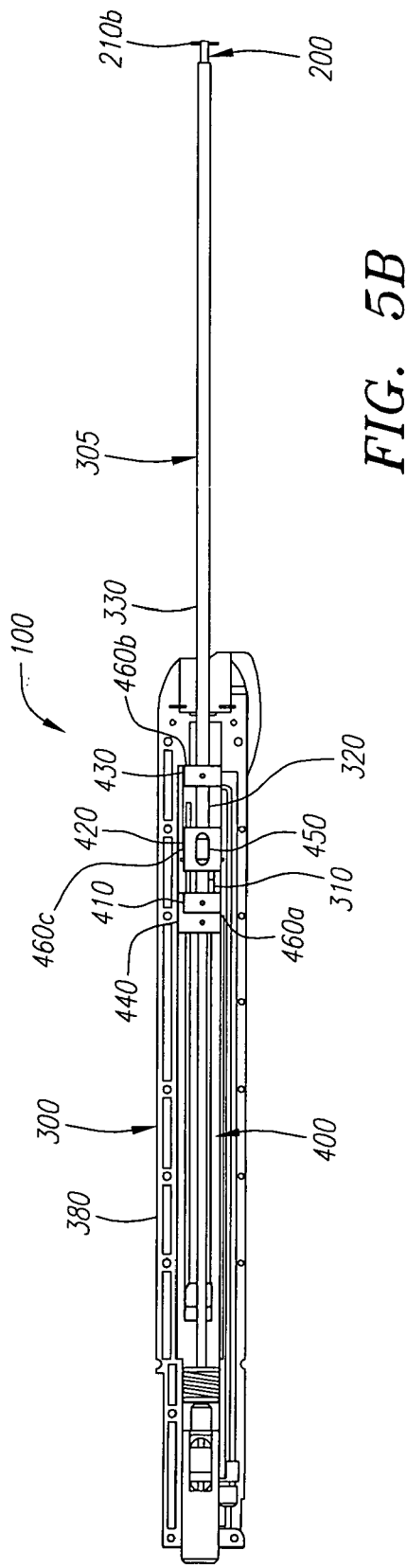

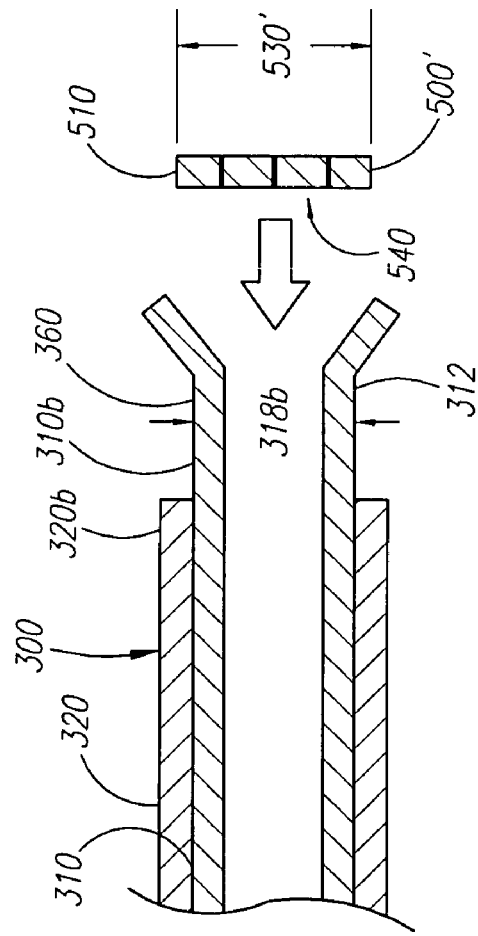
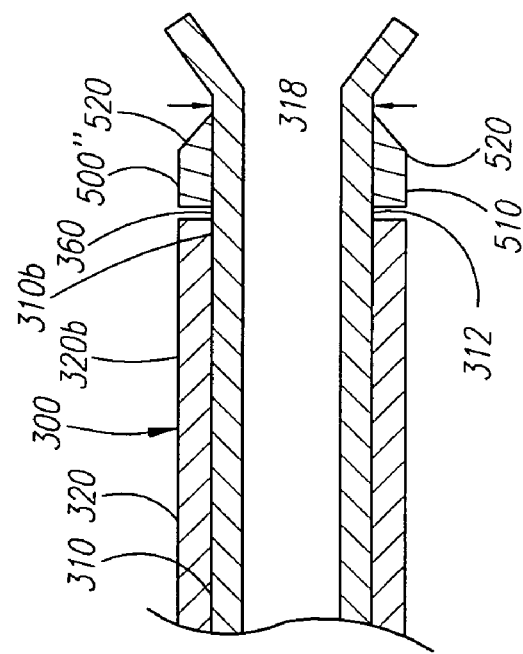
FIG. 7A
FIG. 7B

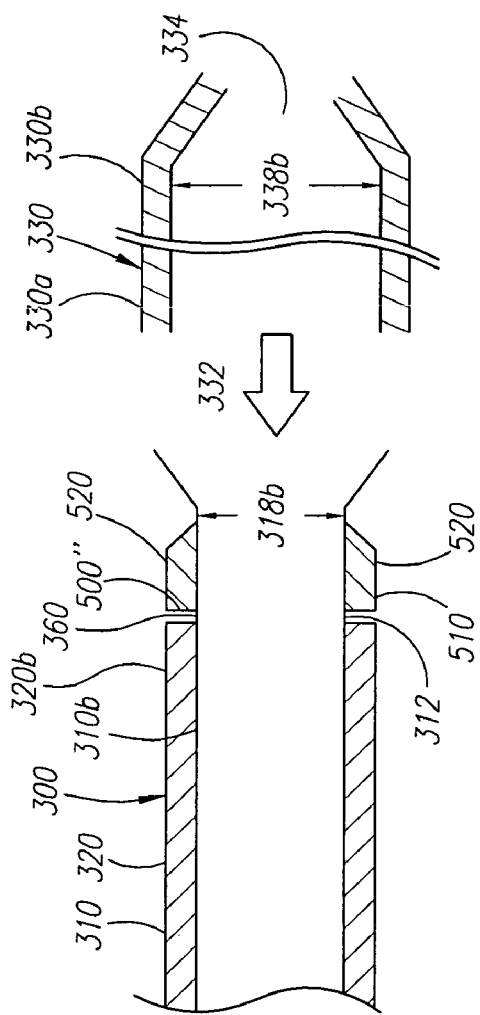
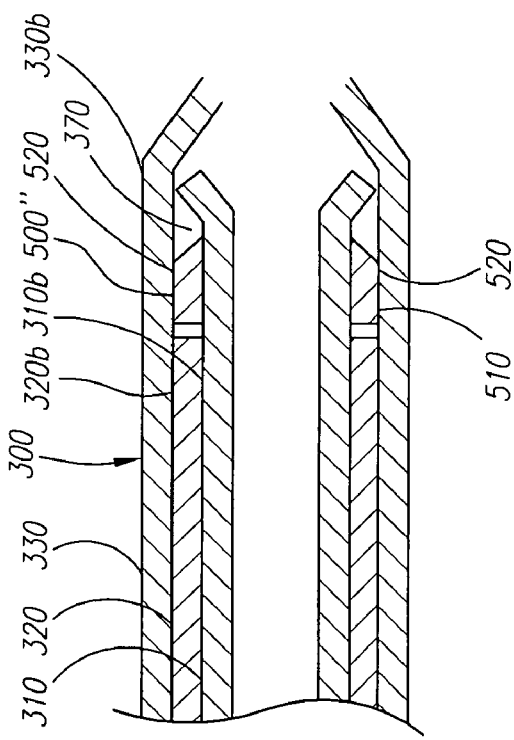
FIG. 7C
FIG. 7D

CLIP APPLIER AND METHODS OF USE

FIELD OF THE INVENTION

The present invention relates generally to apparatus and methods for closing and/or sealing openings through tissue, and more particularly to apparatus and methods for delivering a closure element for closing a puncture in a blood vessel or other body lumen formed during a diagnostic or therapeutic procedure.

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle then is removed, enabling an introducer sheath to be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For example, U.S. Pat. No. 5,676,974, issued to Kensey et al., discloses a bleed back lumen intended to facilitate positioning of a biodegradable plug within a puncture site. This device, however, requires that an anchor of the plug-be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel.

Accordingly, apparatus and methods for delivering a device for closing a vascular puncture site or other opening through tissue would be useful.

SUMMARY OF THE INVENTION

The present invention is directed toward an apparatus and method for delivering a closure element through tissue and into an opening formed in, or adjacent to, a wall of a blood vessel or other body lumen of any size.

The apparatus is configured to receive and retain the closure element such that the closure element is disposed substantially within the apparatus. Thereby, if the apparatus is introduced via an introducer sheath, for example, the closure element can be disposed within, and delivered by way of, a lumen of the introducer sheath. The apparatus also is configured to engage the blood vessel wall adjacent to the opening and to position the closure element substantially adjacent to an outer surface of the blood vessel wall adjacent to the opening.

When properly positioned, the apparatus can be activated to distally deploy the closure element. During deployment, the apparatus preferably is configured to substantially uniformly expand the closure element beyond a natural cross-section of the closure element such that the closure element, when deployed, is configured to engage significant amount of the blood vessel wall 620 and/or tissue 630. Engaging the blood vessel wall and/or tissue, the closure element is further configured to return to the natural cross-section. Thereby, the engaged blood vessel wall and/or tissue are drawn substantially closed and/or sealed, such that, for example, hemostasis within the opening is enhanced.

Other aspects and features of the present invention will become apparent from consideration of the following description taken in conjunction with the accompanying drawings.

BRIEF DESCRIPTION OF THE DRAWINGS

FIG. 5A illustrates the carrier control system of FIGS. 4A-D as the carrier assembly of FIG. 3A moves distally from an initial predetermined position.

FIG. 5B illustrates the carrier control system of FIGS. 4A-D as the carrier assembly of FIG. 3A reaches a first predetermined position.

FIG. 7A illustrates the closure element of FIGS. 6A-G prior to being disposed upon the carrier member of FIG. 3B.

FIG. 7B illustrates the closure element of FIGS. 6A-G upon being disposed upon the carrier member of FIG. 3B.

FIG. 7C illustrates the closure element of FIGS. 6A-G as the cover member of FIG. 3D receives the carrier member of FIG. 3B.

FIG. 7D illustrates the closure element of FIGS. 6A-G being retained substantially within the carrier assembly of FIG. 3A when the carrier member of FIG. 3B is disposed substantially within the cover member of FIG. 3D.

Figure 1:
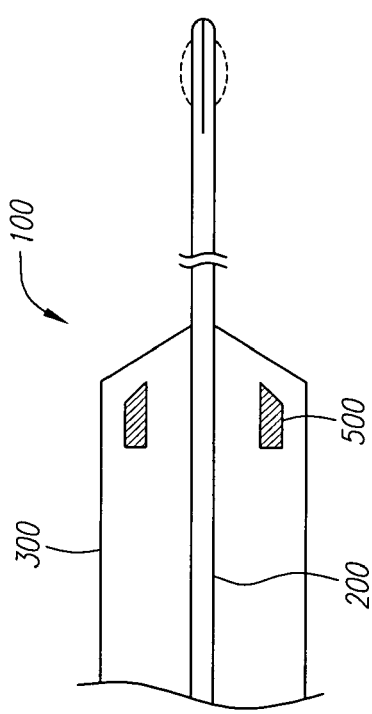
FIG. 1 provides a general illustration of an apparatus for closing openings formed in blood vessel walls in accordance with the present invention.

It should be noted that the figures are not drawn to scale and that elements of similar structures or functions are generally represented by like reference numerals for illustrative purposes throughout the figures. It also should be noted that the figures are only intended to facilitate the description of the preferred embodiments of the present invention. The figures do not describe every aspect of the present invention and do not limit the scope of the invention.

DETAILED DESCRIPTION OF THE PREFERRED EMBODIMENTS

Since current apparatuses for sealing openings formed in blood vessel walls can snag tissue adjacent to the openings during positioning and may not provide an adequate seal, an apparatus that is configured to prevent inadvertent tissue contact during positioning and to engage a substantial of amount of tissue adjacent to the opening can prove much more desirable and provide a basis for a wide range of medical applications, such as diagnostic and/or therapeutic procedures involving blood vessels or other body lumens of any size. This result can be achieved, according to one embodiment of the present invention, by employing an apparatus 100 as shown in FIG. 1.

Figure 6A:
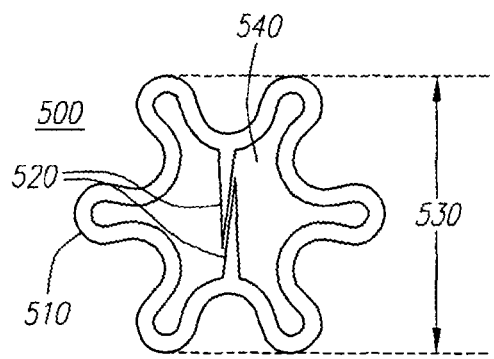
FIG. 6A illustrates a top view of one embodiment of a closure element in a natural, planar configuration and with a natural cross-section for use with the apparatus of FIG. 1.
Figure 6B:
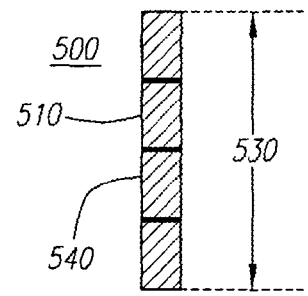
FIG. 6B illustrates a side view of the closure element of FIG. 6A.
Figure 6C:
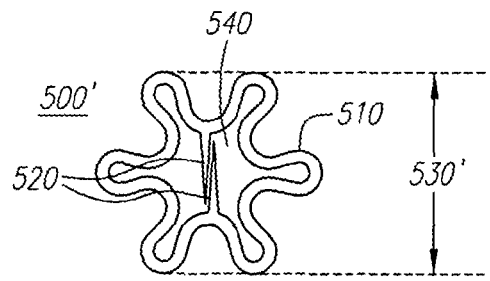
FIG. 6C illustrates a top view of the closure element of FIGS. 6A-B after a natural cross-section of the closure element has been reduced.
Figure 6D:
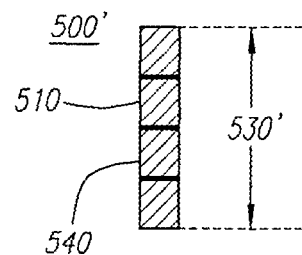
FIG. 6D illustrates a side view of the reduced closure element of FIG. 6C.
Figure 6E:
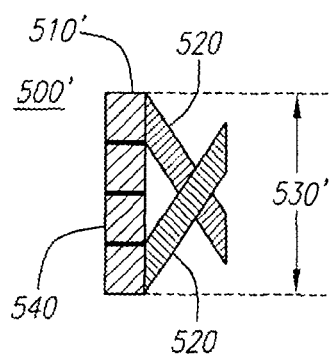
FIG. 6E illustrates a side view of the reduced closure element of FIGS. 6C-D as the reduced closure element transitions from the natural, planar configuration to a tubular configuration.
Figure 6F:
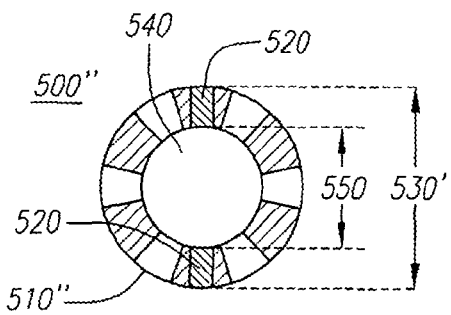
FIG. 6F illustrates a top view of the closure element of FIGS. 6C-D upon completing the transition from the natural, planar configuration to a substantially tubular configuration.

As will be discussed in more detail below, the apparatus 100 can deliver a closure element 500 (shown in FIGS. 6A-B) through tissue 630 (shown in FIG. 8A) and into an opening 610 (shown in FIG. 8A) formed in and/or adjacent to a wall 620 (shown in FIG. 8A) of a blood vessel 600 (shown in FIG. 8A) or other body lumen. The closure element (or clip) 500 preferably has a generally annular-shape body 510 (shown in FIGS. 6A-B) defining a channel 540 and one or more barbs and/or tines 520 (shown in FIGS. 6A-B) for receiving and engaging the blood vessel wall 620 and/or the tissue 630 around the opening 610. Although the closure element 500 has a natural shape and size, the closure element 500 can be deformed into other shapes and sizes, as desired, and is configured to return to the natural shape and size when released. For example, the closure element 500 can have a natural, planar configuration with opposing tines 520 and a natural cross-section 530 as shown in FIGS. 6A-B. The natural cross-section 530 of the closure element 500 can be reduced to form a reduced closure element 500' that has a natural, planar configuration with opposing tines 520 and a reduced cross-section 530' as shown in FIGS. 6C-D. By rotating the opposing tines 520 axially as shown in FIG. 6E, the reduced closure element 500' can be further deformed to form a substantially tubular closure element 500" (shown in FIG. 6F) having the reduced cross-section 530' as well as being in a substantially tubular configuration with the tines 520 in an axial configuration.

Being configured to draw the blood vessel wall 620 and/or the tissue 630 adjacent to the opening 610 substantially closed and/or to enhance hemostasis within the opening 610, the closure element 500 can be formed from any suitable material, including any biodegradable material, any shape memory alloy, such as alloys of nickel-titanium, or any combination thereof. As desired, the closure element 500 can include radiopaque markers (not shown) or may be wholly or partially formed from a radiopaque material to facilitate observation of the closure element 500 using fluoroscopy or other imaging systems. Exemplary embodiments of a closure element are disclosed in U.S. Pat. No. 6,197,042, in co-pending application Ser. Nos. 09/546,998, 09/610,238, and 10/081,726. The disclosures of these references and any others cited therein are expressly incorporated herein by reference.

The apparatus 100 is configured to receive and retain the closure element 500 such that the closure element 500 is disposed substantially within the apparatus 100. Thereby, if the apparatus 100 is introduced via an introducer sheath 640 (shown in FIG. 8A), for example, the closure element 500 can be disposed within, and delivered by way of, a lumen 644 (shown in FIG. 8A) of the introducer sheath 640. The apparatus 100 also is configured to engage the blood vessel wall 620 adjacent to the opening 610. Being disposed substantially within the apparatus 100, the closure element 500 can deeply penetrate, without inadvertently contacting, tissue 630 adjacent to the opening 610 such that the apparatus 100 can position the closure element 500 substantially adjacent to an outer surface 620a (shown in FIG. 8A) of the blood vessel wall 620 adjacent to the opening 610.

When properly positioned, the apparatus 100 can be activated to distally deploy the closure element 500. Although preferably configured to substantially uniformly expand the closure element 500 beyond the natural cross-section 530 of the closure element 500 during deployment, the apparatus 100, as desired, can deploy the closure element 500 without expanding the closure element 500. The closure element 500, when deployed, is configured to engage significant amount of the blood vessel wall 620 and/or tissue 630 adjacent to the opening 610. Engaging the blood vessel wall 620 and/or tissue 630, the closure element 500 is further configured to return to the natural cross-section 530. Thus, the engaged blood vessel wall 620 and/or tissue 630 are drawn substantially closed and/or sealed, such that, for example, hemostasis within the opening 610 is enhanced.

The apparatus 100 can be provided as via one or more integrated components and/or discrete components. As shown in FIG. 1, for example, the apparatus 100 can comprise a locator (or obturator) assembly 200 and a carrier assembly 300. For purposes of illustration, the locator assembly 200 and the carrier assembly 300 are shown in FIG. 1 as comprising substantially separate assemblies. As desired, however, the locator assembly 200 and the carrier assembly 300 each can be provided, in whole or in part, as one or more integrated assemblies.

Figure 2A:
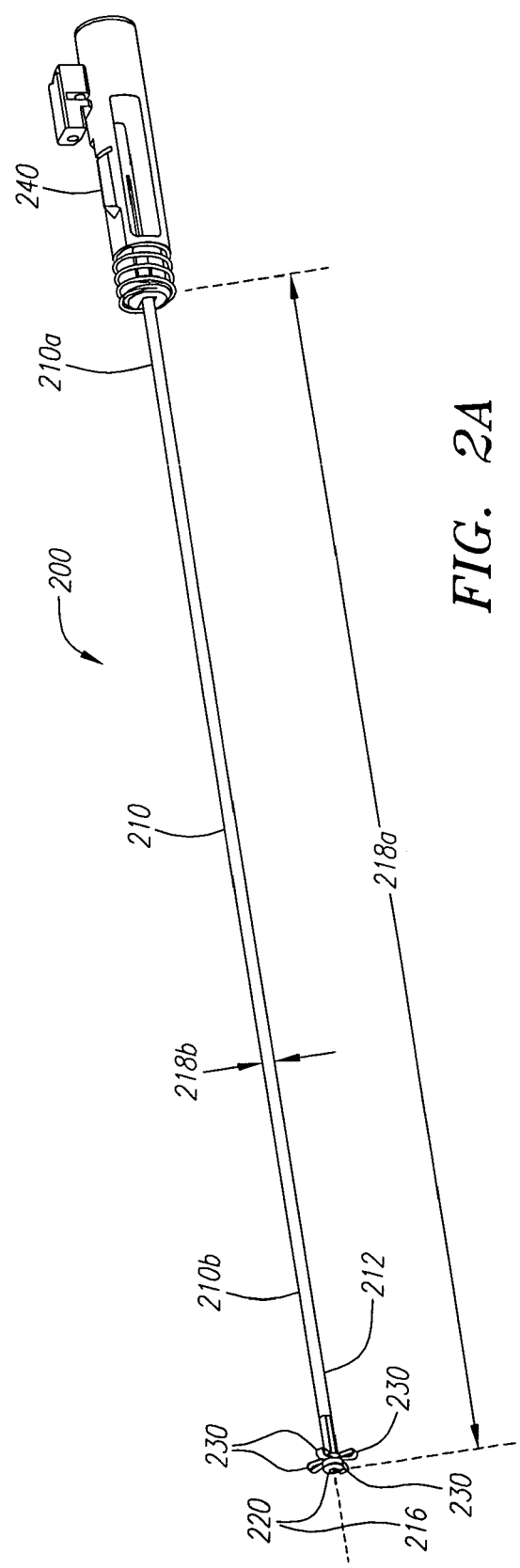
FIG. 2A illustrates one embodiment of a locator assembly for the apparatus of FIG. 1.

Being configured to extend into the opening 610, the locator assembly 200 can selectably engage the inner surface 620b of the blood vessel wall 620 adjacent to the opening 610. Thereby, the locator assembly 200 is configured to draw the blood vessel wall 620 taut and can maintain the proper position of the apparatus 100 as the blood vessel 600 pulsates. The locator assembly 200 can be provided in the manner disclosed in co-pending application Ser. Nos. 09/732,835 and 10/081,723, the disclosure of which is expressly incorporated herein by reference, and preferably includes a flexible or semi-rigid tubular body 210, such as an elongate rail, with a longitudinal axis 216. As illustrated in FIG. 2A, the tubular body 210 has a proximal end region 210a and a distal end region 210b and includes a predetermined length 218a and a predetermined outer cross-section 218b, both of which can be of any suitable dimension. The distal end region 210b of the locator assembly 200 preferably includes a substantially rounded, soft, and/or flexible distal end or tip 220 to facilitate atraumatic advancement and/or retraction of the distal end region 210b into the blood vessel 600. As desired, a pigtail (not shown) may be provided on the distal end 220 to further aid atraumatic advancement of the distal end region 210b.

The distal end region 210b of the locator assembly 200 further is selectably controllable between an unexpanded state and an expanded state. In the unexpanded state, the distal end region 210b has an unexpanded size; whereas, the distal end region 210b in the expanded state has an expanded size, which is greater than the unexpanded size of the distal end region 210b in the unexpanded state. The distal end region 210b is configured to expand from the unexpanded size to the expanded size and/or to contract from the expanded size to the unexpanded size, and the expansion and contraction of the distal end region 210b preferably is substantially uniform about the longitudinal axis 216. For example, one or more expansion elements 230 can be provided on the distal end region 210b and can be configured to expand substantially transversely with respect to a longitudinal axis 216 of the locator assembly 200. Preferably being substantially equally distributed about an outer periphery 212 of the distal end region 210b, the expansion elements 230 may include radiopaque markers (not shown) or may be wholly or partially formed from a radiopaque material to facilitate observation of the expansion elements 230 and/or the distal end region 210b using fluoroscopy or other imaging systems.

Figure 2B:
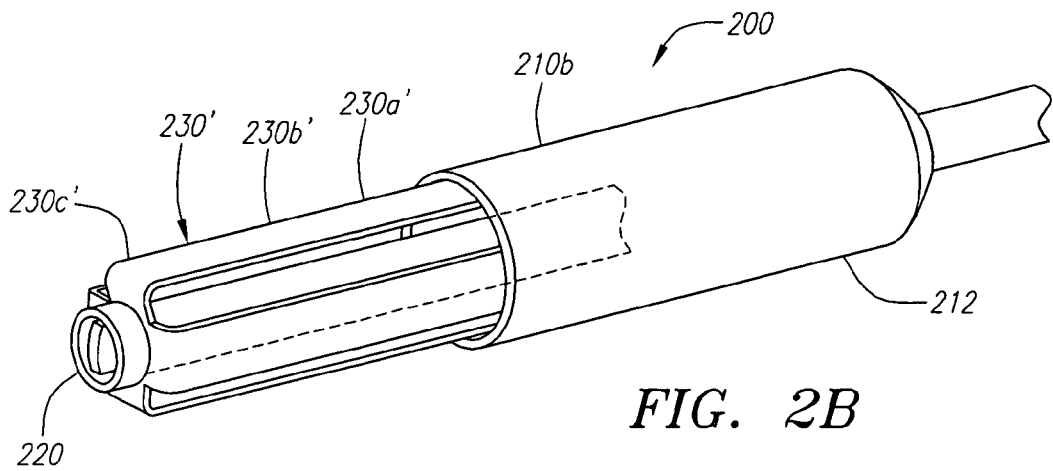
FIG. 2B illustrates one embodiment of a distal end region of the locator assembly of FIG. 2A when the distal end region is in an unexpanded state.
Figure 2C:
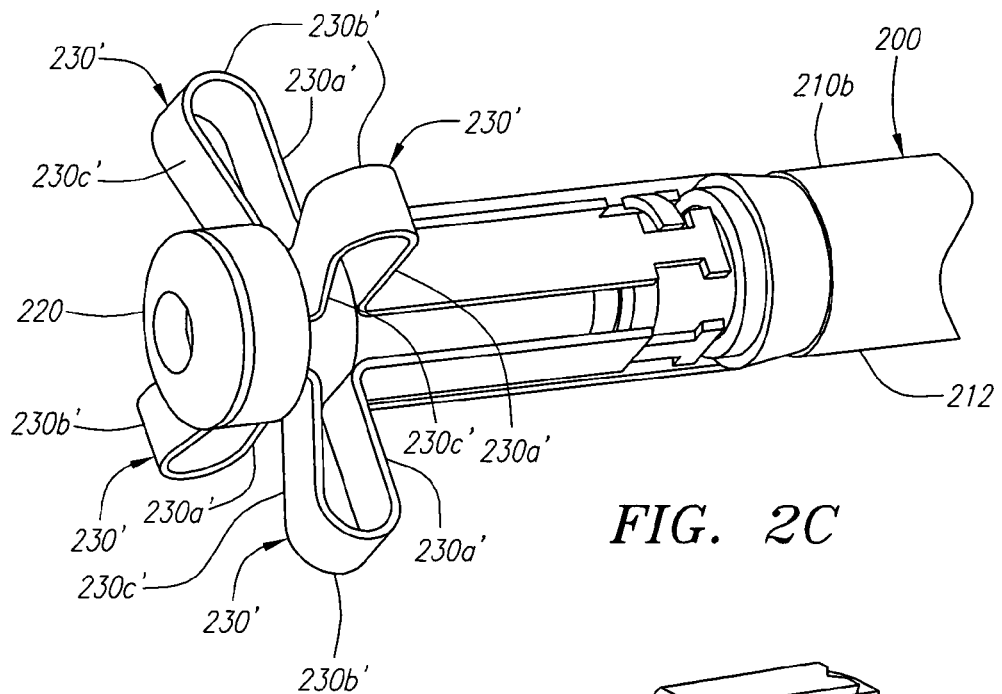
FIG. 2C illustrates the distal end region of the locator assembly of FIG. 2B when the distal end region is in an expanded state.

At least one, and preferably all, of the expansion elements 230 can comprise a substantially flexible member 230' with a substantially fixed end region 230a', an intermediate region 230b', and a movable end region 230c' as shown in FIGS. 2B-C. For each substantially flexible member 230', the fixed end region 230a' is fixedly coupled with the distal end region 210b; whereas, the movable end region 230c' is movably coupled with the distal end region 210b and configured to be axially movable relative to the fixed end region 230a'. When each movable end region 230c' is axially moved toward the relevant fixed end region 230a', the intermediate regions 230b' buckle and/or expand transversely outwardly, thereby transitioning the distal end region 210b of the locator assembly 200 from the unexpanded state to the expanded state. In contrast, the distal end region 210b transitions from the expanded state to the unexpanded state as each of the movable end regions 230c' are axially moved away from the relevant fixed end region 230a'. Although the expansion elements 230 are shown as comprising the flexible members 230' in FIGS. 2B-C for purposes of illustration, it is understood that the expansion elements 230 can comprise any type of expansion elements and are not limited to the illustrated embodiments.

Figure 2D:
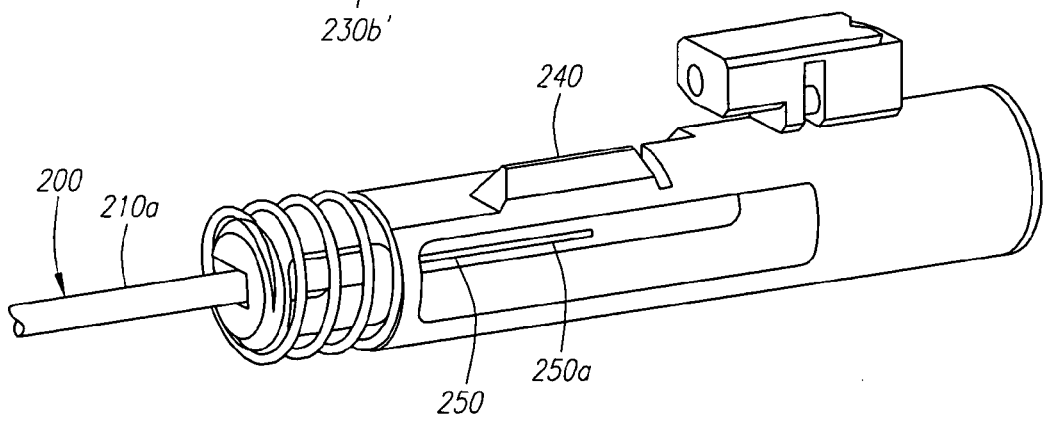
FIG. 2D illustrates one embodiment of a proximal end region of the locator assembly of FIG. 2A.

Turning to FIG. 2D, the locator assembly 200 also can include a locator control system 240 that is coupled with the proximal end region 210a of the locator assembly 200 and that is configured to selectively control the distal end region 210b of the locator assembly 200 between the unexpanded and expanded states. The locator control system 240 can selectively control the distal end region 210b between the unexpanded and expanded states, such as by being activated by a switching system (not shown). For example, a control member 250, such as a rod, wire, or other elongate member, can be moveably disposed within a lumen (not shown) formed by the tubular body 210 and extending substantially between the proximal end region 210a and the distal end region 210b. The control member 250 has a proximal end region 250a that is coupled with the locator control system 240, preferably via a control block 260 (shown in FIG. 4D), and a distal end region (not shown) that is coupled with the distal end region 210b of the locator assembly 200, the expansion elements 230, and/or the movable end regions 230c' of the substantially flexible members 230'. The locator control system 240 can selectively transition the distal end region 210b, the expansion elements 230, and/or the substantially flexible members 230' between the unexpanded and expanded states by moving the control member 250 axially relative to the tubular body 210.

The locator control system 240 preferably includes a locator release system 490 for maintaining the unexpanded state and/or the expanded state of the distal end region 210b, the expansion elements 230, and/or the substantially flexible members 230'. Preferably being configured to maintain the expanded state of the distal end region 210b, the locator release system 490 can comprise any type of locking system and can be engaged, for instance, by activating the switching system. For example, once the substantially flexible members 230' have entered the expanded state, the locator release system 490 can secure the control member 250 to prevent axial movement relative to the tubular body 210, thereby maintaining the substantially flexible members 230' in the expanded state.

In the manner described in more detail below, the locator control system 240 also can be configured to disengage the locator release system 490, such that the distal end region 210b, the expansion elements 230, and/or the substantially flexible members 230' can transition between the unexpanded and expanded states. The locator release system 490 can be disengaged, for example, by activating an emergency release system (not shown). As desired, the locator control system 240 can further include a biasing system (not shown), such as one or more springs, to bias the distal end region 210b, the expansion elements 230, and/or the substantially flexible members 230' to enter and/or maintain the unexpanded state when the locator release system 490 is disengaged.

Returning to FIG. 1, the carrier assembly 300 is coupled with, and slidable relative to, the locator assembly 200. The carrier assembly 300 is configured to receive and retain the closure element 500 (shown in FIGS. 6A-B), which preferably is disposed substantially within the carrier assembly 300. When the locator assembly 200 engages the inner surface 620b (shown in FIG. 8A) of the blood vessel wall 620 (shown in FIG. 8A), the carrier assembly 300 is further configured to position the closure element 500 substantially adjacent to the opening 610 (shown in FIG. 8A) and to deploy the closure element 500. Upon being deployed, the closure element 500 can maintain the reduced cross-section 530' (shown in FIGS. 6C-D) but preferably can temporarily and substantially uniformly expand beyond the natural cross-section 530 (shown in FIGS. 6A-B) of the closure element 500. In either case, the closure element 500, when deployed, can engage significant amount of the blood vessel wall 620 and/or tissue 630 adjacent to the opening 610. Thereafter, the closure element 500 is configured to return to the natural cross-section 530, preferably substantially uniformly, such that the blood vessel wall 620 and/or tissue 630 is drawn substantially closed and/or sealed.

Figure 3A:
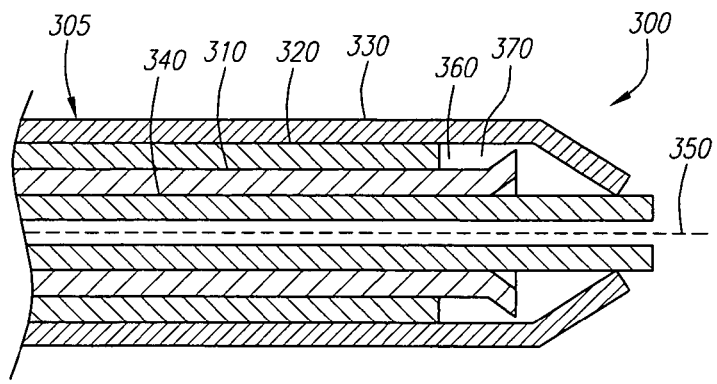
FIG. 3A illustrates one embodiment of a carrier assembly for the apparatus of FIG. 1.
Figure 6G:
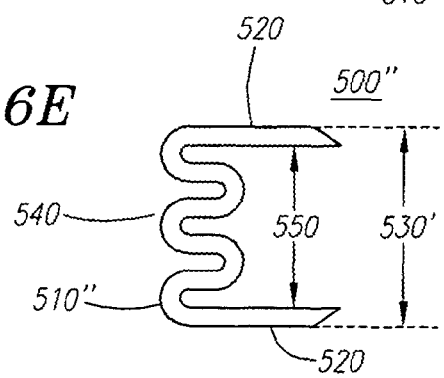
FIG. 6G illustrates a side view of the closure element of FIG. 6F.

Turning to FIGS. 3A-D, the carrier assembly 300 can include a tube set 305, comprising a carrier member 310, a pusher member 320, and a cover member 330. The carrier member 310, the pusher member 320, and the cover member 330 can be provided as a plurality of nested, telescoping members with a common longitudinal axis 350 as illustrated in FIG. 3A. The carrier member 310 is configured to receive and support the closure element 500. While being disposed on the carrier member 310, the closure element 500 preferably is deformed from the natural, planar configuration to form the substantially tubular closure element 500'' (shown in FIGS. 6F-G) as will be discussed in more detail below. Being disposed substantially about, and supported by, an outer periphery 312b of the carrier member 310, the substantially tubular closure element 500'' can be substantially in axial alignment with the carrier member 310 with the tines 520 pointed substantially distally.

Figure 3B:
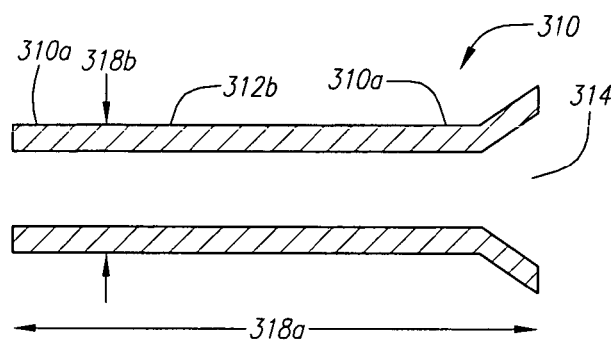
FIG. 3B illustrates one embodiment of a carrier member for the carrier assembly of FIG. 3A.

Preferably being formed as a substantially rigid, semi-rigid, or flexible tubular member, the carrier member 310 has a proximal end region 310a and a distal end region 310b and includes a predetermined length 318a and a predetermined cross-section 318b, both of which can be of any suitable dimension. The carrier member 310 also can define a lumen 314 that extends substantially between the proximal end region 310a and the distal end region 310b and that is configured to slidably receive at least a portion of the tubular body 210 of the locator assembly 200. Although the cross-section 318b of the carrier member 310 generally is substantially uniform, the distal end region 310b of the carrier member 310 preferably has a cross-section that increases distally, as illustrated in FIGS. 3A-B, for substantially uniformly expanding the substantially tubular closure element 500'' beyond the natural cross-section 530 of the closure element 500 when the substantially tubular closure element 500'' is deployed. To deploy the closure element 500 without expanding the closure element 500, the distal end region 310b can be formed with a cross-section (not shown) that is substantially uniform. Although shown and described as having the cross-section that increases distally for expanding the substantially tubular closure element 500'', it will be understood that the distal end region 310b of the carrier member 310 can be provided with the substantially-uniform cross-section and that the substantially tubular closure element 500'' can be deployed without being expanded.

Being configured to distally deploy the substantially tubular closure element 500'', the pusher member 320 has a proximal end region 320a and a distal end region 320b and is coupled with, and slidable relative to, the carrier member 310. The pusher member 320 includes a predetermined length 328a and a predetermined cross-section 328b, both of which can be of any suitable dimension and can be configured to slidably receive the carrier member 310 such that the distal end region 320b of the pusher member 320 is offset proximally from the distal end region 310b of the carrier member 310. As desired, the predetermined length 328a of the pusher member 320 can be greater than or substantially equal to the predetermined length 318a of the carrier member 310. The predetermined length 328a of the pusher member 320 however preferably is less than the predetermined length 318a of the carrier member 310 such that the carrier member 310 and the pusher member 320 at least partially define a space 360 distal to the distal end region 320b of the pusher member 320 and along the periphery 312b of the carrier member 310.

Figure 3C:
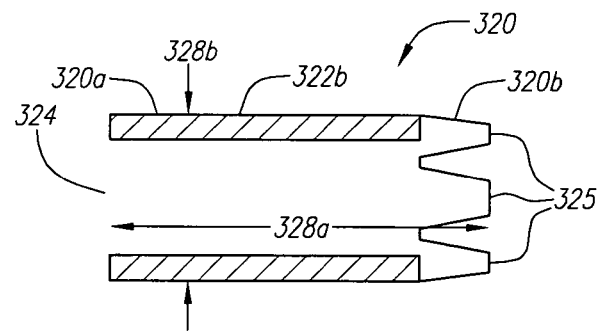
FIG. 3C illustrates one embodiment of a pusher member for the carrier assembly of FIG. 3A.

Being formed from a substantially rigid, semi-rigid, or flexible material, the pusher member 320 preferably is substantially tubular and can define a lumen 324 that extends substantially between the proximal end region 320a and the distal end region 320b and that is configured to slidably receive at least a portion of the carrier member 310. The cross-section 328b of the pusher member 320 preferably is substantially uniform, and the distal end region 320b of the pusher member 320 can comprise one or more longitudinal extensions 325, which extend distally from the pusher member 320 and along the periphery 312b of the carrier member 310 as shown in FIG. 3C. The longitudinal extensions 325 preferably are biased such that the longitudinal extensions 325 extend generally in parallel with common longitudinal axis 350. The longitudinal extensions 325 are sufficiently flexible to expand radially, and yet sufficiently rigid to inhibit buckling, as the distal end region 320b is directed distally along the carrier member 310 and engage the distally-increasing cross-section of the distal end region 310b of the carrier member 310 to deploy the substantially tubular closure element 500".

The cover member 330 is configured to retain the substantially tubular closure element 500" substantially within the carrier assembly 300 prior to deployment. Being coupled with, and slidable relative to, the pusher member 320, the cover member 330 has a proximal end region 330a and a distal end region 330b and includes a predetermined length 338a and a predetermined cross-section 338b, both of which can be of any suitable dimension. Preferably being formed as a substantially rigid, semi-rigid, or flexible tubular member, the cover member 330 has an inner periphery 332a and an outer periphery 332b and can define a lumen 334. The lumen 334 extends substantially between the proximal and distal end regions 330a, 330b of the cover member 330 and can be configured to slidably receive at least a portion of the pusher member 320. When the cover member 330 is properly positioned within the carrier assembly 300, the distal end region 330b is configured to extend over the space 360, thereby defining an annular cavity 370 for receiving and retaining the substantially tubular closure element 500".

Figure 3D:
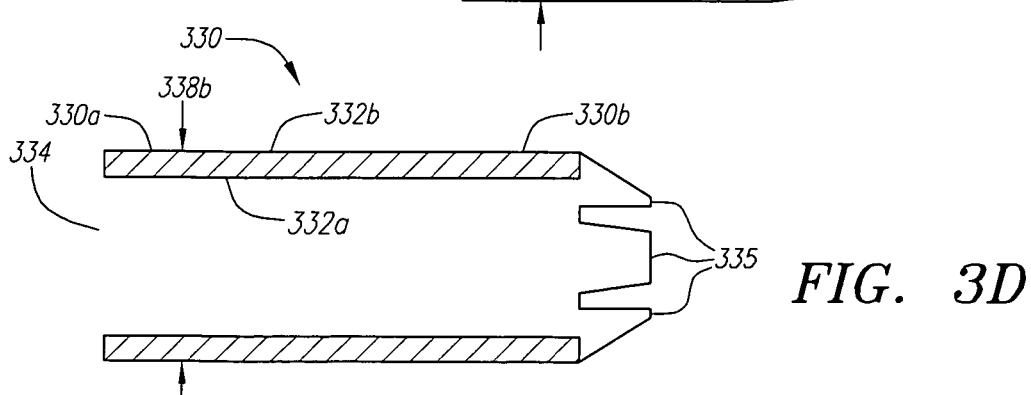
FIG. 3D illustrates one embodiment of a cover member for the carrier assembly of FIG. 3A.

The cross-section 338b of the cover member 330 preferably is substantially uniform, and the distal end region 330b of the cover member 330 preferably comprises one or more longitudinal extensions 335, which extend distally from the cover member 330 and along an outer periphery 322b of the pusher member 320 as shown in FIG. 3D. Although the longitudinal extensions 335 can extend generally in parallel with common longitudinal axis 350, the longitudinal extensions 335 preferably are biased such that the plurality of longitudinal extensions 335 extend substantially radially inwardly as illustrated in FIGS. 3A and 3D. Thereby, the longitudinal extensions 335 can at least partially close the lumen 334 substantially adjacent to the distal end region 330b of the cover member 330. To permit the substantially tubular closure element 500" to be deployed from the annular cavity 370, the longitudinal extensions 335 preferably are sufficiently flexible to expand radially to permit the distal end region 310b of the carrier member 310 to move distally past the cover member 330 to open the annular cavity 370 such that the distal end region 330b no longer extends over the space 360.

If the carrier assembly 300 is assembled as the plurality of nested, telescoping members as shown in FIG. 3A, the carrier member 310 is at least partially disposed within, and slidable relative to, the lumen 324 of the pusher member 320. The pusher member 320, in turn, is at least partially disposed within, and slidable relative to, the lumen 334 of the cover member 330. To couple the carrier assembly 300 with the locator assembly 200, the tubular body 210 of the locator assembly 200 is at least partially disposed within, and slidable relative to, the lumen 314 of the carrier member 310. The longitudinal axis 216 of the locator assembly 200 preferably is substantially in axial alignment with the common longitudinal axis 350 of the carrier member 310, the pusher member 320, and the cover member 330.

Figure 3E:
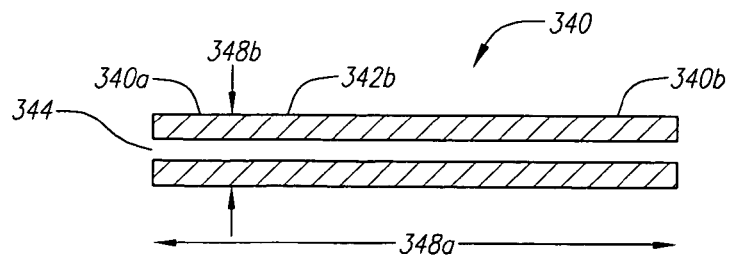
FIG. 3E illustrates one embodiment of a support member for the carrier assembly of FIG. 3A.

It will be appreciated that the tube set 305 preferably also includes a support member 340 as shown in FIGS. 3A and 3E. The support member 340 is configured to slidably receive the tubular body 210 of the locator assembly 200 and to provide radial support for the distal end region 210b of the tubular body 210 when the locator assembly 200 is coupled with the carrier assembly 300. The carrier assembly 300 can advantageously include the support member 340, for example, if the tubular body 210 is not sufficiently rigid or under other circumstances in which support for the tubular body 210 might be desirable. It also will be appreciated that the support member 340 also can be configured to inhibit the plurality of longitudinal extensions 335, which extend from the distal end region 330b of the cover member 330, from expanding prematurely when the closure element 500 is deployed.

Preferably being formed as a substantially rigid, semi-rigid, or flexible tubular member, the support member 340 includes a proximal end region 340a and a distal end region 340b. Having an outer periphery 342b, the support member 340 can define a lumen 344 that extends substantially between the proximal end region 340a and the distal end region 340b and that is configured to slidably receive and support at least a portion of the tubular body 210 of the locator assembly 200. The support member 340, in turn, can be at least partially slidably disposed within the lumen 314 of the carrier member 310 such that the tubular body 210 of the locator assembly 200 is coupled with, and slidable relative to, the carrier member 310 in the manner described in more detail above. The support member 340 has a predetermined length 348a and a predetermined cross-section 348b, both of which can be of any suitable dimension, and the cross-section 348b preferably is substantially uniform. Although shown and described as being substantially separate for purposes of illustration, it will be appreciated that the carrier member 310, the pusher member 320, the cover member 330, and/or the support member 340 can be provided, in whole or in part, as one or more integrated assemblies.

Figure 4A:
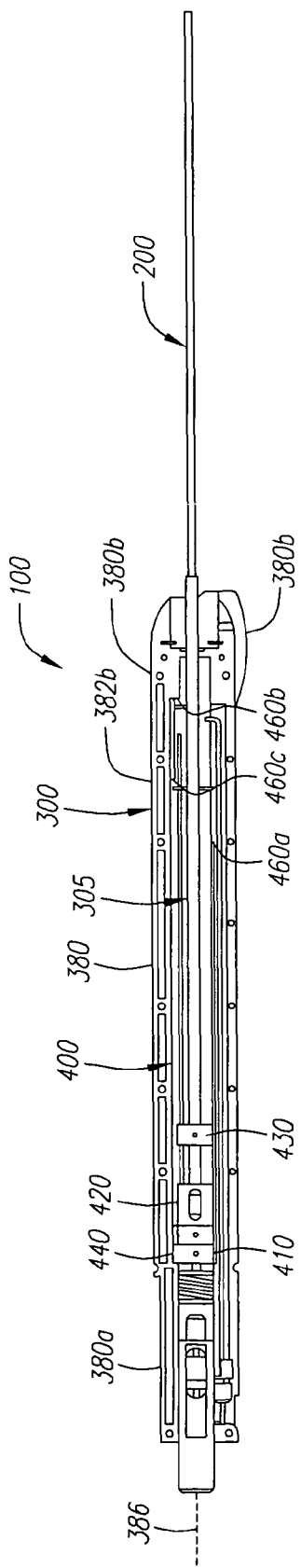
FIG. 4A illustrates a cross-sectional side view of one embodiment of a triggering system for the carrier assembly of FIG. 3A.

The carrier assembly 300 also can include a housing 380 as illustrated in FIG. 4A. Preferably being formed as an elongate member with a longitudinal axis 386, the housing 380 has an outer periphery 382b and includes a proximal end region 380a and a distal end region 380b. Thereby, when the apparatus 100 is properly assembled, the tubular body 210 of the locator assembly 200 at least partially disposed within, and slidable relative to, the tube set 305 such that the distal end region 210b of the tubular body 210 extends beyond the distal end regions 310b, 320b, 330b, and/or 340b. The tubular body 210, the carrier member 310, the pusher member 320, the cover member 330, and, if provided, the support member 340 are at least partially disposed within, and slidable relative to, the housing 380, and the respective distal end regions 210b, 310b, 320b, 330b, and 340b extend from the distal end region 380b of the housing 380 such that the common longitudinal axis 350 (shown in FIG. 3A) of the tube set 305 is substantially axially aligned with the longitudinal axis 386 of the housing 380. Being configured to slidably retain the respective proximal end regions 210a, 310a, 320a, 330a, and 340a, the housing 380 supports the tube set 305 and can have one or more handles 390 to facilitate use of the apparatus 100. The handles 390 extend substantially radially from the outer periphery 382b of the housing 380 and can be provided in the manner known in the art.

When the apparatus 100 is properly assembled, the tubular body 210 of the locator assembly 200 is at least partially disposed within, and slidable relative to, the tube set 305 of the carrier assembly 300 such that the distal end region 210b of the tubular body 210 extends beyond the distal end regions 310b, 320b, 330b, and/or 340b. Further, the proximal end region 210a of the tubular body 210 and the proximal end regions 310a, 320a, 330a, and/or 340a of the tube set 305 are at least partially disposed within, and slidable relative to, the housing 380. The switching system of the locator assembly 200 and a switching system 450 of the triggering system 400 preferably are accessible external to the housing 380 as shown in FIG. 4A.

Figure 4B:
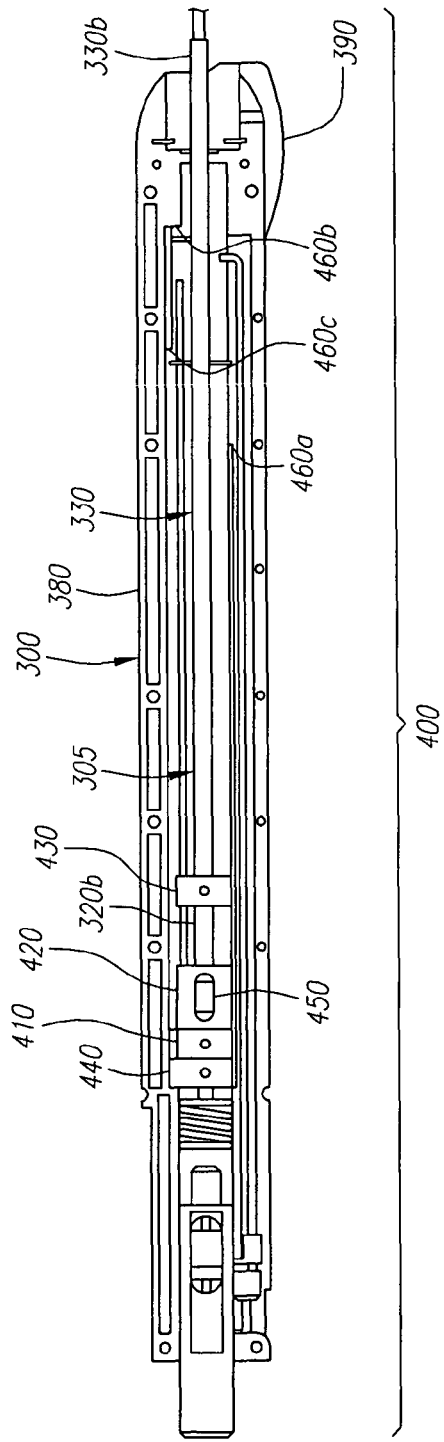
FIG. 4B illustrates a first detailed cross-sectional side view of the triggering system of FIG. 4A.
Figure 4C:
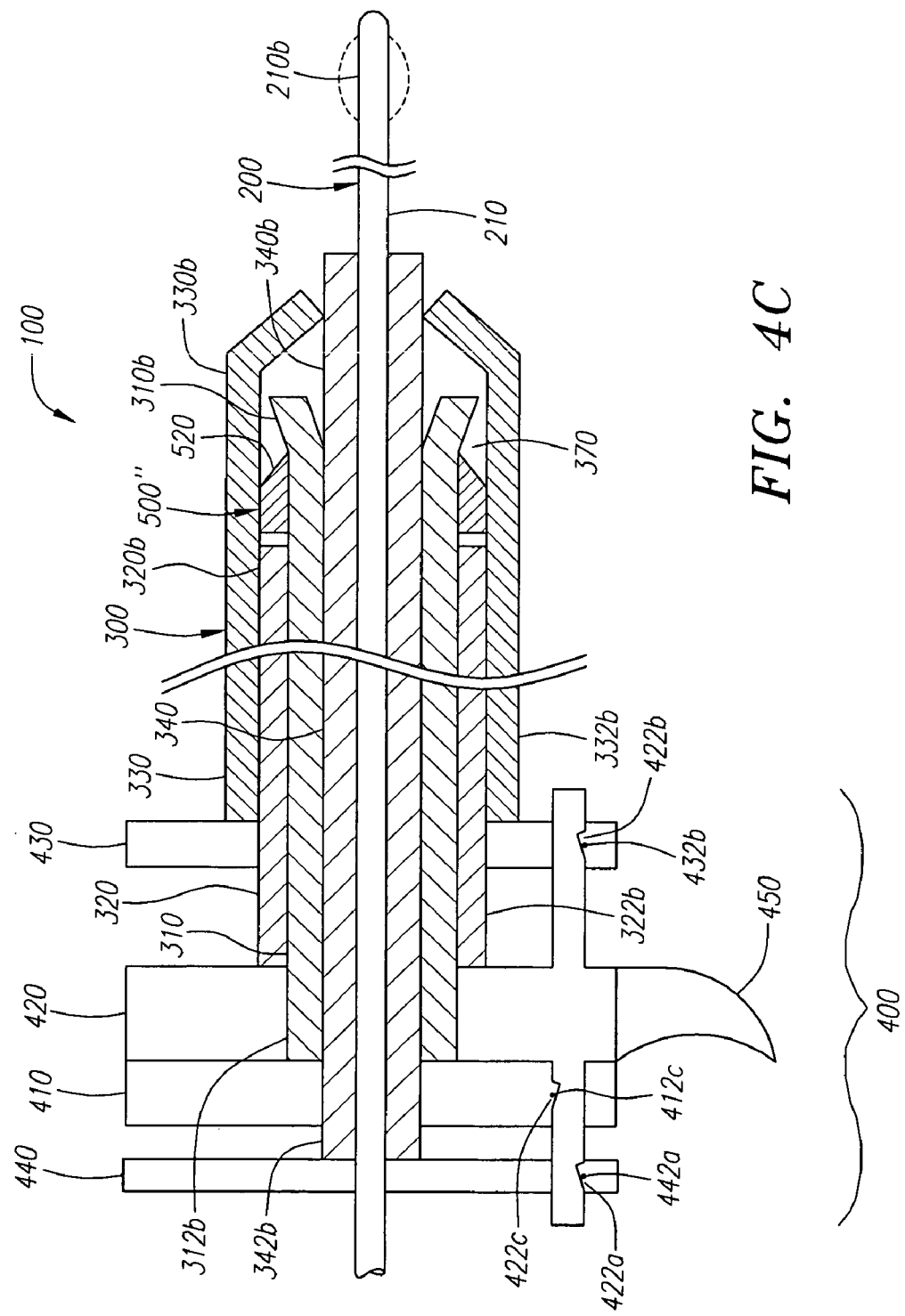
FIG. 4C illustrates a detailed view of the triggering system of FIG. 4B.
Figure 4D:
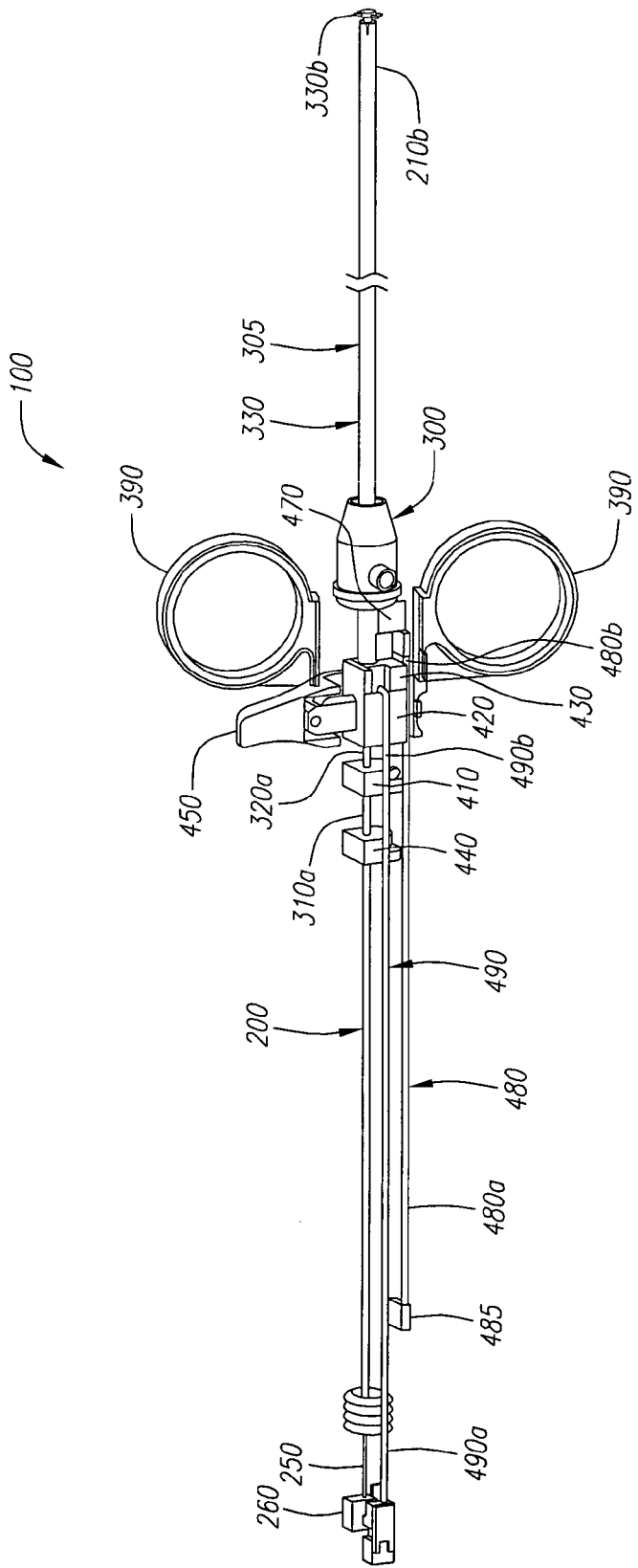
FIG. 4D illustrates a second detailed cross-sectional side view of the triggering system of FIG. 4A.

Turning to FIGS. 4B-D, a triggering system 400 can be disposed substantially within the housing 380. The triggering system 400 is configured to control the relative axial movement and/or positioning of the respective distal end regions 310*b*, 320*b*, 330*b*, and 340*b* of the tube set 305 and/or the distal end region 210*b* of the locator assembly 200. Being coupled with the proximal end regions 210*a*, 310*a*, 320*a*, 330*a*, and/or 340*a*, the triggering system 400 can control the relative axial movement of the distal end regions 210*b*, 310*b*, 320*b*, 330*b*, and/or 340*b* in any manner, such as by being activated by the switching system 450. As desired, the triggering system 400 can induce axial motion, such as distal motion, with respect to one or more of the distal end regions 210*b*, 310*b*, 320*b*, 330*b*, and/or 340*b*. One or more of the distal end regions 210*b*, 310*b*, 320*b*, 330*b*, and/or 340*b* can be axially moved. Axial motion of one or more of the carrier member 310, the pusher member 320, the cover member 330, and the support member 340 and/or the tubular body 210 can be attained, for example, by applying an axial force to the switching system 450. To facilitate monitoring of the positioning of the carrier assembly 300 and/or the substantially tubular closure element 500", one or more of the distal end regions 210*b*, 310*b*, 320*b*, 330*b*, and/or 340*b* may include radiopaque markers (not shown) or may be wholly or partially formed from a radiopaque material.

The triggering system 400 is configured to overcome internal resistance such that the relative axial movement and/or positioning of the respective distal end regions 310*b*, 320*b*, 330*b*, and 340*b* of the tube set 305 and/or the distal end region 210*b* of the locator assembly 200 are controlled in accordance with a predetermined manner when the triggering system 400 is activated. Thereby, movement and/or positioning of the distal end regions 310*b*, 320*b*, 330*b*, 340*b*, and/or 210*b* is initiated when at least a predetermined quantity of force is applied to the switching system 450. Stated somewhat differently, a force that is less than the predetermined quantity generally is insufficient to activate the triggering system 400; whereas, when the force increases to a level that is greater than or substantially equal to the predetermined quantity, the triggering system 400 is configured to activate, moving and/or positioning the distal end regions 310*b*, 320*b*, 330*b*, 340*b*, and/or 210*b* in accordance with the predetermined manner. The triggering system 400, once activated, preferably continues to move and/or position the distal end regions 310*b*, 320*b*, 330*b*, 340*b*, and/or 210*b* in accordance with the predetermined manner until the closure element 500 is deployed.

The triggering system 400, for example, can comprise one or more sets of cooperating detents for coupling the axial motion of the distal end regions 310*b*, 320*b*, 330*b*, and 340*b* in accordance with a predetermined manner when the triggering system 400 is activated. The term "detents" refers to any combination of mating elements, such as blocks, tabs, pockets, slots, ramps, locking pins, cantilevered members, support pins, and the like, that may be selectively or automatically engaged and/or disengaged to couple or decouple the carrier member 310, the pusher member 320, the cover member 330, and the support member 340 relative to one another. It will be appreciated that the cooperating detents as illustrated and described below are merely exemplary and not exhaustive. For example, the cooperating detents can include a first set of cooperating blocks and pockets for releasable coupling the support member 340, the carrier member 310, the pusher member 320, and the cover member 330. When the carrier assembly 300 reaches a first predetermined distal position, the support member 340 can be decoupled from the carrier member 310, the pusher member 320, and the cover member. 330 and preferably is substantially inhibited from further axial movement. Thereby, the carrier member 310, the pusher member 320, and the cover member 330 may continue to be directed distally as the support member 340 remains substantially stationary.

As shown in FIGS. 4B-C, the cooperating detents can comprise a carrier block 410, a pusher block 420, a cover block 430, and a support block 440, which can be configured to couple and decouple in accordance with the predetermined manner. For example, the carrier block 410 is disposed on the proximal end region 310*a* of the carrier member 310 and includes a carrier pin 412*c* that extends from the carrier block 410; whereas, the proximal end region 330*a* of the cover member 330 and the proximal end region 340*a* the support member 340 are respectively coupled with the cover block 430 and the support block 440. A cover pin 432*b* extends from the cover block 430, and the support block 440 has a support pin 442*a*, which extends from the support block 440. The support pin 442*a*, the cover pin 432*b*, and the carrier pin 412*c* each preferably are formed from a substantially rigid material, such as an alloy of nickel-titanium.

The pusher block 420 is disposed on the proximal end region 320*a* of the pusher member 320 and forms a support slot 422*a*, a cover slot 422*b*, and a carrier slot 422*c*. The support slot 422*a* is configured to receive and releasable engage the support pin 442*a* by which the support member 340 can be coupled with, and decoupled from, the pusher member 320. The cover member 330 can be coupled with, and decoupled from, the pusher member 320 via the cover slot 422*b*, which is configured to receive and releasable engage the cover pin 432*b*. The carrier slot 422*c* is configured to receive and releasable engage the carrier pin 412*c* such that the carrier member 310 can be coupled with, and decoupled from, the pusher member 320. The carrier block 410, the pusher block 420, the cover block 430, and the support block 440 preferably are respectively disposed substantially on the outer peripheries 312*b*, 322*b*, 332*b*, and 342*b* and can be configured to couple and decouple in accordance with the predetermined manner.

The triggering system 400 also includes one or more stops for engaging the pusher block 420, the cover block 430, and/or the support block 440, respectively. As illustrated in FIG. 4B, a support stop 460*a*, a cover stop 460*b*, and a carrier stop 460*c* each are formed in the housing 380 and are configured to receive, and substantially inhibit further movement of, the support block 440, the cover block 430, and the carrier block 410, respectively, in accordance with the predetermined manner. For example, when an axial force is applied to the tube set 305 via the switching system 450, the cover block 430 moves distally within the housing 380, and the cover block 430 approaches the cover stop 460*b*. Upon being received by the cover stop 460*b*, the cover block 430 is substantially locked in place, substantially preventing any further motion by the cover block 430.

Resisting the axial force, the cover pin 412*b* provides a static load while the axial force is less than the predetermined quantity of force. As the axial force increases to a level that is greater than or substantially equal to the predetermined quantity, the cover pin 412*b* can be displaced from the cover slot 422*b*, decoupling the cover member 330 from the carrier member 310, the pusher member 320, and the support member 340. Creating the internal resistance to be overcome by the triggering system 400, the static forces provided by the pins 412*a*, 412*b*, and 412*c* is approximately proportional to a composition and cross-section of the respective pins 412*a*, 412*b*, and 412*c* and/or a depth and a slope of the respective slots 422*a*, 422*b*, and 422*c*. As desired, the pins 412*a*, 412*b*, and 412*c* can be configured to provide static loads that are differing and/or substantially uniform.

Turning to FIG. 4D, the triggering system 400 can further have a tube release system 470 for inhibiting inadvertent advancement of the tube set 305. The tube release system 470 is coupled with a tube release member 480, such as a rod, wire, or other elongate member. The tube release member 480 has a proximal end region 480a that is disposed substantially between the pusher block 420 and the housing 380 (shown in FIG. 4A) and a distal end region 480b that is coupled with the tube release system 470. Preferably, a tab 485 is coupled with the proximal end region 480a of the tube release member 480, and a pin (not shown) extends from the pusher block 420 and is disposed substantially between the tab 485 and a groove (not shown) formed in the housing 380. The tube release system 470 is configured to release the tube set 305 when the tube release member 480 is moved proximally, freeing the pusher block 420.

A locator release system 490 for permitting the distal end region 210b, the expansion elements 230, and/or the substantially flexible members 230' of the locator assembly 200 to transition from the expanded state to the unexpanded state can be included with the triggering system 400. The locator release system 490 can comprise a rod, wire, or other elongate member and has a proximal end region 490a and a distal end region 490b. The proximal end region 490a of the locator release system 490 can be coupled with, and configured to activate, the locator control system 240 (shown in FIG. 2D), and the distal end region 490b extends beyond the pusher block 420. Thereby, when the pusher block 420 is advanced during deployment of the closure element 500, the control block 260 is disengaged such that the distal end region 210b, the expansion elements 230, and/or the substantially flexible members 230' of the locator assembly 200 to transition from the expanded state to the unexpanded state.

Figure 5C:
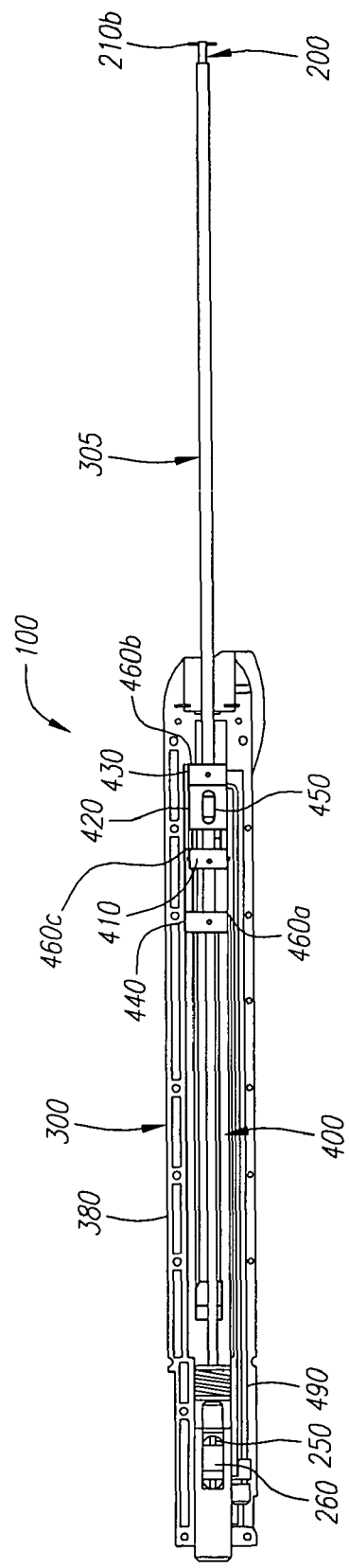
FIG. 5C illustrates the carrier control system of FIGS. 4A-D as the carrier assembly of FIG. 3A reaches a second predetermined position.

The operation of the triggering system 400 in accordance with one predetermined manner is illustrated in FIGS. 5A-C with the closure element 500 (shown in FIGS. 6A-B) disposed substantially within the apparatus 100. As shown in FIG. 5A, the distal end region 210b of the locator assembly 200 has been positioned as desired and has transitioned from the unexpanded state to the expanded state. While the locator control system 240 (shown in FIG. 2D) maintains the distal end region 210b in the expanded state, a distally-directed axial force is applied to the triggering system 400 via the switching system 450. Once the tube release member 480 (shown in FIG. 4D) has been moved proximally to free the pusher block 420, the tube set 305 is substantially freely slidable within the housing 380 and responds to the axial force by sliding distally from an initial predetermined position to a first predetermined position.

In the initial predetermined position, the carrier member 310, the pusher member 320, the cover member 330, and the support member 340 are coupled via the slots 422c, 422b, and 422a (shown in FIG. 4C) and the pins 412c, 422b, and 442a (shown in FIG. 4C). Stated somewhat differently, the support pin 442a, the cover pin 432b, and the carrier pin 412c are respectively disposed within, and engaged by, the support slot 422a, the cover slot 422b, and the carrier slot 422c such that the carrier block 410, the pusher block 420, the cover block 430, and the support block 440 are coupled as illustrated in FIG. 4C. Therefore, the carrier member 310, the pusher member 320, the cover member 330, and the support member 340 each slide distally from the initial predetermined position to the first predetermined position in response to the axial force.

FIG. 5B illustrates the positions of the carrier member 310, the pusher member 320, the cover member 330, and the support member 340 upon reaching the first predetermined position. In the first predetermined position, the support block 440 and the cover block 430 respectively engage the support stop 460a and the cover stop 460b. Thereby, the support stop 460a receives, and substantially inhibits further movement of, the support block 440 and, therefore, the support member 340; whereas, the cover stop 460b receives, and substantially inhibits further movement of, the cover block 430 and, therefore, the cover member 330. Although the support block 440 and the cover block 430 preferably engage the support stop 460a and the cover stop 460b in the first predetermined position, it will be appreciated that the support block 440 can engage the support stop 460a and the cover block 430 can engage the cover stop 460b in different predetermined positions. In other words, the predetermined manner can comprise any number of predetermined positions, each predetermined position being associated with any number of the blocks 410, 420, 430, and 440 engaging any number of relevant stops 460a, 460b, and 460c.

To continue distally from the first predetermined position, the carrier member 310 and the pusher member 320 can be decoupled from the cover member 330 and the support member 340 by disengaging the support pin 442a and the cover pin 432b from the support slot 422a and the cover slot 422b, respectively. In the manner described in more detail above with reference to FIGS. 4B-C, the support pin 442a and the cover pin 432b each resist the axial force. While the axial force is less than the combined static force provided by the support pin 442a and the cover pin 432b, the carrier member 310 and the pusher member 320 remain coupled with the cover member 330 and the support member 340. As the axial force increases to a level that is greater than or substantially equal to the combined static force, the support pin 442a and the cover pin 432b are respectively displaced from the support slot 422a and the cover slot 422b, decoupling the carrier member 310 and the pusher member 320 from the cover member 330 and the support member 340. Thereby, the cover member 330 and the support member 340 preferably are inhibited from further distal movement and remain substantially stationary; whereas, the carrier member 310 and the pusher member 320 proceed distally toward a second predetermined position.

The pusher member 320 and the carrier member 310 continue distally until the second predetermined position is reached as shown in FIG. 5C. In the second predetermined position, the carrier block 410 engages the carrier stop 460c. Thereby, the carrier stop 460c receives, and substantially inhibits further movement of, the carrier block 410 and, therefore, the carrier member 310. To continue distally from the second predetermined position, the pusher member 320 can be decoupled from the carrier member 310 by disengaging the carrier pin 412c from the carrier slot 422c. In the manner described in more detail above with reference to FIGS. 4B-C, the carrier pin 412c resists the axial force. While the axial force is less than the static force provided by the carrier pin 412c, the pusher member 320 remains coupled with the carrier member 310.

As the axial force increases to a level that is greater than or substantially equal to the static force, the carrier pin 412c is displaced from the carrier slot 422c, decoupling the pusher member 320 from the carrier member 310. Thereby, the carrier member 310 preferably is inhibited from further distal movement and remains substantially stationary; whereas, the pusher member 320 proceed distally to deploy the closure element 500 and to activate the locator release system 490 (shown in FIG. 2D) such that the distal end region 210b, the expansion elements 230, and/or the substantially flexible members 230' of the locator assembly 200 transition from the expanded state to the unexpanded state. Preferably, the axial force that is applied to overcome the static force associated with the first predetermined position is sufficient to overcome the static forces associated with the subsequent predetermined positions, to deploy the closure element 500, and to activate the locator release system 490 such that the triggering system 400 operates in one substantially-continuous motion.

It will be appreciated that the triggering system 400 can include an energy storing element (not shown), which can be disposed substantially between the housing 380 and the blocks 410, 420, 430, and 440 and which is configured to store potential energy for moving the tube set 305 from the initial predetermined position through the other predetermined positions, deploying the closure element 500, and/or activating the locator release system 490. The energy storing element is configured store the potential energy when the tube set 305 is in the initial predetermined position and to release the potential energy, when activated, such that the tube set 305 travels through the predetermined positions at a substantially constant and continuous rate. For example, the energy storing element can comprise one or more springs (not shown). Each of the springs can be in a compressed state when the tube set 305 is in the initial predetermined position and released from the compressed state when the switching system 450 of the triggering system 400 is activated.

In use, the closure element 500 is disposed within the carrier assembly 300. As shown in FIGS. 7A-B, for example, the reduced closure element 500' can be slidably received over the distally-increasing cross-section 318*b* of the distal end region 310*b* of the carrier member 310 and disposed about the periphery 312 of the carrier member 310 adjacent to the space 360. Since the reduced cross-section 530' of the reduced closure element 500' is less than the cross-section 318*b* of the distally-increasing cross-section 318*b*, the reduced closure element 500' must be temporarily radially deformed to be received over the distal end region 310*b*. Also, as the reduced closure element 500' is received over the distal end region 310*b*, the opposing tines 520 of the reduced closure element 500' engage the distal end region 310*b*. The reduced closure element 500' thereby forms the substantially tubular closure element 500" in the manner described in more detail above with reference to FIGS. 6E-G.

After being received over the distal end region 310*b*, the substantially tubular closure element 500" is disposed about the space 360, and the tines 520 are directed substantially distally as shown in FIG. 7B. As desired, one or more of the tines 520 can be disposed proximally of the distally-increasing cross-section 318*b* of the distal end region 310*b*, as illustrated in FIG. 7B, and/or can be at least partially disposed upon, and contact, the distally-increasing cross-section 318*b* of the distal end region 310*b*. To improve the engagement between the closure element 500 (shown in FIGS. 6A-B) and the blood vessel wall 620 and/or tissue 630 (collectively shown in FIG. 8A), the substantially tubular closure element 500" preferably is disposed on the carrier member 310 such that the tines 520 define a first plane that is substantially perpendicular to a second plane defined by the switching system 450 and/or the handles 390 (collectively shown in FIG. 5A).

Once disposed about the space 360, the substantially tubular closure element 500" can be retained on the outer periphery 312*b* of the carrier member 310 when distal end region 310*b* of the carrier member 310 and the distal end region 320*b* of the pusher member 320 are slidably received within the lumen 334 of the cover member 330 as illustrated in FIGS. 7C-D. When the cover member 330 is properly positioned within the carrier assembly 300, the distal end region 330*b* of the cover member 330 extends over the space 360 and defines the annular cavity 370 for retaining the substantially tubular closure element 500". As such, the substantially tubular closure element 500" is disposed substantially between the outer periphery 312*b* of the carrier member 310 and the inner periphery 332*a* of the cover member 330 such that the substantially tubular closure element 500" maintains the substantially tubular configuration with the tines 520 being directed substantially distally. As desired, the tube set 305 may radially compress the substantially tubular closure element 500" such that the substantially tubular closure element 500" enters and maintains a compressed tubular configuration. The body 510 of the substantially tubular closure element 500" can be disposed distally of the distal end region 320*b* of the pusher member 320, as illustrated in FIGS. 7C-D, or can engage the distal end region 320*b*, as desired.

Figure 8A:
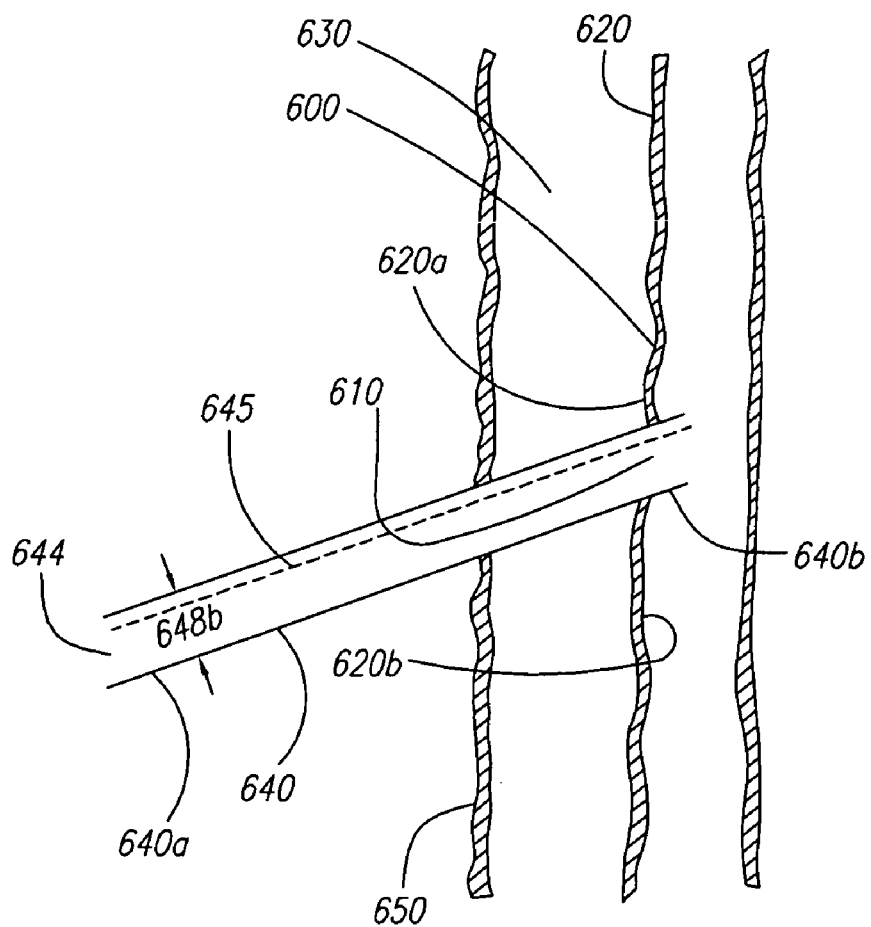
FIG. 8A illustrates a sheath that is positioned through tissue and into an opening formed in a wall of a blood vessel.

Turning to FIG. 8A, a sheath 640 may be inserted or otherwise positioned through skin 650 and tissue 630 and within the blood vessel 600 or other body lumen via the opening 610. Comprising a substantially flexible or semi-rigid tubular member, the sheath 640 has a proximal end region 640*a* and a distal end region 640*b* and includes a predetermined length and a predetermined cross-section, both of which can be of any suitable dimension. The sheath 640 also forms a lumen 644 that extends along a longitudinal axis of the sheath 640 and substantially between the proximal and distal end regions 640*a*, 640*b*. The lumen 644 can have any suitable internal cross-section 648*b* and is suitable for receiving one or more devices (not shown), such as a catheter, a guide wire, or the like. The lumen 644 is configured to slidably receive the tubular body 210 of the locator assembly 200 (shown in FIG. 4A) and/or the tube set 305 of the carrier assembly 300 (shown in FIG. 4A).

Since the internal cross-section 648*b* of the sheath 640 typically is less than or substantially equal to the predetermined cross-section 338*b* of the cover member 330, the sheath 640 may be configured to radially expand, such as by stretching, to receive the tube set 305. Alternatively, or in addition, the sheath 640 can be advantageously configured to split as the tube set 305 is received by, and advances within, the lumen 644 of the sheath 640, thereby permitting the apparatus 100 to access the blood vessel wall 620. To facilitate the splitting, the sheath 640 can include one or more splits 645, such as longitudinal splits, each split being provided in the manner known in the art. Each split 645 is configured to split the sheath 640 in accordance with a predetermined pattern, such as in a spiral pattern. It will be appreciated that, when the internal cross-section 648*b* of the sheath 640 is greater than the predetermined cross-section 338*b* of the cover member 330, it may not be necessary for the sheath 640 to be configured to radially expand and/or split.

The sheath 640 may be advanced over a guide wire or other rail (not shown) that was previously positioned through the opening 610 and into the blood vessel 600 using conventional procedures. Preferably, the blood vessel 600 is a peripheral blood vessel, such as a femoral or carotid artery, although other body lumens may be accessed using the sheath 640 as will be appreciated by those skilled in the art. The opening 610, and consequently the sheath 640, may be oriented with respect to the blood vessel 600 such as to facilitate the introduction of devices through the lumen 644 of the sheath 640 and into the blood vessel 600 with minimal risk of damage to the blood vessel 600. One or more devices (not shown), such as a catheter, a guide wire, or the like, may be inserted through the sheath 640 and advanced to a preselected location within the patient's body. For example, the devices may be used to perform a therapeutic or diagnostic procedure, such as angioplasty, atherectomy, stent implantation, and the like, within the patent's vasculature.

Figure 8B:
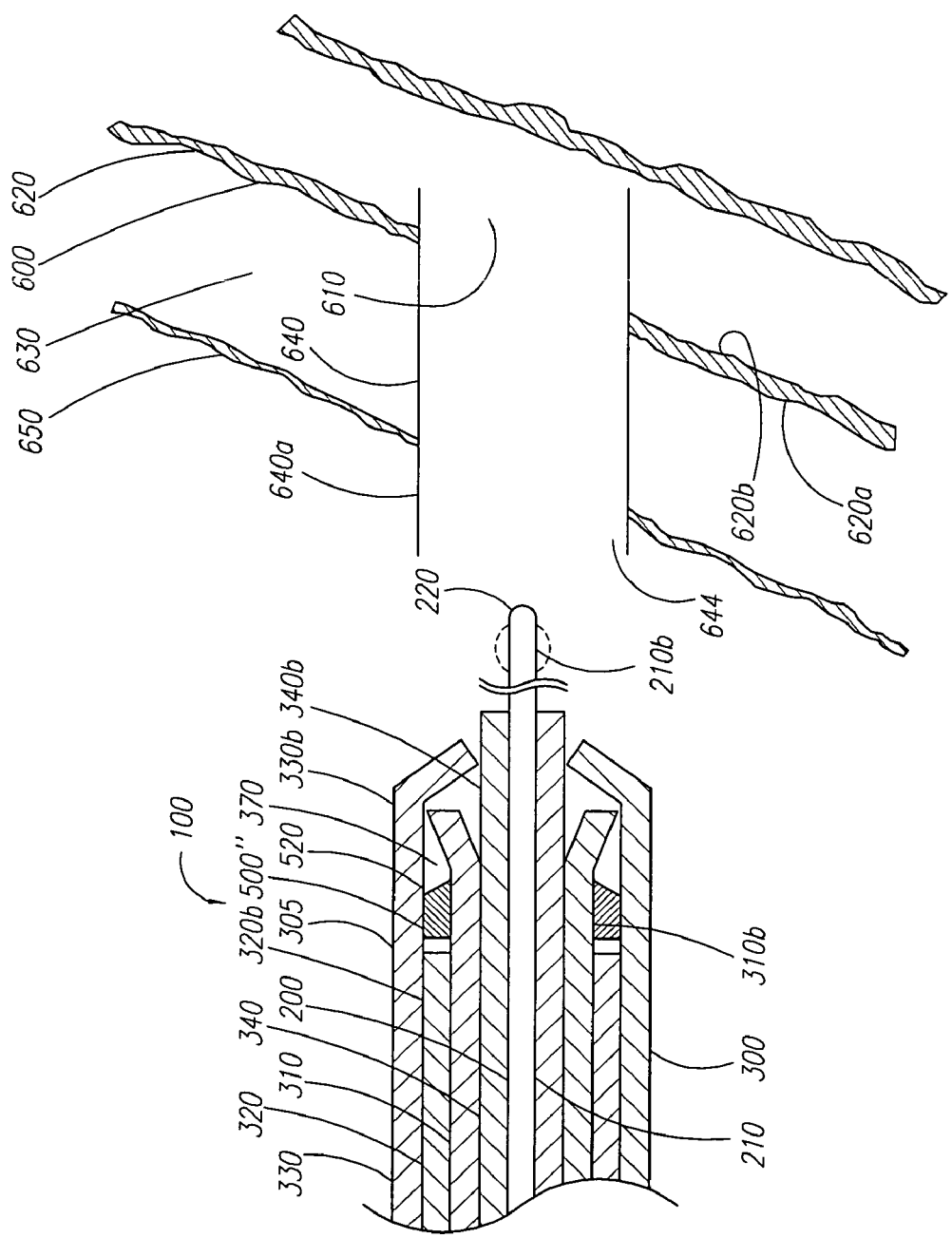
FIG. 8B illustrates the apparatus of FIG. 1 as prepared to be received by the sheath of FIG. 8A.
Figure 8C:
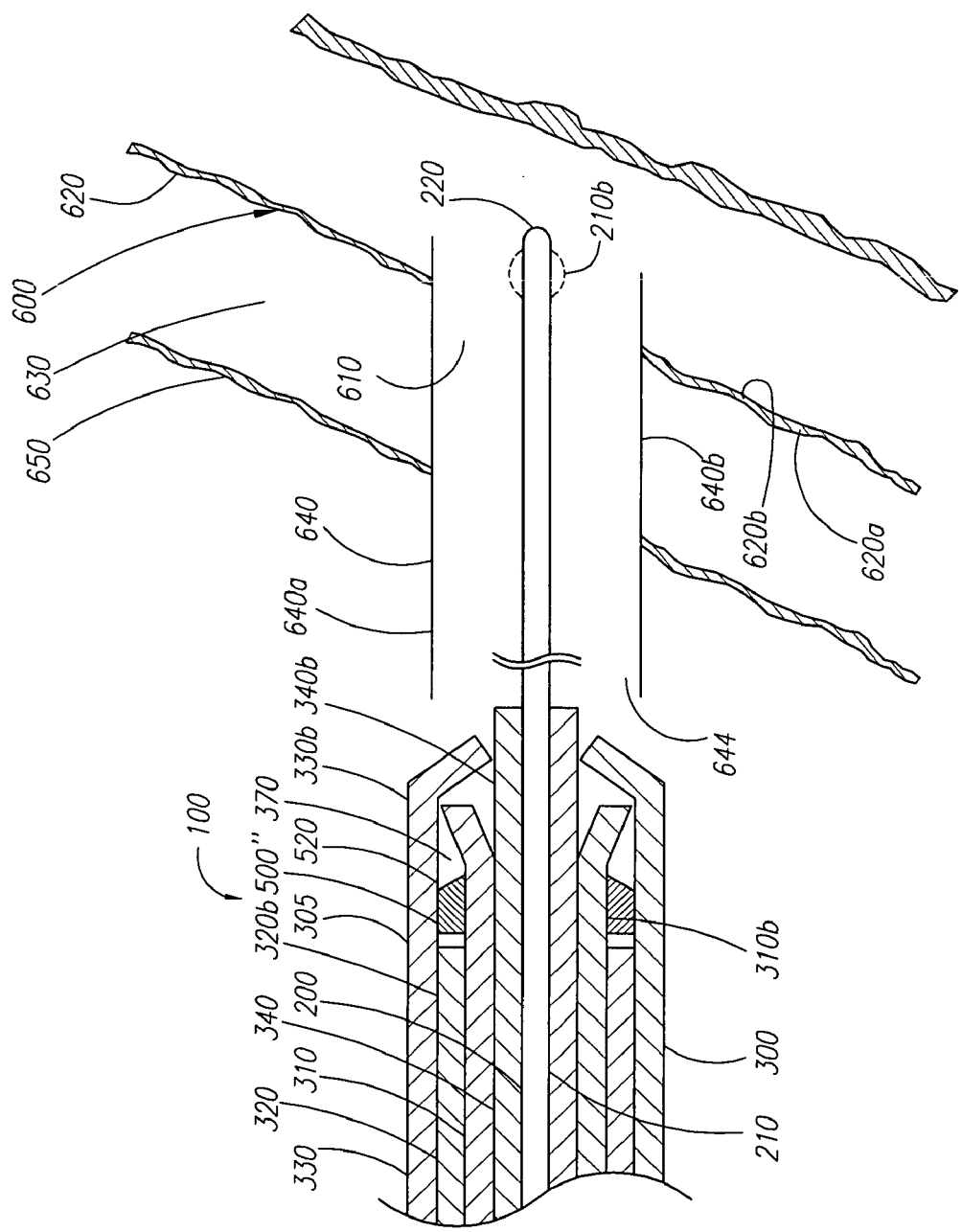
FIG. 8C illustrates a locator assembly of the apparatus of FIG. 8B being advanced distally into the blood vessel.
Figure 8D:
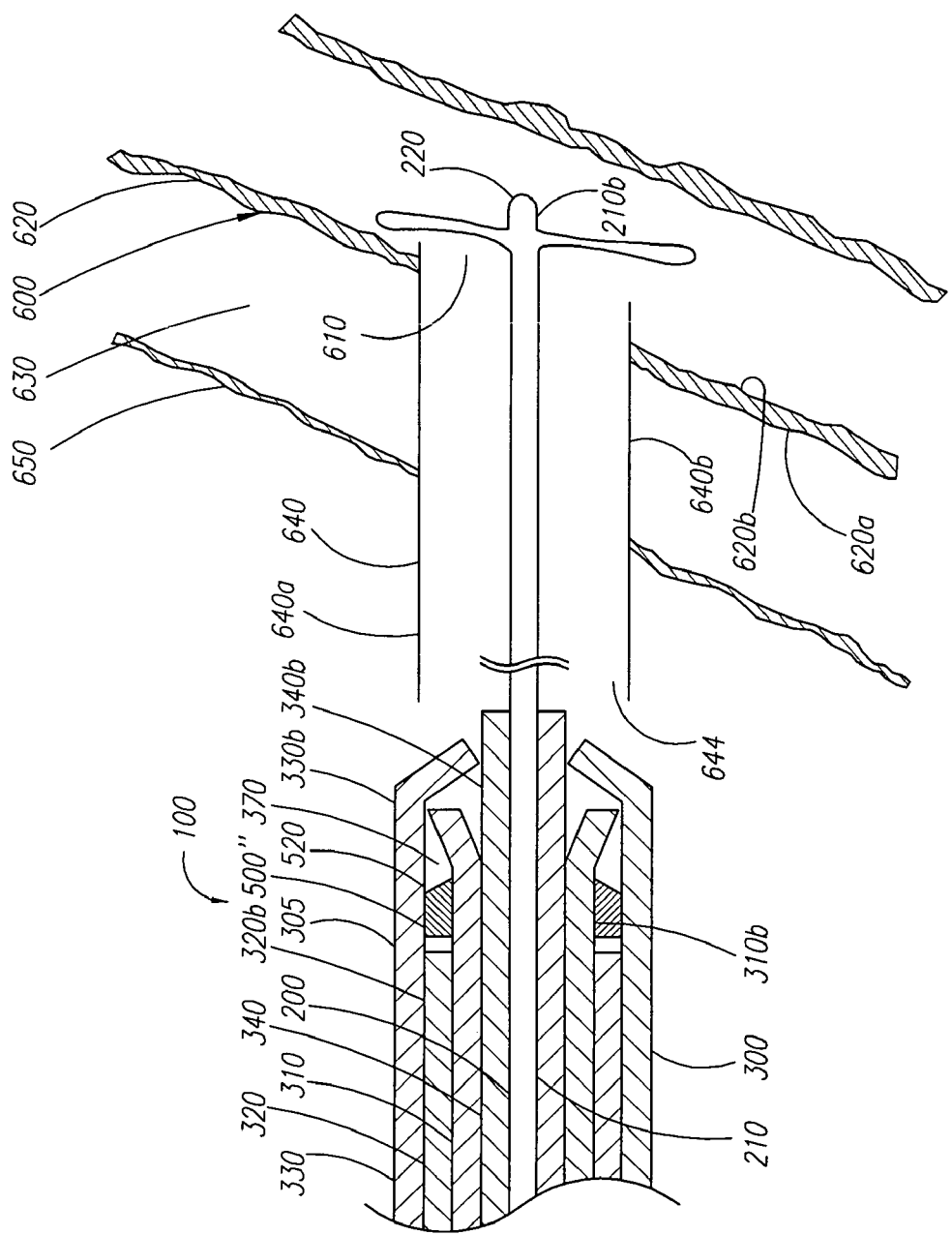
FIG. 8D illustrates a distal end region of the locator assembly of FIG. 8C extending into the blood vessel and being transitioned into an expanded state.

After the procedure is completed, the devices are removed from the sheath 640, and the apparatus 100 is prepared to be received by the lumen 644 of the sheath 640 as shown in FIG. 8B. Being in the unexpanded state, the distal end region 210b of the tubular body 210 of the locator assembly 200 is slidably received by the lumen 644 and atraumatically advanced distally into the blood vessel 600 as illustrated in FIGS. 8B-C. Once the distal end region 210b of the tubular body 210 extends into the blood vessel 600, the distal end region 210b can transition from the unexpanded state to the expanded state as shown in FIG. 8D by activating the switching system of the locator assembly 200.

Figure 8E:
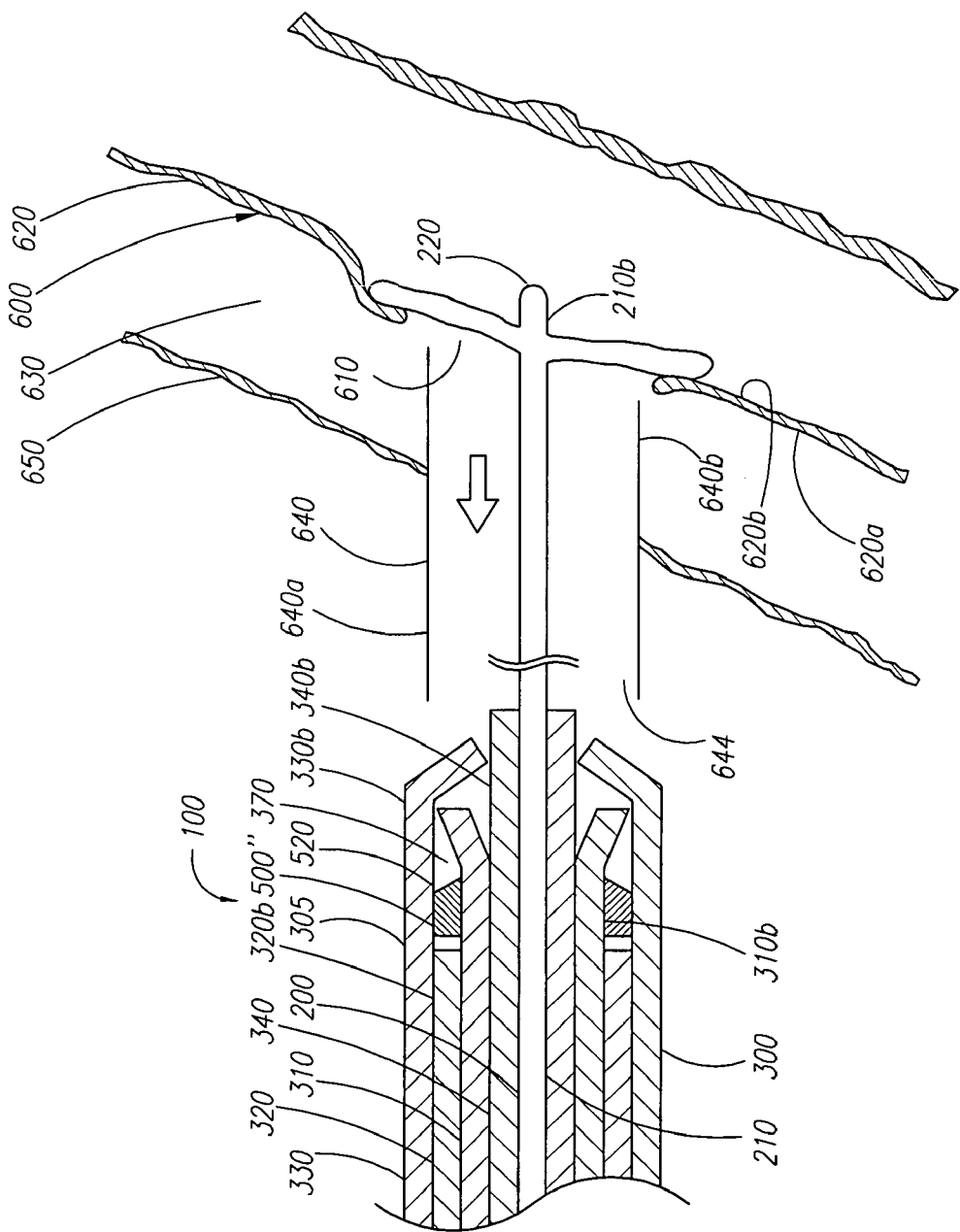
FIG. 8E illustrates the distal end region of FIG. 8D being retracted proximally to engage an inner surface of the blood vessel wall.

Turning to FIG. 8E, the apparatus 100 and the sheath 640 then are retracted proximally until the distal end region 210b is substantially adjacent to an inner surface 620b of the blood vessel wall 620. The distal end region 210b thereby draws the blood vessel wall 620 taut and maintains the proper position of the apparatus 100 as the blood vessel 600 pulsates. Since the expanded cross-section of the distal end region 210b is greater than or substantially equal to the cross-section of the opening 610 and/or the cross-section of the lumen 644, the distal end region 210b remains in the blood vessel 600 and engages the inner surface 620b of the blood vessel wall 620. The distal end region 210b can frictionally engage the inner surface 620b of the blood vessel wall 620, thereby securing the apparatus 100 to the blood vessel 600. The sheath 640 is retracted proximally such that the distal end region 640b of the sheath 640 is substantially withdrawn from the blood vessel 600, as shown in Fig. E, permitting the apparatus 100 to access the blood vessel wall 620.

As the apparatus 100 is being retracted, the apparatus 100 preferably also is axially rotated such that the first plane defined by the tines 520 of the substantially tubular closure element 500" is substantially parallel with a third plane defined by the blood vessel 600. Thereby, the engagement between the substantially tubular closure element 500" and the blood vessel wall 620 and/or tissue 630 can be improved because the tines 520 are configured to engage the blood vessel wall 620 and/or tissue 630 at opposite sides of the opening 610. If the substantially tubular closure element 500" is disposed on the carrier member 310 such that the first plane defined by the tines 520 is substantially perpendicular to the second plane defined by the switching system 450 and/or the handles 390 (collectively shown in FIG. 5A), for example, the apparatus 100 can be positioned such that the second plane defined by the switching system 450 and/or the handles 390 is substantially perpendicular to the third plane defined by the blood vessel 600.

Figure 8F:
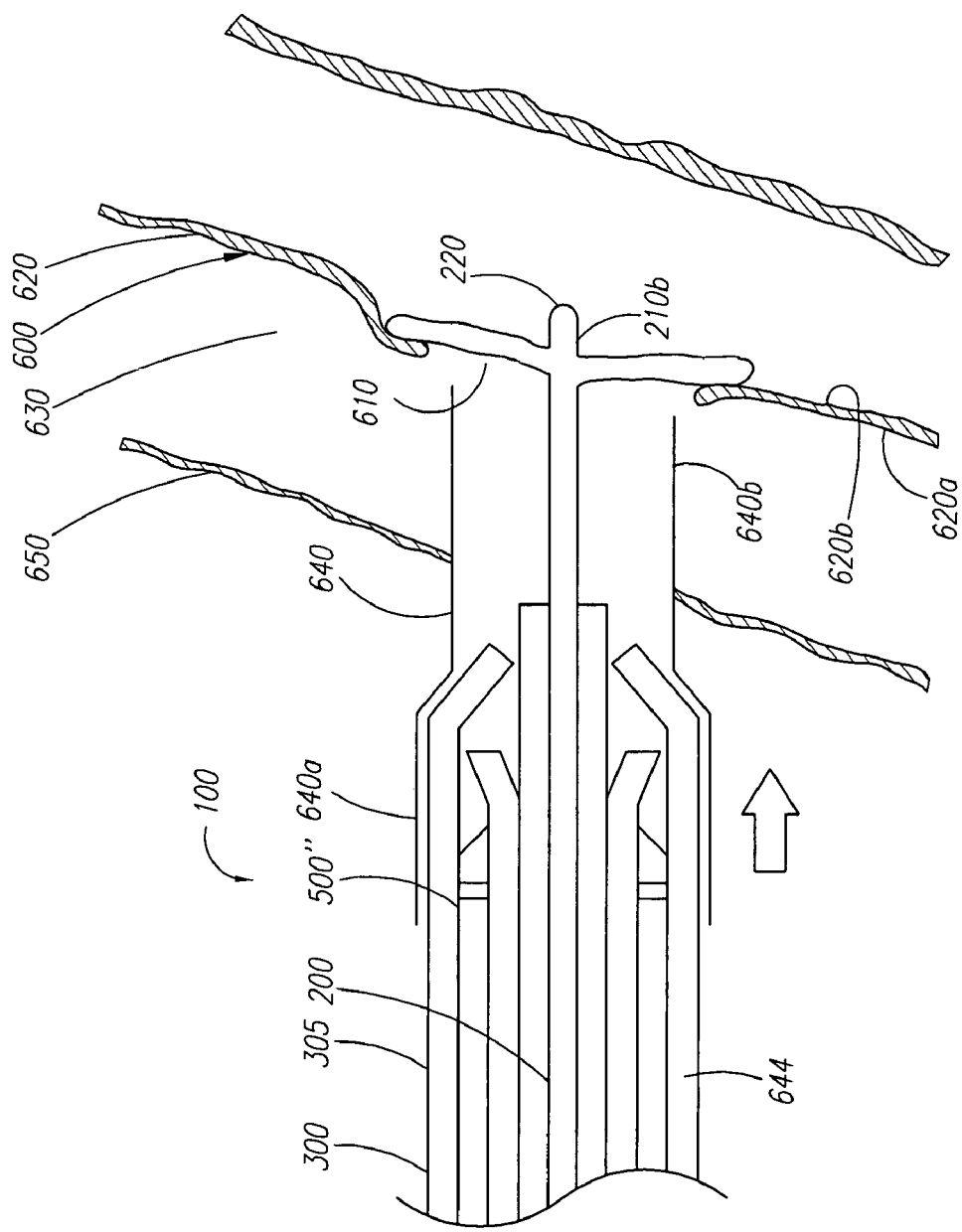
FIG. 8F illustrates a carrier assembly of the apparatus of FIG. 8B being advanced distally into the sheath of FIG. 8A once the distal end region of FIG. 8D has engaged the inner surface of the blood vessel wall.
Figure 8G:
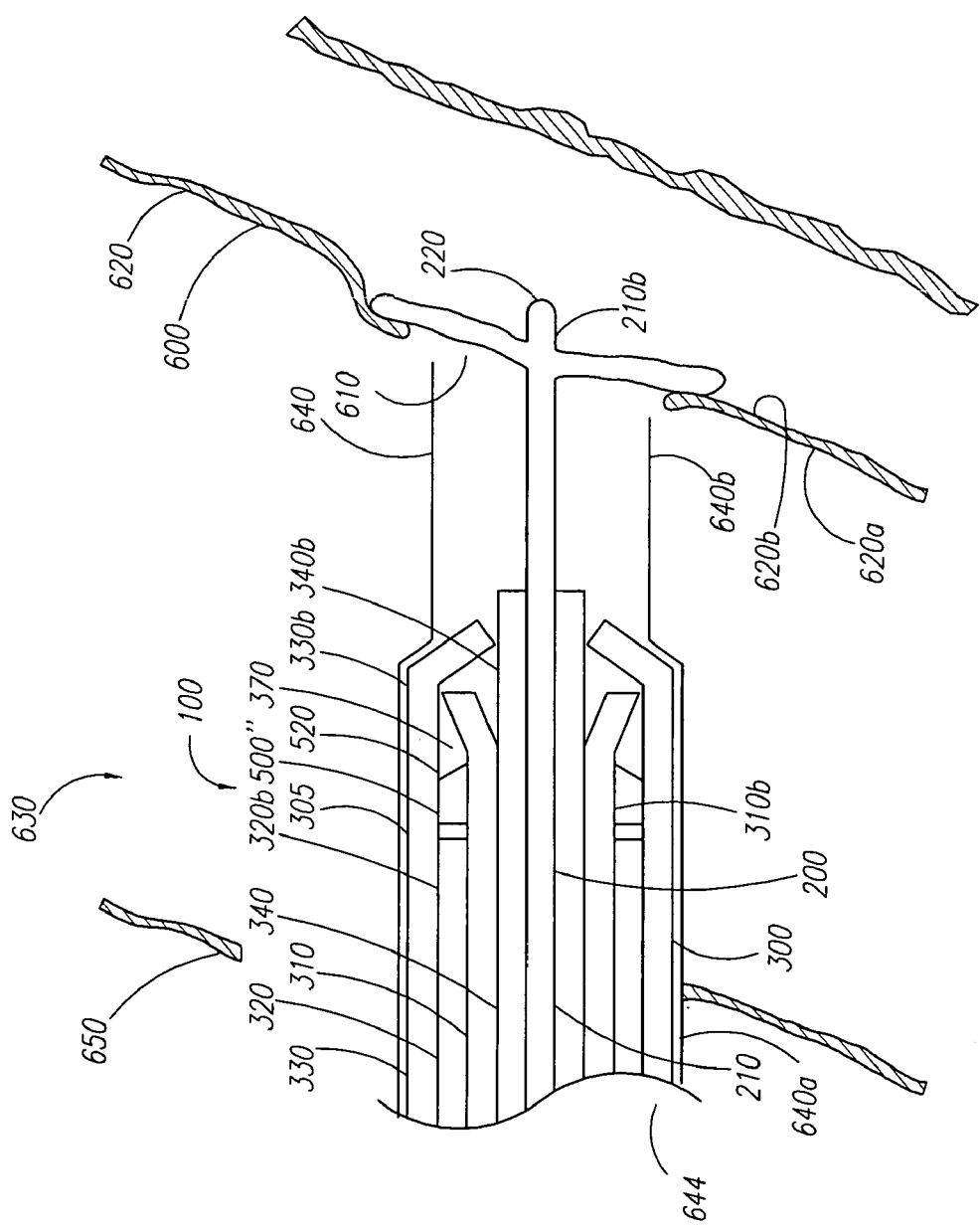
FIG. 8G illustrates relative positions of a tube set of the carrier assembly of FIG. 5F upon reaching a first predetermined position.

Once the distal end region 210b of the locator assembly 200 engages the inner surface 620b of the blood vessel wall 620, the tube release system 470 (shown in FIG. 4D) is activated to release the tube set 305, which can be advanced distally and received within the lumen 644 of the sheath 640 as illustrated in FIG. 8F. In the manner described in more detail above with reference to FIG. 8A, the sheath 640 can radially expand and/or split in accordance with the predetermined pattern as the tube set 305 advances because the internal cross-section 648b of the sheath 640 is less than or substantially equal to the predetermined cross-section 338b of the cover member 330. Being coupled, the carrier member 310, the pusher member 320, the cover member 330, and the support member 340 each advance distally and approach the first predetermined position as illustrated in FIG. 8G.

Upon reaching the first predetermined position, the tube set 305 is disposed substantially adjacent to the outer surface 620a of the blood vessel wall 620 adjacent to the opening 610 such that the blood vessel wall 620 adjacent to the opening 610 is disposed substantially between the expanded distal region 210b of the locator assembly 200 and the tube set 305. The cover member 330 and the support member 340 each decouple from the carrier member 310 and the pusher member 320 in the manner described in more detail above with reference to FIGS. 5A-C when the tube set 305 is in the first predetermined position. Thereby, the cover member 330 and the support member 340 preferably are inhibited from further axial movement and remain substantially stationary as the carrier member 310 and the pusher member 320 each remain coupled and axially slidable.

Figure 8H:
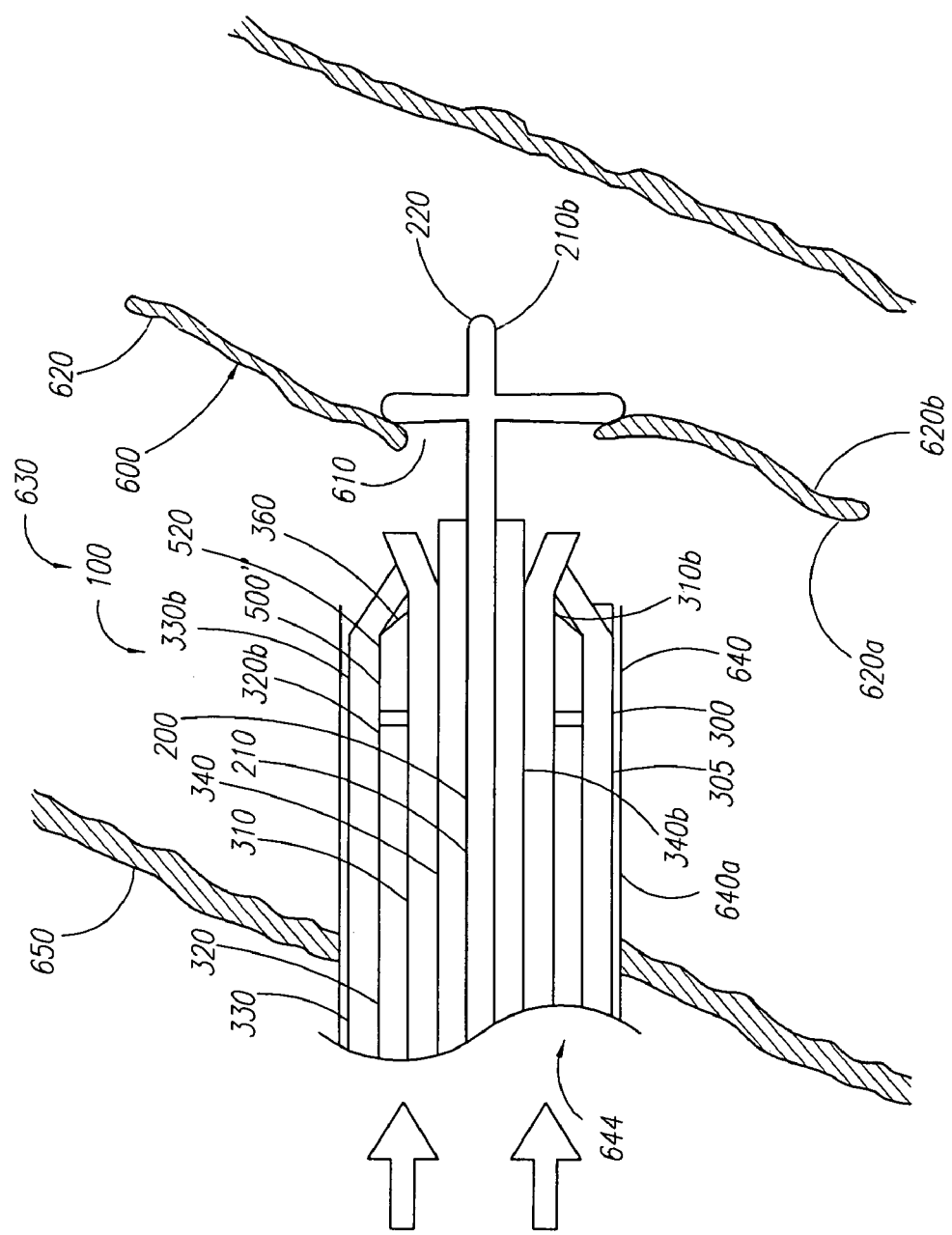
FIG. 8H illustrates the relative positions of the tube set of FIG. 8G upon reaching a second predetermined position.

As shown in FIG. 8H, the cover member 330 and the support member 340 remaining substantially stationary while the carrier member 310 and the pusher member 320 continue distally and approach the second predetermined position. As the carrier member 310 and the pusher member 320 distally advance toward the second predetermined position, the annular cavity 370 moves distally relative to the substantially-stationary cover member 330 such that the distal end region 330b of the cover member 330 no longer encloses the annular cavity 370. Thereby, the substantially tubular closure element 500" is not completely enclosed by the annular cavity 370 formed by the distal end regions 310b, 320b, and 330b of the carrier member 310, the pusher member 320, and the cover member 330.

Although not completely enclosed by the annular cavity 370, the substantially tubular closure element 500" is advantageously retained on the outer periphery 312b of the carrier member 310 by the distal end region 330b of the cover member 330 as illustrated in FIG. 8H. For example, by retaining the substantially tubular closure element 500" between the distal end region 330b of the cover member 330 and the distal end region 310b the carrier member 310, the apparatus 100 is configured to provide better tissue penetration. The timing between the deployment of the substantially tubular closure element 500" by the tube set 305 and the retraction and transition to the unexpanded state by the locator assembly 200 likewise is facilitated because the substantially tubular closure element 500" is retained between the distal end region 330b and the distal end region 310b. Further, the carrier member 310 and the cover member 330 operate to maintain the substantially tubular closure element 500" in the tubular configuration.

Figure 8I:
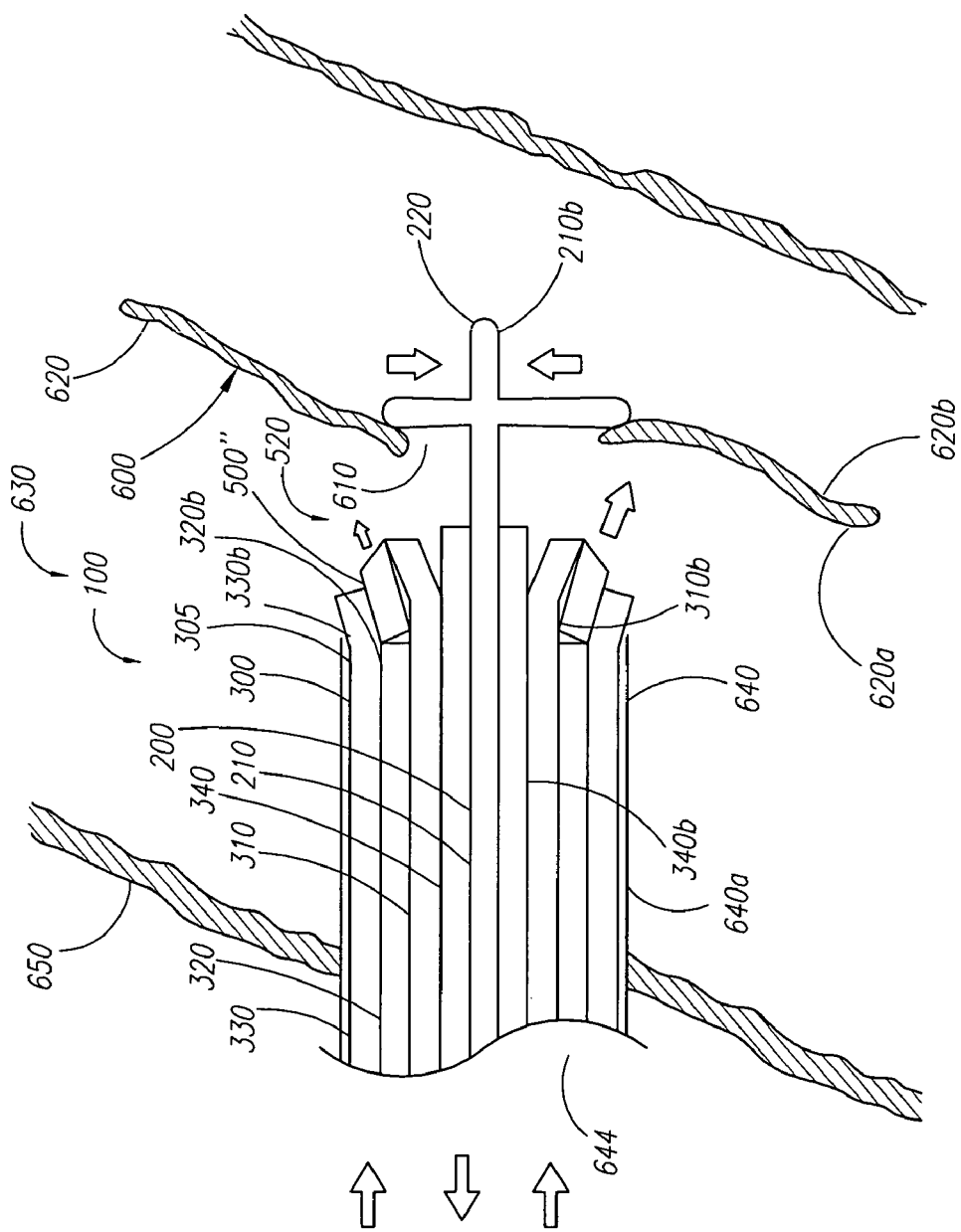
FIG. 8I illustrates a position of a pusher member of the tube set of FIG. 8H moving distally from the second predetermined position and beginning to distally deploy a closure element.

When the tube set 305 is in the second predetermined position, the carrier member 310 decouples from the pusher member 320 in the manner described in more detail above with reference to FIGS. 5A-C. Therefore, the carrier member 310, the cover member 330, and the support member 340 preferably are inhibited from further axial movement and remain substantially stationary; whereas, the pusher member 320 remains axially slidable. As the pusher member 320 continues distally, the distal end region 320b of the pusher member 320 engages the substantially tubular closure element 500" and displaces the substantially tubular closure element 500" from the space 360 as shown in FIG. 8I. Since the space 360 is substantially radially exposed, the pusher member 320 directs the substantially tubular closure element 500" over the distally-increasing cross-section of the distal end region 310b of the substantially-stationary carrier member 310 such that the cross-section 530' (shown in FIGS. 6F-G) of the substantially tubular closure element 500" begins to radially expand, preferably in a substantially uniform manner. As the substantially tubular closure element 500" traverses the distally-increasing cross-section of the distal end region 310b, the cross-section 530' of the substantially tubular closure element 500" radially expands beyond natural cross-section 530 (shown in FIGS. 6A-B) of the closure element 500.

Figure 8J:
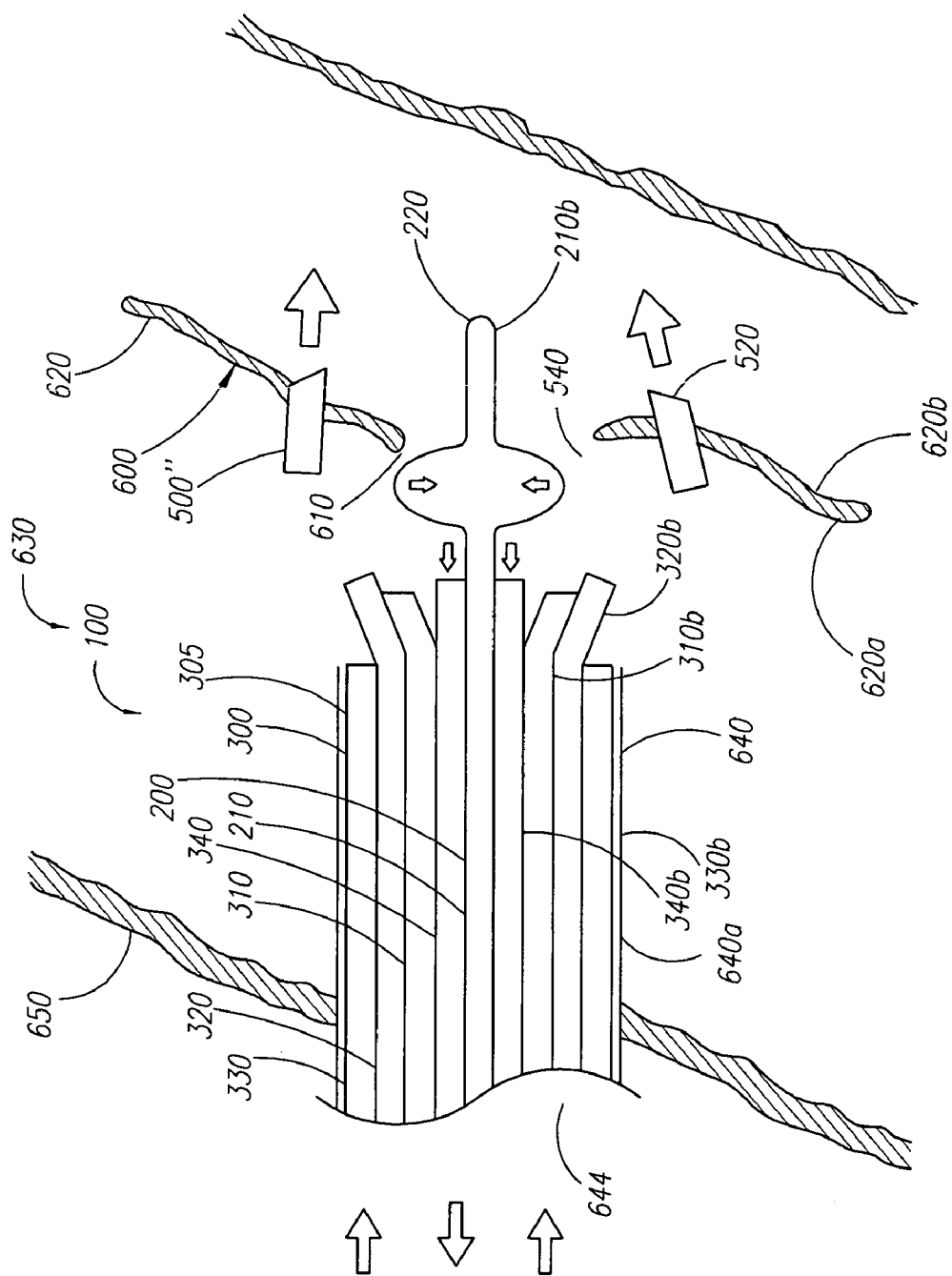
FIG. 8J illustrates the closure element of FIG. 8I upon being deployed and engaging tissue adjacent to the opening in the blood vessel wall.

Upon being directed over the distally-increasing cross-section of the distal end region 310b by the pusher member 320, the substantially tubular closure element 500" is distally deployed as illustrated in FIG. 8J. When the substantially tubular closure element 500" is deployed, the tines 520 can pierce and otherwise engage significant amount of the blood vessel wall 620 and/or tissue 630 adjacent to the opening 610. For example, the tines 520 can engage significant amount of the blood vessel wall 620 and/or tissue 630 because the cross-section 530' of the substantially tubular closure element 500" is expanded beyond natural cross-section 530 of the closure element 500 during deployment.

The distal end region 210b of the locator assembly 200 also begins to retract proximally and the locator release system 490 (shown in FIG. 4D) can be activated to transition from the expanded state to the unexpanded state as the substantially tubular closure element 500" is deployed as shown in FIG. 8J. Preferably, the distal end region 210b of the locator assembly 200 retracts proximally and transitions from the expanded state to the unexpanded state substantially simultaneously with the deployment of the substantially tubular closure element 500". As desired, the distal end region 210b may be configured to draw the blood vessel wall 620 and/or tissue 630 adjacent to the opening 610 proximally and into the channel 540 defined by the substantially tubular closure element 500". The tines 520 of the substantially tubular closure element 500" thereby can pierce and otherwise engage the drawn blood vessel wall 620 and/or tissue 630. Since the cross-section 530' of the substantially tubular closure element 500" is expanded beyond natural cross-section 530 of the closure element 500, a significant amount of the blood vessel wall 620 and/or tissue 630 can be drawn into the channel 540 and engaged by the tines 520.

Figure 8K:
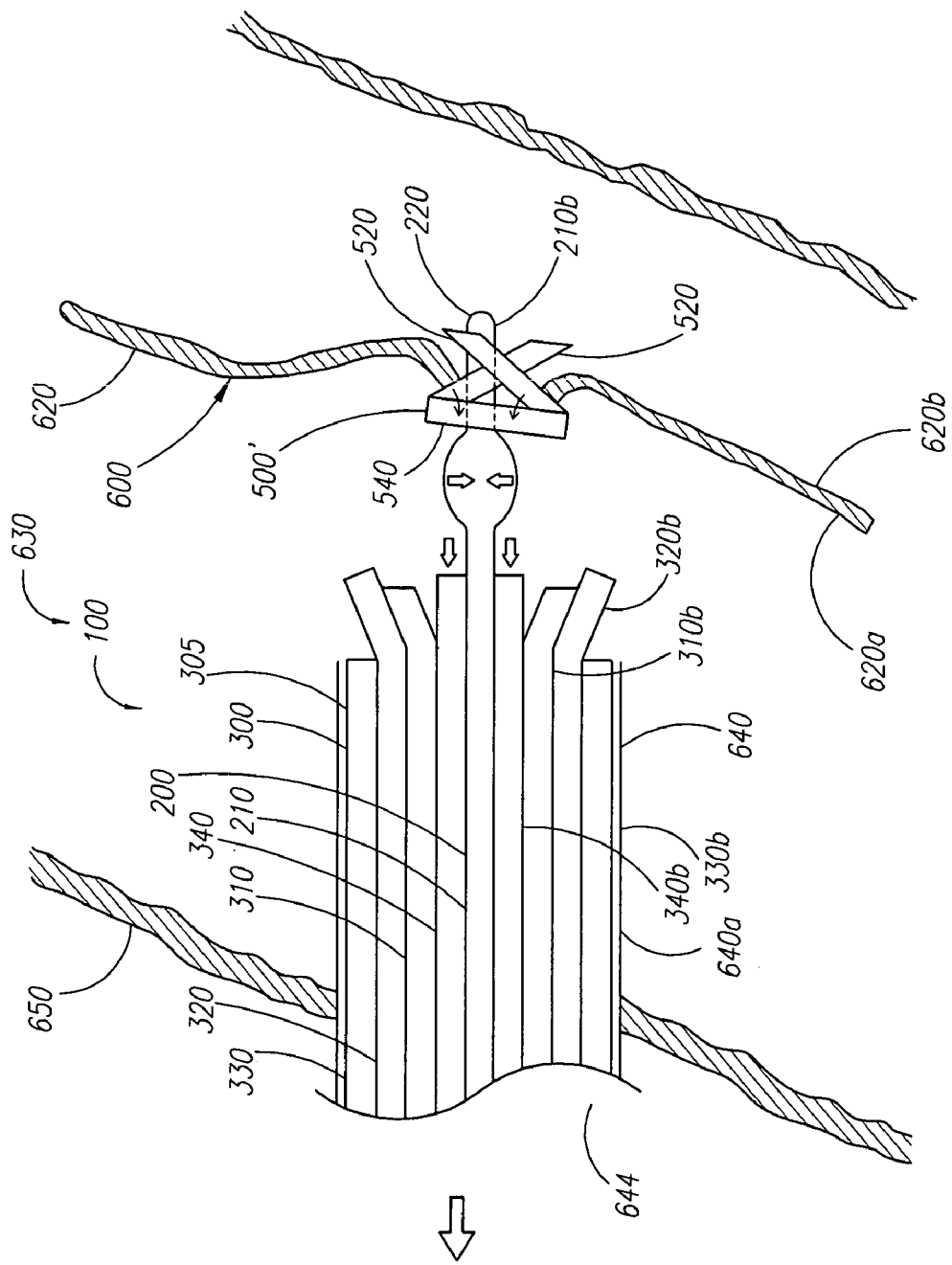
FIG. 8K illustrates the closure element of FIG. 8J transitioning from the substantially tubular configuration to the natural, planar configuration while engaging the engaged tissue.
Figure 8L:
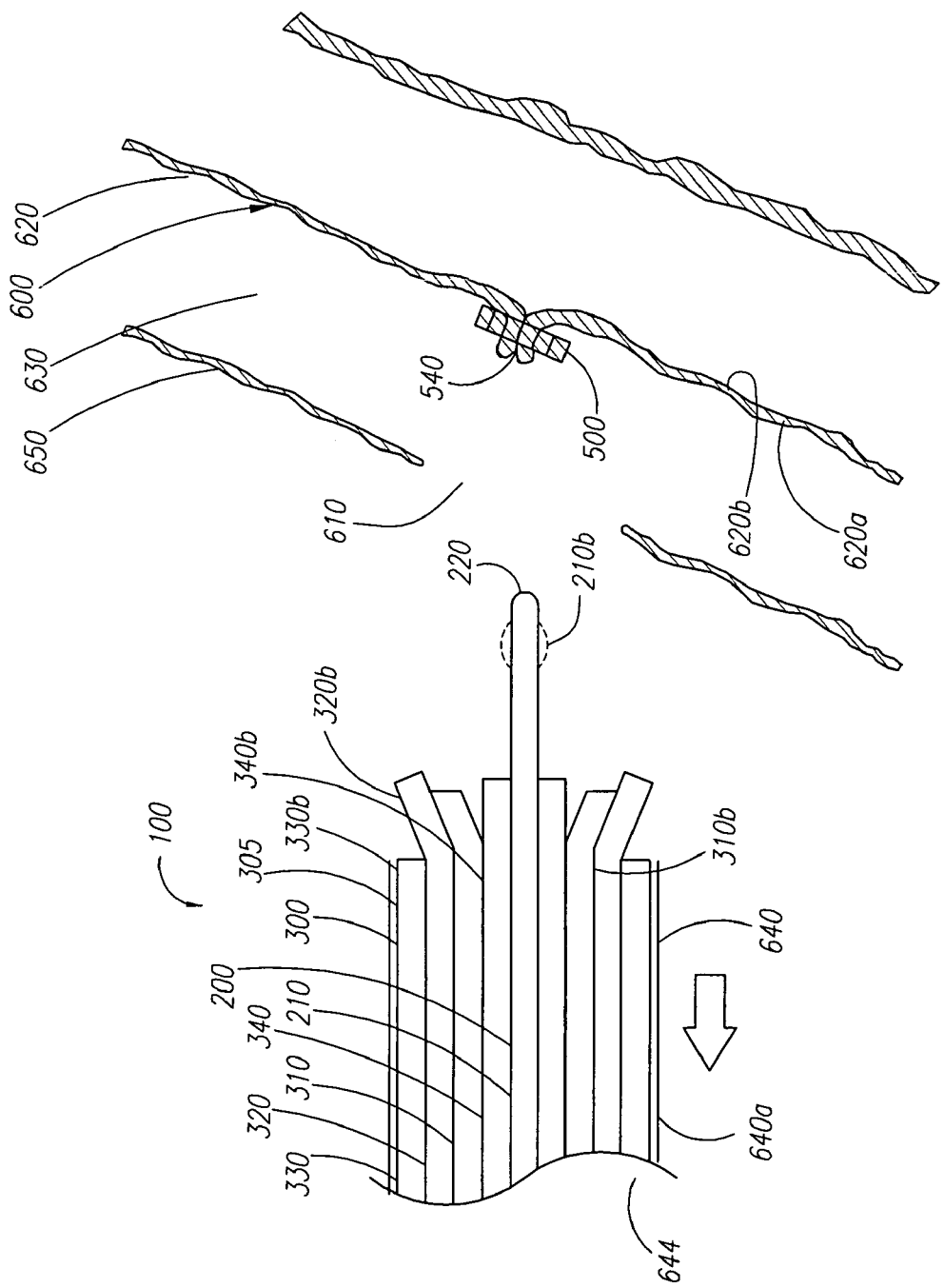
FIG. 8L illustrates the closure element of FIG. 8K drawing the engaged tissue substantially closed and/or sealed

Turning to FIG. 8K, the substantially tubular closure element 500", once deployed, begins to transition from the tubular configuration, returning to the natural, planar configuration with opposing tines 520 and a natural cross-section 530 of the closure element 500. Preferably, the substantially tubular closure element 500" substantially uniformly transitions from the tubular configuration to the natural, planar configuration. Rotating axially inwardly to form the opposing tines 520 of the closure element 500, the tines 520 draw the tissue 630 into the channel 540 as the substantially tubular closure element 500" forms the closure element 500. Also, the tissue 630 is drawn substantially closed and/or sealed as the cross-section 530' of the substantially tubular closure element 500" contracts to return to the natural cross-section 530 of the closure element 500. Thereby, the opening 610 in the blood vessel wall 620 can be drawn substantially closed and/or sealed via the closure element 500 as illustrated in FIG. 8L.

Figure 9:
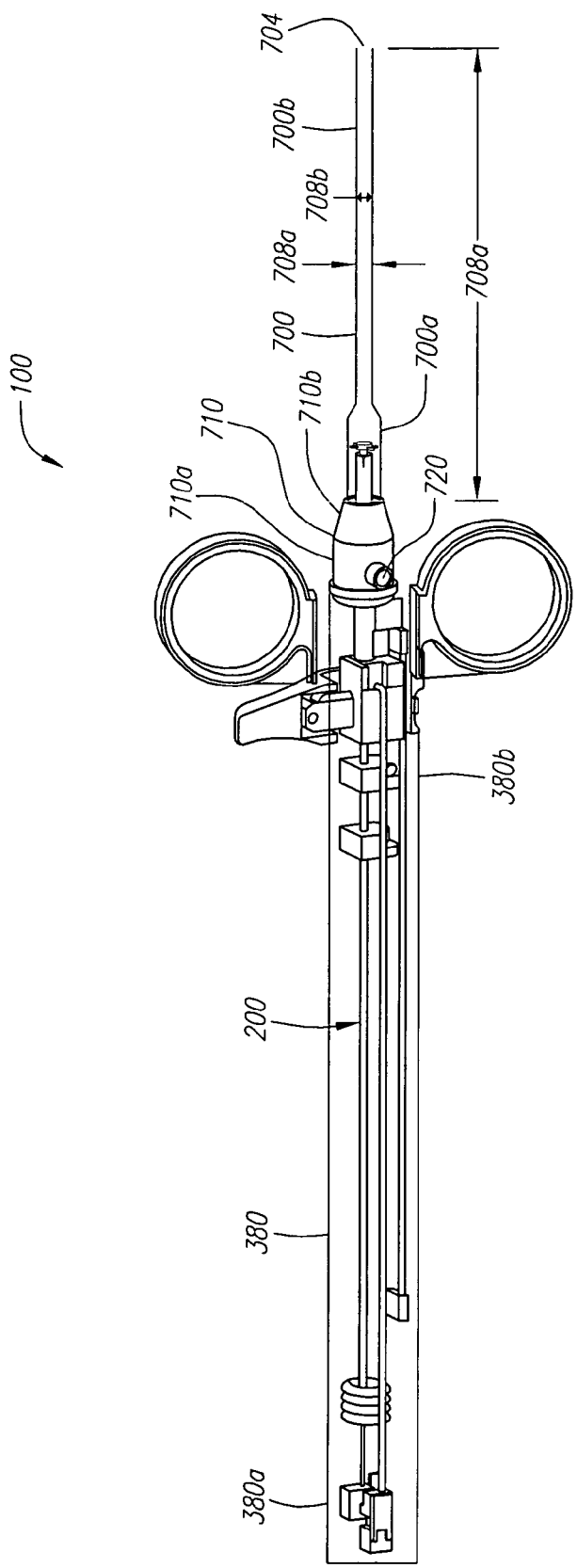
FIG. 9 illustrates one embodiment of an introducer sheath for the apparatus of FIG. 1.

It will be appreciated that the distal end region 380b of the housing 380 can be configured to couple with an introducer sheath 700 as shown in FIG. 9. Comprising a substantially flexible or semi-rigid tubular member, the introducer sheath 700 has a proximal end region 700a and a distal end region 700b and includes a predetermined length and a predetermined cross-section, both of which can be of any suitable dimension. The distal end region 700b is configured to facilitate insertion of the introducer sheath 700 through tissue 630 (shown in FIG. 8A) and/or into the opening 610 (shown in FIG. 8A) formed in and/or adjacent to the wall 620 (shown in FIG. 8A) of the blood vessel 600 (shown in FIG. 8A) or other body lumen. For example, the distal end region 430b can have a tapered tip (not shown) for facilitating substantially atraumatic introduction of the introducer sheath 700 through a passage formed in the tissue 630 and/or at least partially into the blood vessel wall 620, which is accessible via the passage. The introducer sheath 700 has an external cross-section 708b. The external cross-section 708b of introducer sheath 700 can be of any suitable dimension, and, as desired can be sized such that the introducer sheath 700 can be slidably received and advanced within the lumen 644 (shown in FIG. 8A) of the sheath 640.

The introducer sheath 700 also forms a lumen 704 that extends along a longitudinal axis of the introducer sheath 700 and substantially between the proximal and distal end regions 700a, 700b. The lumen 704 can have any suitable length 708a and internal cross-section 708b and is configured to slidably receive the tubular body 210 of the locator assembly 200 (shown in FIG. 4A) and/or the tube set 305 of the carrier assembly 300 (shown in FIG. 4A). Since the internal cross-section 708b of the introducer sheath 700 typically is less than or substantially equal to the predetermined cross-section 338b of the cover member 330, the introducer sheath 700 may be configured to radially expand, such as by stretching, to receive the tube set 305. Alternatively, or in addition, the introducer sheath 700 can be advantageously configured to split as the tube set 305 is received by, and advances within, the lumen 704 of the introducer sheath 700 in the manner described in more detail above with reference to the sheath 640 (shown in FIG. 8A). To facilitate the splitting, the introducer sheath 700 can include one or more splits (not shown), such as longitudinal splits, each split being provided in the manner known in the art. Each split is configured to split the introducer sheath 700 in accordance with a predetermined pattern, such as in a spiral pattern. It will be appreciated that, when the internal cross-section 708b of the introducer sheath 700 is greater than the predetermined cross-section 338b of the cover member 330, it may not be necessary for the introducer sheath 700 to be configured to radially expand and/or split.

The introducer sheath 700 can be coupled with the housing 380 via one or more cooperating connectors (not shown) such that the lumen 704 is substantially axially aligned with the tubular body 210 of the locator assembly 200 and/or the tube set 305 of the carrier assembly 300 and, as desired, may be removably and/or substantially permanently coupled with the housing 380. For example, a hub assembly 710 can be provided on the distal end region of the housing 380b and configured to couple with the proximal end region 700a of the introducer sheath 700. The proximal end region 430a of the introducer sheath 700 is coupled with, or otherwise provided on, a distal end region 710b of the hub assembly 710, such as via an adhesive, one or more cooperating connectors, and/or a thermo-mechanical joint.

The hub assembly 710 also includes a proximal end region 710a, which provides the one or more mating connectors for coupling the introducer sheath 700 with the housing 380 and forms a lumen (not shown), which extends substantially between the proximal end region 710a and the distal end region 710b. The lumen of the hub assembly 710 preferably has an internal cross-section or size that is greater than the internal cross-section or size of the lumen 704 of the introducer sheath 700. When the proximal end region 710a of the lumen 704 is properly connected with the hub assembly 710, the lumen of the hub assembly 710 is configured to communicate with the lumen 704 of the introducer sheath 700. As desired, the proximal end region 700a of the introducer sheath 700 may be flared to facilitate the connection between the introducer sheath 700 and the hub assembly 710.

When properly assembled, the hub assembly 710 preferably is substantially fluid tight such that the one or more devices can be inserted into the lumen 704 of the introducer sheath 700 without fluid passing proximally through the lumen 704. The hub assembly 710 can be made to be watertight, such as via one or more seals (not shown) and/or valves (not shown) in the manner known in the art. For example, the hub assembly 710 can include a thrust washer and/or valve, a guide for directing the devices into the lumen 704 of the introducer sheath 700, and/or a seal (collectively not shown). The various seals and/or guides can be coupled with the hub assembly 710 via, for example, one or more spacers and/or end caps (also collectively not shown).

As desired, the hub assembly 710 further can include one or more side ports 720. The side ports 720 can communicate with the lumen of the hub assembly 710 and/or the lumen 704 of the introducer sheath 700. At least one of the side ports 720 can be configured to be connected with, and to communicate with, tubing (not shown) to, for example, infuse fluids into the lumen 704 and through the introducer sheath 700. Alternatively, or in addition, at least one of the side ports 720 can provide a "bleed back" indicator, such as in the manner disclosed in the co-pending application Ser. No. 09/680,837. The disclosures of this reference and any others cited therein are expressly incorporated herein by reference.

The invention is susceptible to various modifications and alternative forms, and specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the claims.

What is claimed is:

1. An apparatus for delivering a closure element to an opening formed in a body lumen or body tissue, comprising:
    a closure element;
    a locator assembly having a distal end region configured to extend through tissue into said opening and to selectably engage said body lumen adjacent to said opening; and
    a carrier assembly being slidably coupled with said locator assembly, said carrier assembly having a carrier member supporting said closure element and a cover member retaining said closure element within said carrier assembly, said cover member having a distal end region formed with one or more longitudinal extensions that extend substantially radially inwardly and that are expandable radially outwardly as said closure element is moved distally for deployment, said carrier assembly being adapted for receiving said closure element, transitioning said closure element from a natural, substantially planar configuration to a substantially tubular configuration, and restraining said closure element substantially within said carrier assembly until said one or more longitudinal extensions formed at said distal end region expand radially outwardly as said closure element is moved distally, a distal end region of said carrier assembly being positionable through said tissue adjacent to said opening and being configured to distally deploy said closure element such that said closure element substantially uniformly expands to a cross-section that is greater than a natural cross-section of said closure element,
    wherein said closure element is configured to engage said tissue when deployed and to return to said natural, substantially planar configuration and said natural cross-section such that said tissue is drawn substantially closed,
    wherein said carrier member further is adapted for receiving said closure element such that said closure element transitions from said natural, substantially planar configuration to said substantially tubular configuration and a pusher member for distally deploying said closure element, said carrier member, said pusher member, and said cover member being slidably coupled, and
    wherein said one or more longitudinal extensions extend distally, at least partially closing a lumen defined by said cover member, and being configured to expand radially as a distal end region of said carrier member at least partially extends distally from said lumen defined by said cover member.

2. The apparatus of claim 1, wherein said carrier assembly further includes a support member being slidably coupled with said carrier member, said pusher member, and said cover member and being configured to provide radial support for said distal end region of said cover member and to inhibit one or more longitudinal extensions of said distal end region of said cover member from expanding prematurely when said closure element is deployed.

3. The apparatus of claim 2, wherein said carrier member, said pusher member, said cover member, and said support member are provided as a plurality of nested, telescoping members with a common longitudinal axis.

4. The apparatus of claim 2, wherein said support member defines a lumen, said distal end region of said locator assembly being substantially axially aligned with, and at least partially slidably disposed within, said lumen of said support member.

5. The apparatus of claim 1, further comprising a triggering system being coupled with a proximal end region of said locator assembly and a proximal end region of said carrier assembly and being configured to controlling relative axial movement of said end region of said locator assembly and said distal end region of said carrier assembly.

6. A system for closing an opening formed in a body lumen, comprising:
    a closure element having a natural, substantially-planar configuration and a natural cross-section and being deformable to form a substantially tubular configuration;
    a locator assembly having a distal end region configured to extend through tissue into said opening and to selectably engage said body lumen adjacent to said opening; and
    a carrier assembly being slidably coupled with said locator assembly, said carrier assembly having a carrier member supporting the closure element and a cover member retaining said closure element within said carrier assembly, said cover member having a distal end region formed with one or more longitudinal extensions that extend substantially radially inwardly and that are expandable radially outwardly as the closure element is moved distally for deployment, wherein said one or more longitudinal extensions extend distally at least partially closing a lumen defined by said cover member, said carrier assembly being adapted for receiving said closure element, transitioning said closure element from said natural, substantially planar configuration to a substantially tubular configuration, and retaining said closure element substantially within said carrier assembly until said one or more longitudinal extensions formed at said distal end region of said cover member expand radially outwardly as said closure element is moved distally, a distal end region of said carrier assembly being positionable through said tissue adjacent to said opening and being configured to distally deploy said closure element such that said closure element substantially uniformly expands to a cross-section that is greater than said natural cross-section, wherein said closure element is configured to engage said tissue when deployed and to return to said natural, substantially planar configuration and said natural cross-section such that said tissue is drawn substantially closed.

7. The system as recited in claim 6, further comprising an introducer sheath deployable into the body lumen, said introducer sheath comprising a proximal end, a distal end, and a lumen extending from the proximal end to the distal end.

8. The system as recited in claim 7, wherein said carrier assembly is slidably received within said lumen of said introducer sheath.

9. The system as recited in claim 6, wherein said carrier assembly further comprises a housing, at least a portion of said locator assembly being disposed within said housing.

10. A system for closing an opening formed in a body lumen, comprising:
- a closure element having a natural, substantially-planar configuration and a natural cross-section and being deformable to form a substantially tubular configuration;
- a locator assembly having a distal end region configured to extend through tissue into said opening and to selectably engage said body lumen adjacent to said opening; and
- a carrier assembly being slidably coupled with said locator assembly, said carrier assembly having a carrier member supporting the closure element and a cover member retaining said closure element within said carrier assembly, said cover member having a distal end region formed with one or more longitudinal extensions that extend substantially radially inwardly and that are expandable radially outwardly as the closure element is moved distally for deployment, said carrier assembly being adapted for receiving said closure element, transitioning said closure element from said natural, substantially planar configuration to a substantially tubular configuration, and retaining said closure element substantially within said carrier assembly until said one or more longitudinal extensions formed at said distal end region expand radially outwardly as said closure element is moved distally, a distal end region of said carrier assembly being positionable through said tissue adjacent to said opening and being configured to distally deploy said closure element such that said closure element substantially uniformly expands to a cross-section that is greater than said natural cross-section, wherein said closure element is configured to engage said tissue when deployed and to return to said natural, substantially planar configuration and said natural cross-section such that said tissue is drawn substantially closed, wherein said carrier assembly further comprises a housing, at least a portion of said locator assembly being disposed within said housing, and wherein said carrier assembly further comprises: said carrier member receiving said closure element such that said closure element transitions from said natural, substantially planar configuration to said substantially tubular configuration; and a pusher member for distally deploying said closure element;

wherein said carrier member, said pusher member, and said cover member being slidably coupled.

11. The system as recited in claim 10, wherein said carrier member, said pusher member, and said cover member are telescopically coupled together.

\* \* \* \* \*